United States Patent [19]

Rosen et al.

[11] Patent Number: 5,272,128
[45] Date of Patent: Dec. 21, 1993

[54] PHOSPHOSULFONATE HERBICIDES

[75] Inventors: Robert E. Rosen, Melrose Park; Damian G. Weaver; Jane W. Cornille, both of Lansdale; Lori A. Spangler, Churchville, all of Pa.

[73] Assignee: Rohm and Haas Company, Philadelphia, Pa.

[21] Appl. No.: 862,008

[22] Filed: Apr. 1, 1992

[51] Int. Cl.$^5$ .................... A01N 31/04; A01N 57/02
[52] U.S. Cl. .................... 504/195; 504/196; 504/197; 504/207; 504/208; 558/45
[58] Field of Search ............ 558/45; 71/87, 98, 103; 504/195, 196, 197, 207, 208

[56] References Cited

U.S. PATENT DOCUMENTS

| | | | |
|---|---|---|---|
| 4,059,432 | 11/1977 | Takematsu et al. | 71/87 |
| 4,740,608 | 4/1988 | Phillion | 558/45 |

FOREIGN PATENT DOCUMENTS 0284986  5/1971  U.S.S.R. .................. 558/45

OTHER PUBLICATIONS

Chem. Abs. 96:85903b; Holy et al.; 1982.
Chem. Abs. 83:27382b; Vizgert et al.; 1975.

*Primary Examiner*—Marianne M. Cintins
*Assistant Examiner*—Michael B. Hydorn
*Attorney, Agent, or Firm*—Terence P. Strobaugh; Clark R. Carpenter; Terry B. Morris

[57] ABSTRACT

This invention pertains to phosphosulfonates, having the general formula

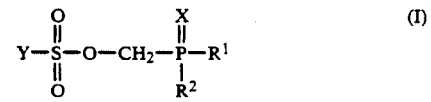

wherein Y is phenyl, naphthyl, benzyl, a $(C_5-C_8)$cycloalkyl, a 5-membered heteroaromatic ring, a 6-membered heteraromatic ring, a fused 5,6-membered heteroaromatic ring, or a fused 6,6-membered heteroaromatic ring; and X is oxygen or sulfur; and $R^1$ and $R^2$ are each independently selected from substituted or unsubstituted alkyl, alkoxy, alkylthio, alkenyloxy, alkynyloxy, haloalkoxy, cyanoalkoxy, alkoxyalkoxy, cycloalkyloxy, cycloalkylalkoxy, alkylideneiminooxy, chloro, amino, phenyl or phenoxy; or $R^1$ and $R^2$ are both alkoxy, taken together with the phosphorus atom to form a 6-membered oxygen-containing ring; compositions containing these compounds and their use as herbicides.

2 Claims, No Drawings

PHOSPHOSULFONATE HERBICIDES

BACKGROUND OF THE INVENTION

1. Field of the Invention

This invention pertains to phosphosulfonates, compositions containing these compounds and their use as herbicides.

The compounds of this invention provide control of many weed species, particularly grassy weeds. Although they may be used before or after the plant has emerged from the soil, they are especially effective when used to control growth of unwanted plants before the plants emerge from the soil.

Chemical weed control agents enable more efficient crop production by minimization of competing plant growth. New chemical means of controlling such unwanted vegetation are desirable to obtain better control of various agronomic weeds, for better crop safety and to overcome herbicide resistance.

The compounds of this invention control the growth of weeds while generally not injuring crops. The compounds primarily interfere with critical life processes in the germinating seed or seedling either causing plant death before growth above the soil or severely retarding growth of the plant so that the emerged shoot does not compete with the growing crop.

2. Description of Related Art

Czechoslovakian Patent CS 220,713 discloses dialkyl p-toluenesulfonyloxymethanephosphonates, specifically dimethyl and diethyl derivatives, as intermediates in the preparation of herbicides and insecticides. No information is provided as to any activity of the intermediates themselves.

Vizgert and Voloshin in Zhurnal Obshchei Khimii, Vol. 41, No. 9, pp 1991-4, disclose (dialkoxyphosphinyl)methyl arenesulfonates, including phenyl, 4-methylphenyl, 4-chlorophenyl and 3-nitrophenyl sulfonates. Vizgert et al. further disclose ethoxy, i-propoxy, n-propoxy, and n-butoxy as specific alkoxy substituents. No utility is suggested.

U.S. Pat. No. 4,456,464 relates to phenoxyphenoxyalkyl-, phenoxyphenylthioalkyl- and phenoxyphenylsulfonylalkyl-substituted phosphonates and phosphonites as herbicides.

U.S. Pat. No. 4,740,608 discloses (phosphomethyl)perfluoralkyl sulfonates as intermediates in the preparation of amino-phosphorous compounds, particularly N-phosphomethylglycine, a herbicide.

Chem. Abstracts 82: 72602p discloses [(dialkylphosphinyl)alkyl]-arenesulfonates, $(CH_3CH_2O)_2$-$P(O)CH(CH_3)O_3SC_6H_4R$, wherein R is hydrogen, 4-methylphenyl, 4-chlorophenyl and 3-nitrophenyl. No utility is disclosed.

Chem. Abstracts 83: 9009f discloses compounds of the formula $CH_3OP(O)(R)CHR^1SO_3C_6H_4CH_3$ wherein R is phenyl or methyl and $R^1$ is methyl or phenyl. No utility is disclosed.

Chem. Abstracts 83: 27382b discloses compounds of the formula $RC_6H_4SO_3CH_2P(O)(OR^1)_2$ wherein R is hydrogen, 4-methyl, 4-chloro or 3-nitro and $R^1$ is ethyl, isopropyl, butyl, 2-chloroethyl and pentyl. No utility is disclosed.

Chem. Abstracts 85: 160247u discloses compounds of the formula $C_6H_4SO_3CH_2P(O)(OR)_2$ wherein R is hexyl or butyl which are intermediates in the synthesis of O-(dialkyloxyphosphinylmethyl)phenylsulfonates.

Chem. Abstracts 88: 105477f discloses compounds of the formula $R^3SO_3CH_2P(O)(OR^2)_2$ where $R^3$ is phenyl or 4-methylphenyl and $R^2$ is ethyl, propyl or isopropyl as starting materials in the synthesis of α-substituted methylphosphonates.

Chem. Abstracts 96: 85903b discloses the synthesis of dialkyl p-toluenesulfonyloxymethanephosphonates.

Chem. Abstracts 97: 163126n discloses compounds of the formula $(phenoxy)_2P(O)CH_2OSO_2C_6H_4R$ where R is 4-methyl, 4-chloro, 4-bromo and 3-nitro. No utility is disclosed for these compounds.

Chem. Abstracts 98: 198639e discloses compounds of the formula $4\text{-}CH_3C_6H_4SO_3CH_2P(O)(OR^2)_2$ where $R^2$ is methyl or ethyl as reagents in the process of making 5'-O-phosphonylmethyl analogs of nucleoside-5'-phosphates, 5'-diphosphates and 5'-triphosphates.

SUMMARY OF THE INVENTION

The compounds of this invention are herbicides having the general formula

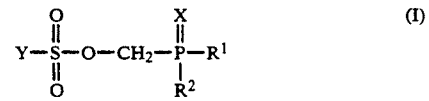

wherein

Y is a phenyl [e.g., $C_6H_5$—] group, a naphthyl [e.g., $C_{10}H_7$—] group, a benzyl [e.g., $C_6H_5CH_2$—] group, a $(C_5$-$C_8)$cycloalkyl group, a 5-membered heteroaromatic ring group having 1, 2, 3, or 4 heteroatoms independently selected from the group consisting of nitrogen, oxygen and sulfur atoms provided no more than one heteroatom is oxygen or sulfur, a 6-membered heteroaromatic ring group having 1, 2 or 3 nitrogen atoms, a fused 5,6-membered heteroaromatic ring group having 1-4 heteroatoms independently selected from the group consisting of nitrogen, oxygen and sulfur atoms provided no more than one heteroatom is oxygen or sulfur, or a fused 6,6-membered heteroaromatic ring group having 1-4 heteroatoms independently selected from the group consisting of nitrogen, oxygen and sulfur atoms provided no more than one heteroatom is oxygen or sulfur;

X is oxygen or sulfur; and $R^1$ and $R^2$ are each a group independently selected from alkyl, alkoxy, alkylthio, alkenyloxy, alkynyloxy, haloalkoxy, cyanoalkoxy, alkoxyalkoxy, cycloalkyloxy, cycloalkylalkoxy, alkylideneiminooxy, chloro and amino with one or two substituents selected from the group consisting of alkyl, alkenyl and phenyl provided that when phenyl is an amino substituent there is not more than one phenyl substituent, additionally $R^1$ may be selected from phenyl or phenoxy; or $R^1$ and $R^2$ are both alkoxy, taken together with the phosphorus atom to form a 6-membered oxygen-containing ring provided that when $R^1$ and $R^2$ are both alkoxy, Y is not phenyl, 4-methylphenyl, 4-chlorophenyl, 4-bromophenyl or 3-nitrophenyl.

The Y group may be substituted with one to three substituents each independently selected from halogen, cyano, nitro, alkoxy, haloalkoxy, alkyl, haloalkyl, phenyl, alkylcarbonyloxy, dialkylcarbamoyl and alkoxycarbonyl; additionally when the Y group is phenyl, naphthyl or benzyl, the ring may be substituted with four or five substituents selected from halogen, acetoxy, methyl, methoxy or halomethoxy provided no more than two substituents are selected from acetoxy, methyl, methoxy or halomethoxy.

DETAILED DESCRIPTION OF THE INVENTION

As used to describe the present invention, the term "alkyl", whether alone or as part of another group, refers to a straight or branched chain alkyl. Examples of alkyl include (without limiting) methyl, ethyl, n-propyl, isopropyl, n-butyl, sec-butyl, isobutyl, t-butyl, n-pentyl, isopentyl, neopentyl, hexyl, isohexyl, sec-hexyl, 2,2-dimethylbutyl and 2,3-dimethylbutyl; and, as further illustration, examples of alkoxy include methoxy, ethoxy, n-propoxy, isopropoxy, n-butoxy, sec-butoxy, isobutoxy, t-butoxy, isopentoxy, n-pentoxy, neopentoxy, hexyloxy, isohexyloxy, sec-hexyloxy, 2,2-dimethylbutoxy and 2,3-dimethylbutoxy. "Haloalkyl" and "haloalkoxy" refer to an alkyl and alkoxy group, respectively, substituted with from one to five halogen atoms, preferably from one to three halogen atoms, preferably fluorine or chlorine atoms. Examples of haloalkyl and haloalkoxy include (without limiting) trifluoromethyl, difluoromethoxy, 2,2,2-trifluoroethoxy, 2-chloroethoxy and trifluoromethoxy. "Halogen" includes fluorine, chlorine, bromine and iodine. "Alkenyl" and "alkynyl", whether alone or as part of another group, refer to straight and branched chain alkenyl and alkynyl, respectively. Examples of alkenyl and alkynyl include (without limiting) allyl, propargyl and 1-methylpropargyl; and, as further illustration, examples of alkenyloxy and alkynyloxy include (without limiting) allyloxy, propargyloxy and 1-methylpropargyloxy. "Alkylideneiminooxy" refers to an alkyl group double bonded to nitrogen which is in turn bonded to oxygen. An example of alkylideneiminooxy is isopropylideneiminooxy. "Cycloalkyl", whether alone or as part of another group, refers to a monocyclic nonaromatic carbocyclic ring. Examples of cycloalkyl include (without limiting) cyclobutyl, cyclopentyl and cyclohexyl. Examples of heteroaromatic rings include (without limiting) thienyl, isoxazolyl, pyrazolyl, triazolyl, quinolinyl, imidazolopyridinyl, pyrimidinyl, benzothiadiazolyl, thiazolyl, pyridyl (alternatively termed "pyridinyl" and includes, but is not limited to, pyridinyl oxides) and thiadiazolyl.

In one embodiment of this invention, Y is selected from phenyl, naphthyl, benzyl, a $(C_5-C_8)$cycloalkyl, a 5-membered heteroaromatic ring having 1, 2, 3 or 4 heteroatoms independently selected from the group consisting of nitrogen, oxygen and sulfur atoms provided no more than one heteroatom is oxygen or sulfur, a 6-membered heteroaromatic ring having 1, 2 or 3 nitrogen atoms, a fused 5,6-membered or fused 6,6-membered heteroaromatic ring having 1–4 heteroatoms independently selected from the group consisting of nitrogen, oxygen and sulfur atoms provided no more than one heteroatom is oxygen or sulfur; wherein each Y group may be substituted with up to three substituents each independently selected from halogen, cyano, nitro, $(C_1-C_6)$alkoxy, halo$(C_1-C_4)$alkoxy, $(C_1-C_6)$alkyl, halo$(C_1-C_4)$alkyl, phenyl, $(C_1-C_4)$alkylcarbonyloxy, di$(C_1-C_4)$alkylcarbamoyl and $(C_1-C_4)$alkoxycarbonyl, provided there is only one substituent on thiadiazolyl or tetrazolyl and further provided that triazolyl, thiazolyl or isothiazolyl can only have up to two substituents, or, wherein Y is phenyl, naphthyl or benzyl, each Y group may be substituted with four or five substituents selected from halogen, acetoxy, methyl, methoxy, difluoromethoxy and trifluoromethoxy provided no more than two substituents are selected from acetoxy, methyl, methoxy, difluoromethoxy and trifluoromethoxy; and provided that when $R^1$ and $R^2$ are both alkoxy, Y is not phenyl, 4-methylphenyl, 4-chlorophenyl, 4-bromophenyl or 3-nitrophenyl;

X is oxygen or sulfur, preferably oxygen; and $R^1$ and $R^2$ are each independently selected from $(C_1-C_6)$alkyl, $(C_1-C_6)$alkoxy, halo$(C_2-C_4)$alkoxy, $(C_1-C_4)$alkylthio, $(C_3-C_4)$alkenyloxy, $(C_3-C_4)$alkynyloxy, $(C_1-C_4)$alkoxy$(C_1-C_4)$alkoxy, $(C_4-C_8)$cycloalkyloxy, $(C_3-C_6)$cycloalkyl$(C_1-C_3)$alkoxy, cyano$(C_1-C_4)$alkoxy, $(C_2-C_4)$alkylideneiminooxy, chloro, and amino substituted with one or two substituents selected from $(C_1-C_4)$alkyl, $(C_2-C_4)$alkenyl and phenyl provided there is not more than one phenyl group on the amino group, additionally, $R^1$ may be selected from phenyl or phenoxy; or $R^1$ and $R^2$ are both alkoxy, taken together with the phosphorous atom to form a 6-membered oxygen-containing ring.

Preferred 5-membered heteroaromatic Y substituents are thienyl, pyrazolyl, isoxazolyl, triazolyl, tetrazolyl, thiazolyl, isothiazolyl, pyrrolyl, thiadiazolyl, and imidazolyl. Preferred thienyls are 2-thienyl and 3-thienyl. Preferred pyrazolyls are pyrazol-3-yl, pyrazol-4-yl, and pyrazol-5-yl; more preferably 5-chloro-1-methyl-3-$(C_1-C_3)$alkyl-4-pyrazolyls wherein $R_1$ is isopropoxy; and $R_2$ is methyl, ethyl, methoxy, or ethoxy. Preferred triazolyls are 1,2,4-triazol-3-yl and 1,2,4-triazol-5-yl, which triazolyls optionally have a dimethylcarbamoyl substituent attached to a nitrogen atom. Preferred tetrazolyls are tetrazol-1-yl and tetrazol-5-yl. Preferred isoxazolyls are isoxazol-4-yl and isoxazol-5-yl. Preferred thiazolyls are thiazol-2-yl, thiazol-4-yl, and thiazol-5-yl. Preferred isothiazolyls are isothiazol-4-yl and isothiazol-5-yl. Preferred pyrrolyls are pyrrol-2-yl and pyrrol-3-yl. A preferred thiadiazolyl is 1,3,4-thiadiazol-2-yl. Preferred imidazolyls are imidazol-2-yl, imidazol-4-yl, and imidazol-5-yl.

Preferred 6-membered heteroaromatic Y substituents are pyridinyl, pyrazinyl, pyridazinyl, and pyrimidinyl. Preferred pyridinyls are pyridin-2-yl and pyridin-3-yl. Other preferred pyridinyls are pyridin-2-yl N-oxide and pyridin-3-yl N-oxide. A preferred pyrazinyl is pyrazin-2-yl. A preferred pyridazinyl is pyridazin-3-yl. Preferred pyrimidinyls are pyrimidin-2-yl, pyrimidin-4-yl, and pyrimidin-5-yl.

Preferred fused 5,6-membered heteroaromatic Y substituents are indolyl, imidazolopyridinyl, pyrazolopyrimidinyl, benzoimidazolyl, benzothienyl, benzothiazolyl, thiadiazolyl, benzotriazolyl, and benzoxazolyl. Preferred indolyls are 1H-indol-2-yl and 1H-indol-3-yl. A preferred imidazolpyridinyl is imidazol[1,2-a]pyridin-3-yl. A preferred pyrazolopyrimidinyl is pyrazolo[1,5-a]pyrimidin-3-yl. Preferred benzoimidazolyls are benzoimidazol-2-yl and benzoimidazol-7-yl. Preferred benzothienyls are benzo[b]thien-2-yl and benzo[b]thien-3-yl. Preferred benzothiazolyls are benzothiazol-2-yl and benzothiazol-7-yl. A preferred benzothiadiazolyl is benzo-2,1,3-thiadiazol-4-yl. A preferred benzotriazolyl is 2H-benzotriazol-4-yl. Preferred benzoxazolyls are benzoxazol-2-yl and benzoxazol-4-yl.

A preferred fused 6,6-membered heteroaromatic Y substituent is quinolinyl.

All of the above preferred 5-membered heteroaromatic Y substituents, preferred 6-membered heteroaromatic Y substituents, preferred fused 5,6-membered heteroaromatic Y substituents, and preferred fused 6,6-membered heteroaromatic Y substituents can be unsubstituted or can be substituted with up to three substituents each independently selected from halogen, cyano, nitro, $(C_1-C_6)$alkoxy, halo$(C_1-C_4)$alkoxy, $(C_1-C_6)$alkyl, halo$(C_1-C_4)$alkyl, phenyl, $(C_1-C_4)$alkylcarbonyloxy, di$(C_1-C_4)$alkylcarbamoyl and $(C_1-C_4)$alkoxycarbonyl as specified hereinabove for all Y substituents.

In a preferred embodiment of this invention are compounds of formula (I), compositions containing those compounds and their use as herbicides wherein Y is (a) substituted phenyl, 1,2,4-triazol-3-yl, 1,2,4-triazol-5-yl, thien-2-yl (2-thienyl), thien-3-yl (3-thienyl), pyridin-2-yl (2-pyridinyl), pyridin-3-yl (3-pyridinyl), pyrazol-4-yl (4-pyrazolyl), pyrazol-5-yl (5-pyrazolyl), isoxazol-4-yl (4-isoxazolyl), benzo-2,1,3-thiadiazol-4-yl (4-benzo-2,1,3-thiadiazolyl), thiazol-5-yl (5-thiazolyl), and quinolin-8-yl (8-quinolinyl), each Y group having up to three substituents selected from halogen, cyano, $(C_1-C_4)$alkyl, $(C_1-C_4)$alkoxy, halo$(C_1-C_4)$alkoxy, halo$(C_1-C_4)$alkyl, $(C_1-C_2)$alkylcarbonyloxy, di$(C_1-C_3)$alkylcarbamoyl, and $(C_1-C_3)$alkoxycarbonyl; or (b) substituted phenyl having four or five substituents selected from fluoro, chloro, bromo, methyl, methoxy, difluoromethoxy, trifluoromethoxy and acetoxy provided there are no more than two acetoxy, methyl, methoxy, difluoromethoxy or trifluoromethoxy groups;

X is oxygen; and $R^1$ and $R^2$ are each independently $(C_1-C_4)$alkyl, $(C_1-C_4)$alkoxy, $(C_1-C_2)$alkoxy$(C_1-C_2)$alkoxy, halo$(C_2-C_4)$alkoxy, $(C_3-C_4)$alkenyloxy, $(C_3-C_4)$alkynyloxy, cyano$(C_1-C_4)$alkoxy and $(C_4-C_6)$cycloalkoxy; provided $R^1$ and $R^2$ are not both alkyl and that when $R^1$ and $R^2$ are both alkoxy, Y is not phenyl, 4-methylphenyl, 4-chlorophenyl, 4-bromophenyl or 3-nitrophenyl.

A more preferred embodiment of this invention is where Y is phenyl having up to three substituents, one of which is at the ortho position, independently selected from halogen, halo$(C_1-C_2)$alkyl, $(C_1-C_2)$alkoxy, halo$(C_1-C_4)$alkoxy and $(C_1-C_4)$alkyl provided when there are three substituents no more than two substituents are concurrently alkoxy or alkyl; X is oxygen; and $R^1$ and $R^2$ are each independently selected from $(C_1-C_2)$alkyl and $(C_1-C_4)$alkoxy; provided $R^1$ and $R^2$ are not both alkyl.

In an even more preferred embodiment of this invention Y is phenyl, monosubstituted in its ortho position, each substituent being independently selected from chloro, bromo, or trifluoromethyl; X is oxygen; and $R^1$ is selected from methoxy, ethoxy, isopropoxy, methyl and ethyl and $R^2$ is selected from ethoxy and isopropoxy. Additionally, Y may have a second substituent in its second ortho position selected from chloro, bromo, methyl, ethyl, isopropyl and methoxy, provided that when one substituent is chloro or bromo, the other substituent is not trifluoromethyl. Further, Y may be trisubstituted with chloro or bromo at the two ortho positions and methyl at the meta position.

Most preferably, Y is 2-chlorophenyl, 2-bromophenyl, 2,6-dichlorophenyl, 2-trifluoromethylphenyl, 2-chloro-6-isopropylphenyl, 2-chloro-6-methylphenyl, 2-methyl-6-trifluoromethylphenyl, 2-methoxy-6-trifluoromethylphenyl or 2,6-dichloro-3-methylphenyl; X is oxygen; and $R^1$ is selected from methoxy, ethoxy, isopropoxy, methyl and ethyl and $R^2$ is selected from ethoxy and isopropoxy.

The phosphosulfonates of this invention can be prepared by a one-step process starting with a sulfonyl chloride of the formula

$$YSO_2Cl \qquad \qquad (II)$$

wherein the Y group is as defined above. Compound II is then reacted with a hydroxymethylphospho compound of Formula III

$$HOCH_2PR^1R^2 \text{ with } X \text{ double bond on P} \qquad (III)$$

where $R^1$ and $R^2$ are as defined above, to yield a substituted phosphonate I of this invention.

Examples of suitable solvents for this reaction sequence include ethers, such as diethyl ether, tetrahydrofuran (THF), glyme; hydrocarbons such as benzene, toluene and xylene; and halocarbons, such as methylene chloride and ethylene dichloride.

The reaction is generally carried out at atmospheric pressure at a temperature of from about −20° C. to about 80° C. in the presence of an amine base, such as triethyl amine (TEA). Preferably, the temperature employed is in the range of from about 0° C. to about 45° C.

Alternatively, the anion of the hydroxymethylphospho compound of formula III is reacted with a sulfonyl chloride of formula II. The anion is formed, for example by reaction with sodium hydride in an inert organic solvent such as tetrahydrofuran. The reaction is generally carried out at atmospheric pressure at a temperature of from about −50° C. to about 20° C. and preferably, the temperature employed is in the range of from about −30° C. to about 0° C.

Another method of preparing the compounds of the invention is a phase transfer catalyzed reaction wherein the coupling reaction between the sulfonyl chloride of formula II and the hydroxymethylphospho compound of formula III is carried out in a two-phase solvent system in the presence of a phase transfer catalyst such as triethylbenzylammonium chloride.

Examples of suitable solvents include toluene or methylene chloride for one phase and aqueous sodium hydroxide solution for the other phase.

The reaction is generally carried out at atmospheric pressure at a temperature of from about −20° C. to about 50° C. and preferably, in the range of from about 0° C. to about 35° C.

When $R^1$ is alkoxy and $R^2$ is an alkoxy, alkyl or dialkylamino group, the compounds of the invention can be prepared by converting a phosphosulfonate of Formula I to the corresponding phosphonoyl chloride or phosphinoyl chloride IX using a reagent such phosphorous pentachloride or thionyl chloride. (Balthazor, T. M. and Flores, R. A., *J. Org. Chem.*, 1980, 45, 529 and Collins, David J., et al, *Aust. J. Chem*, 1984, 37, 1631).

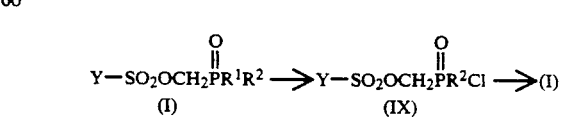

$$Y-SO_2OCH_2PR^1R^2 \text{ (=O)} \longrightarrow Y-SO_2OCH_2PR^2Cl \text{ (=O)} \longrightarrow (I)$$
$$(I) \qquad \qquad \qquad (IX)$$

The reaction can be carried out in a halocarbon solvent, such as methylene dichloride, or in a hydrocarbon solvent such as toluene, at a temperature range of about 0° C. to about 150° C. Preferably, the temperature range is from about 10° C. to about 120° C.

The phosphonoyl chloride or phosphinoyl chloride IX can then be reacted with alcohols such as methanol or ethanol, mono- or disubstituted amines such as di-n-propylamine or alkyl mercaptans such as isopropyl mercaptan to yield the new desired product I.

This reaction is typically carried out in a halocarbon solvent, such as methylene dichloride, a hydrocarbon solvent such as toluene, or an ether solvent, such as diethyl ether or THF, in the presence of an equivalent of an amine base, such as TEA, either with or without a catalytic agent such as 4-dimethylaminopyridine (DMAP), at a temperature range of about −40° C. to about 120° C. Preferably, the temperature range is from about −15° C. to about 30° C. for phosphonoyl and phosphinoyl chlorides and from about 60° C. to about 120° C. for phosphonamidoyl chlorides ($R^2$ is dialkylamino).

Alternatively, compounds of the formula I where $R^1$ and $R^2$ are the same alkoxy, such as methoxy or isopropyloxy, can be prepared from the phosphonoyl dichloride X by the addition

of the appropriate alcohol such as methanol or isopropanol. Typically, the addition can be accomplished in ether solvents such as diethyl ether, tetrahydrofuran and glyme, or in halocarbon solvents such as methylene dichloride in the preence of an amine base, such as triethyl amine with an excess of the alcohol in a temperature range of about −40° C. to about 65° C. The preferred temperature range is from about −15° C. to about 30° C.

The phosphonoyl dichloride X can be prepared from compound I, where $R^1$ and $R^2$ are both isopropyloxy or ethoxy moieties by reacting with $PCl_5$ in a hydrocarbon solvent, such as toluene or a halocarbon solvent, such as carbon tetrachloride, at a temperature range of about 30° C. to about 180° C. The preferred temperature range is from about 40° C. to about 150° C.

The sulfonyl chlorides of Formula II can be prepared by the following procedures:

A. The sulfonyl chlorides of formula II where Y is as defined above can be prepared from the corresponding thiophenols or disulfides by methods known in the literature (Gilbert, E. E., "Sulfonations and Related Reactions," pp. 201-239, *Interscience Publications*, 1965, New York).

B. The sulfonyl chlorides can alternatively be prepared by directly chlorosulfonating a compound of Formula V wherein Y is aryl or heteroaromatic, as described in the literature. (Organic Reactions, Vol III, Chapter 4, Roger Adams, ed., 1962, pp. 141-197).

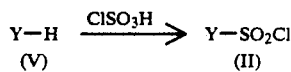

C. Appropriately substituted sulfonic acids or their salts where M is hydrogen, a cation of a Group I metal, such as sodium or potassium, or a cation of a Group II metal, such as magneisum, of Formula VI can be converted to the corresponding sulfonyl chlorides by methods

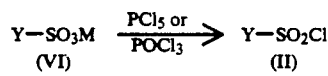

described in the literature ("Organic Synthesis", Volume I, 84 and Organic Synthesis", Volume V, 196).

D. The sulfinate salt of Formula VII, where M is lithium or magnesium cation can be prepared by metalating compound V as described in the literature and reacting the resulting intermediate VII

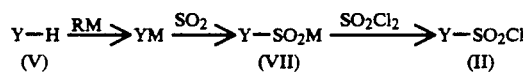

with sulfuryl chloride to obtain the sulfonyl chloride II.

E. A Grignard reagent can be used to prepare compounds of Formula VII, where M is MgBr from the appropriately substituted aryl bromide, which when quenched with sulfur dioxide yields the intermediate VII which is subsequently treated with sulfuryl chloride as outlined above. Alternatively, the Grignard intermediate is quenched with sulfuryl chloride to yield the sulfonyl chloride II directly.

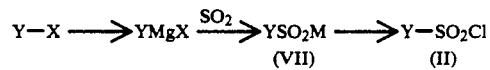

F. The sulfonyl chloride II wherein Y is aryl or heteroaromatic can also be prepared from the corresponding aniline VIII through the diazonium salt prepared in hydrochloric acid with or without sulfuric acid, as described in the literature (*Organic Synthesis*, Vol. 60, pp. 121-126).

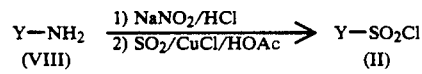

The hydroxymethylphospho compound of formula III can be prepared by the following synthetic sequences:

A. When $R^1$ and $R^2$ are both alkoxy, a phosphite of Formula IV

can be reacted with paraformaldehyde in the presence of an amine base, such as TEA, at a temperature of from about room temperature to about 230° C. as described in the literature (Phillion, D. P. et al., Tet. Lett., 1986, 27(13), 1477-1480 and Chem. Abstracts 72: 21745y). Preferably, the reaction is carried out in a temperature range of from about 35° C. to about 180° C.

B. When $R^1$ is alkoxy and $R^2$ is alkyl, a similar reaction can be carried out with compound IV and paraformaldehyde either in the presence or absence of an amine base, such as TEA, and either in the presence or absence of a solvent, such as THF. The temperature range for this reaction is from about room temperature to about 200° C. as described in the literature (Frank, A. W., Chem. Rev., 1961, 61, 389-424 and Chem. Abstracts 80: 241e). Preferably, the temperature range is from about 35° C. to about 150° C.

C. When $R^1$ and $R^2$ are both alkyl, the preparation of compound III can be carried out starting from compound IV and using an aqueous solution of formaldehyde, as described in the literature (Miller, R. C. et al., J. Amer. Chem. Soc., 79, 424-427; Rauhut, M. M. et al., J. Org. Chem., 1961, 26, 4626-4628; and Baerman, C. et al., Ger. Offen., 2,060,216, Jun. 22, 1972).

D. The hydroxymethylphosphonate compound III where $R^1$ and $R^2$ are the same or different alkoxy can be prepared by an alternate procedure starting from compound III, where $R^1$ and $R^2$ are preferably both isopropyloxy or ethoxy, or $R^2$ is dialkylamino, by acylating with acetyl chloride in the presence of an amine base such as triethyl amine according to the literature procedure of Chem. Abstracts 72: 21745y to yield compound XI.

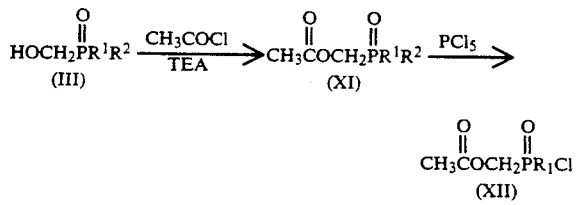

Compound XI can be converted to the phosphonoyl chloride XII with PCl$_5$ analogously to the preparation of compound IX above. Typically this reaction is conducted in a halocarbon solvent such as methylene chloride at a temperature range of about −20° C. to about 60° C. Preferably, the temperature is from about 10° C. to about 40° C.

The phosphonoyl chloride XII can be reacted with an alcohol such as methanol or an amine to yield a new compound XI. This can be accomplished as described above for the preparation of compound I from IX.

The new compound XI can be deacetylated to yield a new compound III by treating XI with a nucleophilic base. Typically, the base used is an alkoxide generated in situ from the corresponding alcohol and potassium carbonate or sodium metal. The reaction solvents are an excess of the alcohol and the temperature is typically from about 0° C. to about 50° C. with the preferable temperature range from about 10° C. to about 35° C.

The phosphite of Formula IV can be prepared by the following synthetic sequences.

A. When $R^1$ and $R^2$ are both the same alkoxy or together form a cyclic ester, phosphorus trichloride can be reacted with an alcohol or a 1,3-diol as described in the literature (Craig, W. E. et al., Can. J. Chem., 1967, 45, 2501-2520); U.S. Pat. No. 2,495,958.

B. When $R^1$ is alkoxy and $R^2$ of compound IV is alkyl, IV can be prepared from phosphorous trichloride by the addition of an alkyl Grignard reagent. The Grignard addition is typically conducted in an ether solvent, such as diethyl ether, at a temperature range of from about −78° C. to about −20° C. Preferably, the temperature range is from about −78° C. to about −45° C. The resulting alkylphosphine dichloride is then reacted with a suitable alcohol as described above to yield the described intermediate IV (King, R. B., et al, J. Org. Chem., 41 (1976) 972-977).

C. When both $R^1$ and $R^2$ are alkyl, compound IV can be prepared as described in the literature (Hayes, R. H., J. Org. Chem., 1968, 33(10), 3690-3694).

D. When $R^1$ and $R^2$ are different alkoxy groups, compound III can be prepared by the stepwise addition of different alcohols, preferably with differing steric requirements, to phosphorous trichloride. Base is added to the reaction mixture after the addition of each alcohol. Preferably the same base is used throughout the reaction sequence. The addition of the first alcohol is carried out at a low temperature, preferably between about −15° C. and about 15° C., most preferably around 0° C., followed by the addition of one equivalent of base. After the addition of the second alcohol, preferably two equivalents, and the subsequent addition of one equivalent of base, the reaction mixture is warmed to about 25° C. to about 50° C., preferably to about 40° C.

The following examples will further illustrate this invention but are not intended to limit it in any way. In Tables 1A to 1E examples of compounds of the invention are listed along with an indication of physical state or melting point and $^{31}$P NMR data. Specific illustrative preparations of the compounds are described after Table 1E.

TABLE 1A

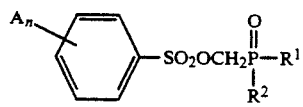

| Cpnd | A$_n$ | R$^1$ | R$^2$ | $^{31}$P-NMR | State or Melting Point °C. |
|---|---|---|---|---|---|
| 1. | 4-CH$_3$ | OC$_2$H$_5$ | OC$_2$H$_5$ | 15.2 | oil |
| 2. | 4-CH$_3$ | OCH$_3$ | OCH$_3$ | 17.8 | oil |
| 3. | 2-Cl | OC$_2$H$_5$ | OC$_2$H$_5$ | 14.6 | oil |
| 4. | 4-Cl | OC$_2$H$_5$ | OC$_2$H$_5$ | 14.9 | oil |
| 5. | H | OC$_2$H$_5$ | OC$_2$H$_5$ | 15.1 | oil |
| 6. | 2-CO$_2$CH$_3$ | OC$_2$H$_5$ | OC$_2$H$_5$ | 15.1 | oil |
| 7. | 3-Cl, 4-CH$_3$ | OC$_2$H$_5$ | OC$_2$H$_5$ | 14.9 | 61-67 |
| 8. | 2-NO$_2$ | OC$_2$H$_5$ | OC$_2$H$_5$ | 14.3 | oil |
| 9. | 2-Cl, 5-Cl | OC$_2$H$_5$ | OC$_2$H$_5$ | 14.4 | 52-60 |
| 12. | 4-F | OC$_2$H$_5$ | OC$_2$H$_5$ | 15.0 | oil |
| 13. | 2-Cl, 3-Cl | OC$_2$H$_5$ | OC$_2$H$_5$ | 14.5 | oil |
| 14. | 3-Cl, 4-Cl | OC$_2$H$_5$ | OC$_2$H$_5$ | 14.6 | wax |
| 15. | 4-CH$_3$ | O(CH$_2$)$_3$CH$_3$ | O(CH$_2$)$_3$CH$_3$ | 15.2 | oil |
| 16. | 2-Cl, 5-Cl | O(CH$_2$)$_3$CH$_3$ | O(CH$_2$)$_3$CH$_3$ | 14.4 | oil |

TABLE 1A-continued

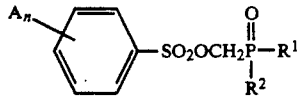

| Cpnd | $A_n$ | $R^1$ | $R^2$ | $^{31}$P-NMR | State or Melting Point °C. |
|---|---|---|---|---|---|
| 17. | 4-OCH$_3$ | OC$_2$H$_5$ | OC$_2$H$_5$ | 15.4 | oil |
| 19. | 2-Cl, 5-Cl | OC$_2$H$_5$ | NHCH$_2$CH=CH$_2$ | 18.9 | 75–82 |
| 21. | 3-Cl | OC$_2$H$_5$ | OC$_2$H$_5$ | 14.8 | oil |
| 22. | 3-CH$_3$ | OC$_2$H$_5$ | OC$_2$H$_5$ | 15.2 | oil |
| 24. | 2-OCH$_3$, 5-OCH$_3$ | OC$_2$H$_5$ | OC$_2$H$_5$ | 15.5 | oil |
| 25. | 3-Cl, 5-Cl | OC$_2$H$_5$ | OCH$_2$H$_5$ | 14.5 | oil |
| 26. | 3-NO$_2$ | OC$_2$H$_5$ | OC$_2$H$_5$ | 14.5 | 65–69 |
| 27. | 2-Cl, 5-Cl | OCH$_2$CH=CH$_2$ | OCH$_2$CH=CH$_2$ | 15.2 | oil |
| 28. | 2-CH$_3$, 5-NO$_2$ | OC$_2$H$_5$ | OC$_2$H$_5$ | 14.6 | 64–67 |
| 30. | 2-CF$_3$ | OC$_2$H$_5$ | OC$_2$H$_5$ | 14.4 | oil |
| 31. | 3-CF$_3$ | OC$_2$H$_5$ | OC$_2$H$_5$ | 14.6 | oil |
| 32. | 4-CF$_3$ | OC$_2$H$_5$ | OC$_2$H$_5$ | 14.6 | oil |
| 33. | 3-NO$_2$, 4-CH$_3$ | OC$_2$H$_5$ | OC$_2$H$_5$ | 15.2 | 74–76 |
| 34. | 2-Cl, 4-Cl | OC$_2$H$_5$ | OC$_2$H$_5$ | 15.1 | oil |
| 35. | 2-Cl, 5-Cl | OCH$_2$CH$_2$Cl | OCH$_2$CH$_2$Cl | 15.5 | wax |
| 37. | 2-Cl, 5-Cl | OCH$_3$ | OCH$_3$ | 17.5 | oil |
| 38. | 2-NO$_2$ | OCH$_3$ | OCH$_3$ | 17.5 | oil |
| 39. | 2-Cl, 5-Cl | OC$_2$H$_5$ | N(CH$_2$CH=CH$_2$)$_2$ | 19.6 | oil |
| 43. | 2-NO$_2$, 4-Cl | OC$_2$H$_5$ | OC$_2$H$_5$ | 14.1 | oil |
| 44. | 2-Cl, 6-Cl | OC$_2$H$_5$ | OC$_2$H$_5$ | 14.4 | wax |
| 45. | 2-Cl, 6-CH$_3$ | OC$_2$H$_5$ | OC$_2$H$_5$ | 15.0 | 41.5–43 |
| 46. | 2-Cl, 5-Cl | OCH(CH$_3$)$_2$ | OCH(CH$_3$)$_2$ | 12.2 | 49.5–51 |
| 47. | 2-Cl, 5-NO$_2$ | OC$_2$H$_5$ | OC$_2$H$_5$ | 14.1 | 76–78 |
| 49. | 2-Cl, 5-Cl | OCH$_2$CH$_2$CH$_3$ | OCH$_2$CH$_2$CH$_3$ | 14.3 | 41–43 |
| 52. | 2-Br, 5-CF$_3$ | OC$_2$H$_5$ | OC$_2$H$_5$ | 14.2 | 63–65 |
| 53. | 2-Br, 5-Br | OC$_2$H$_5$ | OC$_2$H$_5$ | 14.4 | 77–79 |
| 54. | 2-CN | OC$_2$H$_5$ | OC$_2$H$_5$ | 14.2 | oil |
| 55. | 2-Cl, 6-Cl | OCH(CH$_3$)$_2$ | OCH(CH$_3$)$_2$ | 12.2 | 55–57 |
| 56. | 2-NO$_2$, 5-Cl | OC$_2$H$_5$ | OC$_2$H$_5$ | 14.0 | 54–55 |
| 57. | 2-CF$_3$, 4-Cl | OC$_2$H$_5$ | OC$_2$H$_5$ | 14.3 | 43–45 |
| 58. | 2-NO$_2$, 4-CH$_3$ | OC$_2$H$_5$ | OC$_2$H$_5$ | 14.3 | oil |
| 60. | 2-CH$_3$, 5-Cl | OC$_2$H$_5$ | OC$_2$H$_5$ | 15.0 | oil |
| 61. | 2-Cl, 5-CH$_3$ | OC$_2$H$_5$ | OC$_2$H$_5$ | 14.7 | oil |
| 62. | 2-NO$_2$, 4-OCH$_3$ | OC$_2$H$_5$ | OC$_2$H$_5$ | 14.5 | 55–57 |
| 63. | 2-Cl, 5-Cl | OC$_2$H$_5$ | N(C$_2$H$_5$)$_2$ | 19.4 | oil |
| 64. | 2-Cl, 6-CH$_3$ | OC$_2$H$_5$ | N(CH$_3$)C$_6$H$_5$ | 17.4 | oil |
| 65. | 2-Cl, 6-CH$_3$ | OC$_2$H$_5$ | C$_2$H$_5$ | 47.0 | oil |
| 68. | 2-F, 4-Br | OC$_2$H$_5$ | OC$_2$H$_5$ | 14.4 | oil |
| 70. | 2-Br | OC$_2$H$_5$ | OC$_2$H$_5$ | 14.7 | oil |
| 71. | 2-F | OC$_2$H$_5$ | OC$_2$H$_5$ | 14.6 | oil |
| 72. | 2-Cl, 6-CH$_3$ | OCH(CH$_3$)$_2$ | OCH(CH$_3$)$_2$ | 12.8 | wax |
| 73. | 2-Cl, 6-CH$_3$ | OC$_2$H$_5$ | OCH$_2$CF$_3$ | 16.3 | 50–51 |
| 74. | 2-CF$_3$ | OC$_2$H$_5$ | OCH$_2$CF$_3$ | 15.8 | 54–55 |
| 75. | 2-CF$_3$, 4-F | OC$_2$H$_5$ | OC$_2$H$_5$ | 14.3 | oil |
| 76. | 2-F, 5-CF$_3$ | OC$_2$H$_5$ | OC$_2$H$_5$ | 14.2 | oil |
| 77. | 2-F, 4-F | OC$_2$H$_5$ | OC$_2$H$_5$ | 14.5 | oil |
| 78. | 2-Cl, 6-CH$_3$ | OC$_2$H$_5$ | OC$_6$H$_5$ | 11.7 | oil |
| 79. | 2-Cl, 6-CH$_3$ | OC$_2$H$_5$ | NHCH(CH$_3$)$_2$ | 18.3 | 65.5–67 |
| 80. | 2-CF$_3$ | OC$_2$H$_5$ | C$_2$H$_5$ | 46.8 | 59–60.5 |
| 81. | 2-CF$_3$, 4-Br | OC$_2$H$_5$ | OC$_2$H$_5$ | 14.2 | oil |
| 82. | 2-CH$_3$ | OC$_2$H$_5$ | OC$_2$H$_5$ | 15.3 | oil |
| 83. | 2-CH(CH$_3$)$_2$ | OC$_2$H$_5$ | OC$_2$H$_5$ | 15.4 | oil |
| 85. | 2-OCH$_3$, 5-Cl | OC$_2$H$_5$ | OC$_2$H$_5$ | 15.2 | oil |
| 86. | 2-OCH$_3$ | OC$_2$H$_5$ | OC$_2$H$_5$ | 15.6 | oil |
| 87. | 2-OCF$_3$ | OC$_2$H$_5$ | OC$_2$H$_5$ | 14.6 | oil |
| 88. | 2-Cl, 6-CH$_3$ | OC$_2$H$_5$ | N(CH$_2$CH$_2$CH$_3$)$_2$ | 19.9 | oil |
| 89. | 2-Cl, 6-CH$_3$ | OC$_2$H$_5$ | C$_6$H$_5$ | 30.8 | 71–73 |
| 90. | 2-CF$_3$ | OC$_2$H$_5$ | C$_6$H$_5$ | 30.3 | oil |
| 91. | 2-Cl, 6-CH$_3$ | N(CH$_2$CH$_2$CH$_3$)$_2$ | N(CH$_2$CH$_2$CH$_3$)$_2$ | 24.3 | oil |
| 92. | 2-Cl, 6-CH$_3$ | C$_2$H$_5$ | C$_2$H$_5$ | 48.5 | oil |
| 93. | 2-Cl, 6-CH$_3$ | OC$_2$H$_5$ | SCH(CH$_3$)$_2$ | 42.3 | oil |
| 94. | 2-Cl, 6-CH$_3$ | OC$_2$H$_5$ | OCH$_2$CH$_2$OCH$_3$ | 15.7 | oil |
| 95. | 2-Cl, 6-CH$_3$ | OC$_2$H$_5$ | OCH$_2$CH$_2$CH$_3$ | 14.9 | oil |
| 96. | 2-Cl, 6-CH$_3$ | OC$_2$H$_5$ | OCH(CH$_3$)$_2$ | 13.9 | oil |
| 97. | 2-Cl, 6-CH$_3$ | OC$_2$H$_5$ | N(CH$_3$)$_2$ | 20.6 | oil |
| 98. | 2-Cl, 6-CH$_3$ | CH$_2$CH$_2$CH$_3$ | CH$_2$CH$_2$CH$_3$ | 45.5 | 51–53 |
| 99. | 2-Cl, 6-CH$_3$ | OC$_2$H$_5$ | CH(CH$_3$)$_2$ | 49.0 | liquid |
| 100. | 2-CF$_3$ | CH$_2$CH$_2$CH$_3$ | CH$_2$CH$_2$CH$_3$ | 45.4 | oil |
| 101. | 2-CF$_3$ | OC$_2$H$_5$ | CH(CH$_3$)$_2$ | 48.6 | oil |
| 102. | 2-Cl, 6-CH$_3$ | OC$_2$H$_5$ | CH$_3$ | 44.0 | oil |
| 103. | 2-CF$_3$ | OC$_2$H$_5$ | CH$_3$ | 43.5 | 91–92.5 |
| 104. | 2-Cl, 6-CH$_3$ | OC$_2$H$_5$ | O-cyclopentyl | 14.0 | oil |
| 105. | 2-Cl, 6-CH$_3$ | OC$_2$H$_5$ | OCH$_2$CH(CH$_3$)$_2$ | 14.8 | oil |

TABLE 1A-continued $$A_n\text{-C}_6H_4\text{-SO}_2\text{OCH}_2\overset{\overset{O}{\|}}{\underset{R^2}{P}}-R^1$$

| Cpnd | $A_n$ | $R^1$ | $R^2$ | $^{31}$P-NMR | State or Melting Point °C. |
|---|---|---|---|---|---|
| 106. | 2-Cl, 6-CH$_3$ | OC$_2$H$_5$ | OCH(CH$_3$)C$_2$H$_5$ | 14.0 | oil |
| 107. | 2-NO$_2$, 6-CH$_3$ | OC$_2$H$_5$ | OC$_2$H$_5$ | 14.5 | wax |
| 108. | 2-Cl, 6-Cl | OC$_2$H$_5$ | OCH(CH$_3$)$_2$ | 13.3 | oil |
| 109. | 2-Cl, 6-Cl | OCH$_3$ | OCH$_3$ | 17.0 | 79-80 |
| 111. | 2-Cl, 6-Cl | OCH$_3$ | OCH(CH$_3$)$_2$ | 14.7 | oil |
| 113. | 2-NO$_2$, 6-Cl | OC$_2$H$_5$ | OC$_2$H$_5$ | 13.8 | oil |
| 114. | 2-CH$_3$, 6-CH$_3$ | OC$_2$H$_5$ | OC$_2$H$_5$ | 15.6 | oil |
| 115. | 2-Cl, 6-CH$_3$ | OCH$_3$ | OCH$_3$ | 17.6 | 55.5-57.5 |
| 116. | 2-Cl, 6-CH$_3$ | OCH$_3$ | OCH(CH$_3$)$_2$ | 15.2 | oil |
| 117. | 2-Cl, 6-CH$_3$ | OC$_2$H$_5$ | OCH$_3$ | 16.3 | oil |
| 119. | 2-Cl, 6-CH$_3$ | OCH(CH$_3$)$_2$ | C$_2$H$_5$ | 46.0 | 40-42 |
| 120. | 2-Cl, 6-Cl | OCH(CH$_3$)$_2$ | CH$_2$CH$_2$CH$_3$ | 43.9 | 68.5-69.5 |
| 121. | 2-Cl, 6-CH$_3$ | OCH$_3$ | CH$_2$CH(CH$_3$)$_2$ | 46.9 | oil |
| 122. | 2-Cl, 6-CH$_3$ | OCH$_3$ | CH$_2$C(CH$_3$)$_3$ | 46.2 | oil |
| 123. | 2-Cl, 6-CH$_3$ | OCH(CH$_3$)$_2$ | CH$_3$ | 42.4 | 70-72 |
| 125. | 2-OCH$_3$, 6-OCH$_3$ | OC$_2$H$_5$ | OC$_2$H$_5$ | 16.0 | oil |
| 126. | 2-C$_2$H$_5$, 6-C$_2$H$_5$ | OC$_2$H$_5$ | OC$_2$H$_5$ | 15.6 | oil |
| 127. | 2-Cl, 6-CH$_3$ | OCH$_3$ | OCH(CH$_3$)C≡CH | 16.5, 16.3 | oil |
| 128. | 2-Cl, 6-CH$_3$ | OCH$_3$ | OCH$_2$C≡CH | 17.7 | oil |
| 129. | 2-OCHF$_2$, 6-CH$_3$ | OCH(CH$_3$)$_2$ | OCH(CH$_3$)$_2$ | 13.0 | oil |
| 130. | 2-Cl, 6-CH$_3$ | Cl | OCH(CH$_3$)$_2$ | 24.7 | oil |
| 132. | 2-Cl, 6-Cl | OCH(CH$_3$)$_2$ | C$_2$H$_5$ | 45.4 | 58-59.5 |
| 141. | 2-CF$_3$ | OCH$_3$ | OCH(CH$_3$)$_2$ | 14.6 | oil |
| 142. | 2-CF$_3$, 6-CH$_3$ | OCH$_3$ | OCH(CH$_3$)$_2$ | 15.2 | oil |
| 143. | 2-CF$_3$ | OCH(CH$_3$)$_2$ | OCH(CH$_3$)$_2$ | 12.3 | oil |
| 153. | 2-CF$_3$, 6-OCH$_3$ | OCH(CH$_3$)$_2$ | OCH(CH$_3$)$_2$ | 13.1 | oil |
| 154. | 2-OCH$_3$, 4-CF$_3$ | OCH(CH$_3$)$_2$ | OCH(CH$_3$)$_2$ | 13.0 | oil |
| 157. | 2-CF$_3$, 6-OCH$_3$ | OCH$_3$ | OCH(CH$_3$)$_2$ | 15.4 | oil |
| 158. | 2-CH$_3$, 3-Cl | OCH(CH$_3$)$_2$ | OCH(CH$_3$)$_2$ | 12.9 | oil |
| 159. | 2-OCH$_3$, 5-Cl | OCH(CH$_3$)$_2$ | OCH(CH$_3$)$_2$ | 13.1 | oil |
| 161. | 2-Cl, 6-CH$_3$ | OCH$_2$C(CH$_3$)$_3$ | OC$_2$H$_5$ | 14.9 | oil |
| 162. | 2-Cl, 6-CH$_3$ | O-cyclopentyl | C$_2$H$_5$ | 46.0 | oil |
| 163. | 2-Cl, 6-CH$_3$ | OCH(CN)CH$_3$ | OC$_2$H$_5$ | 15.8, 16.4 | oil |
| 164. | 2-Cl, 6-CH$_3$ | ON=C(CH$_3$)$_2$ | OC$_2$H$_5$ | 19.1 | 103-104 |
| 165. | 2-Cl, 6-CH$_3$ | OCH$_2$cyclopropyl | OC$_2$H$_5$ | 15.0 | oil |
| 166. | 2-Cl, 6-CH$_3$ | OC$_2$H$_5$ | OCH(CH$_3$)C$_6$H$_5$ | 14.4, 14.3 | oil |
| 167. | 2-CF$_3$ | OC$_2$H$_5$ | OCH(CH$_3$)$_2$ | 13.3 | oil |
| 169. | 2-CH$_3$ | OCH(CH$_3$)$_2$ | C$_2$H$_5$ | 45.5 | oil |
| 170. | 2-CF$_3$ | OCH(CH$_3$)$_2$ | C$_2$H$_5$ | 45.3 | oil |
| 171. | 2-Cl | OCH(CH$_3$)$_2$ | C$_2$H$_5$ | 45.5 | oil |
| 172. | 2-OCF$_3$ | OCH(CH$_3$)$_2$ | C$_2$H$_5$ | 45.6 | oil |
| 173. | H | OCH(CH$_3$)$_2$ | C$_2$H$_5$ | 45.5 | oil |
| 175. | 2-NO$_2$ | OCH(CH$_3$)$_2$ | C$_2$H$_5$ | 45.2 | oil |
| 176. | 2-CH$_3$, 6-CH$_3$ | OCH(CH$_3$)$_2$ | C$_2$H$_5$ | 46.1 | oil |
| 177. | 2-Cl, 5-Cl | OCH(CH$_3$)$_2$ | C$_2$H$_5$ | 45.0 | 62-62.5 |
| 178. | 2-OCH$_3$ | OCH(CH$_3$)$_2$ | C$_2$H$_5$ | 45.2 | oil |
| 179. | 2-Cl, 6-CH(CH$_3$)$_2$ | OCH$_2$CH$_3$ | OCH(CH$_3$)$_2$ | 13.9 | oil |
| 180. | 2-Cl, 4-Cl | OCH(CH$_3$)$_2$ | CH$_2$CH$_3$ | 47.8 | oil |
| 181. | 2-Cl, 3-Cl | OCH$_2$CH$_3$ | CH$_2$CH$_3$ | 46.6 | oil |
| 183. | 2-CH(CH$_3$)$_2$ | OCH(CH$_3$)$_2$ | CH$_2$CH$_3$ | 45.6 | oil |
| 184. | 2-Cl, 6-CH(CH$_3$)$_2$ | OCH(CH$_3$)$_2$ | OCH(CH$_3$)$_2$ | 15.5 | oil |
| 185. | 2-Cl, 3-Cl | OCH(CH$_3$)$_2$ | CH$_2$CH$_3$ | 45.3 | 78-79 |
| 186. | 2-CN | OCH(CH$_3$)$_2$ | CH$_2$CH$_3$ | 45.3 | oil |
| 187. | 2-CF$_3$ | OCH(CH$_3$)$_2$ | CH$_3$ | 42.2 | 52.5-54 |
| 188. | 2-CN | OCH(CH$_3$)$_2$ | CH$_3$ | 41.8 | oil |
| 191. | 2-Cl, 6-CH(CH$_3$)$_2$ | OCH(CH$_3$)$_2$ | CH$_2$CH$_3$ | 45.8 | oil |
| 192. | 2-Cl, 6-CH(CH$_3$)$_2$ | OCH$_2$CH$_3$ | OCH$_2$CH$_3$ | 15.0 | oil |
| 193. | 2-Cl, 6-CH$_3$ | OCH(CH$_3$)$_2$ | CH$_2$CH$_2$CH$_3$ | 44.4 | 65.5-66.5 |
| 196. | 2-Cl, 6-Cl | OCH(CH$_3$)$_2$ | CH$_3$ | 42.0 | 71-72 |
| 197. | 2-Cl, 6-CH(CH$_3$)$_2$ | OCH(CH$_3$)$_2$ | CH$_3$ | 42.5 | 69.5-70.5 |
| 198. | 2-Cl | OCH(CH$_3$)$_2$ | CH$_3$ | 42.3 | 62.5-65 |
| 203. | 2-CO$_2$CH$_3$ | OCH(CH$_3$)$_2$ | CH$_3$ | 42.6 | oil |
| 206. | 2-CO$_2$CH$_3$ | OCH(CH$_3$)$_2$ | CH$_2$CH$_3$ | 45.9 | oil |
| 207. | 2-C(CH$_3$)$_3$ | OCH$_2$CH$_3$ | OCH$_2$CH$_3$ | 15.3 | oil |
| 208. | 2-C(CH$_3$)$_3$ | OCH(CH$_3$)$_2$ | CH$_2$CH$_3$ | 46.1 | oil |
| 209. | 2-CH$_3$, 6-CO$_2$CH$_2$CH$_3$ | OCH(CH$_3$)$_2$ | CH$_3$ | 42.2 | oil |
| 211. | 2-CH$_3$, 6-CO$_2$CH(CH$_3$)$_2$ | OCH(CH$_3$)$_2$ | CH$_3$ | 42.3 | 81-83.5 |
| 212. | 2-Cl, 6-CH$_3$ | OCH$_2$CH$_2$CH$_3$ | CH$_2$CH$_3$ | 47.0 | oil |
| 213. | 2-Cl, 6-CH$_3$ | O-cyclobutyl | CH$_2$CH$_3$ | 45.6 | oil |
| 214. | 2-Cl, 6-CH$_3$ | OCH(CH$_3$)CH$_2$CH$_3$ | CH$_2$CH$_3$ | 45.6, 45.8 | oil |
| 215. | 2-Cl, 6-CH(CH$_3$)$_2$ | OCH(CH$_3$)$_2$ | OCH$_3$ | 15.2 | oil |

TABLE 1A-continued

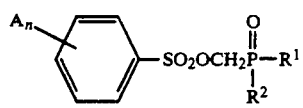

| Cpnd | A$_n$ | R$^1$ | R$^2$ | $^{31}$P-NMR | State or Melting Point °C. |
|---|---|---|---|---|---|
| 216. | 2-Cl | OCH(CH$_3$)$_2$ | OCH$_2$CH$_3$ | 13.5 | oil |
| 217. | 2-Cl | OCH(CH$_3$)$_2$ | OCH$_3$ | — | — |
| 218. | 2-CF$_3$, 6-CH$_3$ | OCH(CH$_3$)$_2$ | CH$_2$CH$_3$ | 45.5 | oil |
| 219. | 2-CF$_3$, 6-CH$_3$ | OCH(CH$_3$)$_2$ | CH$_3$ | 42.2 | oil |
| 220. | 2-CF$_3$, 6-CH$_3$ | OCH(CH$_3$)$_2$ | OCH$_2$CH$_3$ | — | — |
| 221. | 2-CF$_3$, 6-OCH$_3$ | OCH(CH$_3$)$_2$ | CH$_2$CH$_3$ | 46.0 | 95.5-98° C. |
| 222. | 2-CF$_3$, 6-OCH$_3$ | OCH(CH$_3$)$_2$ | CH$_3$ | 42.8 | oil |
| 223. | 2-CF$_3$, 6-OCH$_3$ | OCH(CH$_3$)$_2$ | OCH$_2$CH$_3$ | 14.2 | oil |
| 224. | 2-OCH$_3$, 4-CF$_3$ | OCH(CH$_3$)$_2$ | CH$_2$CH$_3$ | 45.6 | oil |
| 225. | 2-Cl, 6-CH$_3$ | OC(CH$_3$)$_3$ | CH$_2$CH$_3$ | 42.9 | 92.5-108(dec) |
| 226. | 2-Cl | OCH(CH$_3$)$_2$ | OCH(CH$_3$)$_2$ | 12.5 | 57.5-58.5 |
| 227. | 2-OCH$_3$, 4-CF$_3$ | OCH(CH$_3$)$_2$ | CH$_3$ | 42.5 | oil |
| 228. | 2-Cl, 6-CH(CH$_3$)$_2$ | OCH$_2$CH$_3$ | CH$_3$ | 44.0 | oil |
| 229. | 2-Cl, 6-CH$_3$ | OCH$_2$CH(CH$_3$)$_2$ | CH$_2$CH$_3$ | 46.9 | oil |
| 230. | 2-Cl, 6-CH$_3$ | O(CH$_2$)$_3$CH$_3$ | CH$_2$CH$_3$ | 47.2 | oil |
| 231. | 2-Br | OCH(CH$_3$)$_2$ | CH$_2$CH$_3$ | 45.7 | oil |
| 232. | 2-Cl, 6-CH$_3$ | OCH$_3$ | CH$_2$CH$_3$ | 48.8 | 68-69.5 |
| 233. | 2-Cl, 5-CH$_3$ | OCH(CH$_3$)$_2$ | CH$_2$CH$_3$ | 45.5 | 64-66 |
| 237. | 2-CF$_3$, 6-OCH$_3$ | OCH$_2$CH$_3$ | OCH$_2$CH$_3$ | 15.3 | oil |
| 239. | 2-Br, 6-Br | OCH(CH$_3$)$_2$ | CH$_2$CH$_3$ | 45.4 | oil |
| 240. | 2-Cl, 6-CH(CH$_3$)$_2$ | O(CH$_2$)$_2$CH$_3$ | CH$_3$ | 44.2 | oil |
| 241. | 2-Cl, 6-CH(CH$_3$)$_2$ | OCH$_2$CH(CH$_3$)$_2$ | CH$_3$ | 44.1 | oil |
| 243. | 2-Br, 6-Br | OCH$_2$CH$_3$ | OCH$_2$CH$_3$ | 14.5 | oil |
| 253. | 2-OCH$_2$CH$_3$, 4-CF$_3$ | OCH(CH$_3$)$_2$ | CH$_2$CH$_3$ | 45.9 | oil |
| 254. | 2-CF$_3$, 6-OCH$_2$CH$_3$ | OCH(CH$_3$)$_2$ | CH$_2$CH$_3$ | 46.0 | 99-101.5 |
| 255. | 2-CF$_3$, 6-OCH$_2$CH$_3$ | OCH(CH$_3$)$_2$ | OCH$_2$CH$_3$ | 14.2 | oil |
| 257. | 2-CF$_3$, 6-OCH$_2$CH$_3$ | OCH(CH$_3$)$_2$ | OCH(CH$_3$)$_2$ | 13.2 | oil |
| 258. | 2-Cl, 5-Cl | OCH(CH$_3$)$_2$ | OCH$_3$ | 14.5 | 53-54 |
| 259. | 2-Cl, 5-Cl | OCH(CH$_3$)$_2$ | OCH$_2$CH$_3$ | 13.2 | 51-52 |

TABLE 1B

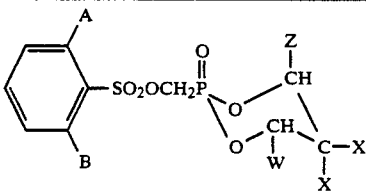

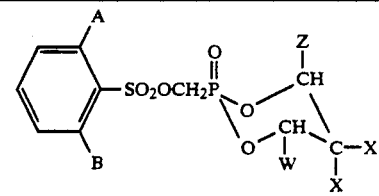

| Cpnd. | A | B | W | X | Z | Isomer | $^{31}$P-NMR | State or Melting Point °C. |
|---|---|---|---|---|---|---|---|---|
| 139. | Cl | CH$_3$ | CH$_3$ | H | H | 1 | 5.8 | 113-114 |
| 140. | Cl | CH$_3$ | CH$_3$ | H | H | 2 | 9.9 | 76.5-78 |
| 144. | CF$_3$ | H | CH$_3$ | H | H | 1 | 4.9 | wax |
| 145. | CF$_3$ | H | CH$_3$ | H | H | 2 | 8.8 | oil |
| 148. | Cl | CH$_3$ | H | CH$_3$ | H | — | 6.5 | 118-118.5 |
| 149. | Cl | CH$_3$ | H | H | H | — | 7.0 | 89-90 |
| 150. | Cl | CH$_3$ | CH$_3$ | H | CH$_3$ | 1 | 5.7 | 118.5-120 |
| 151. | CF$_3$ | H | H | CH$_3$ | H | — | 5.5 | 114-117 |
| 152. | Cl | CH$_3$ | CH$_3$ | H | CH$_3$ | 2 | 8.3 | 75-76 |
| 155. | CF$_3$ | H | CH$_3$ | H | CH$_3$ | 1 | 5.3 | 102-104 |
| 156. | CF$_3$ | H | CH$_3$ | H | CH$_3$ | mixture | 8.6, 5.2 | 86-91 |

TABLE 1C

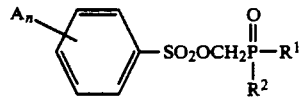

| Cpnd. | A$_n$ | R$^1$ | R$^2$ | $^{31}$P-NMR | State or Melting Point °C. |
|---|---|---|---|---|---|
| 10. | 2-Cl, 4-Cl, 5-Cl | OC$_2$H$_5$ | OC$_2$H$_5$ | 14.2 | wax |
| 50. | 2-OCOCH$_3$, 3-Cl, 5-Cl | OC$_2$H$_5$ | OC$_2$H$_5$ | 14.3 | oil |
| 59. | 2-Cl, 4-Cl, 5-CH$_3$ | OC$_2$H$_5$ | OC$_2$H$_5$ | 14.5 | oil |

TABLE 1C-continued

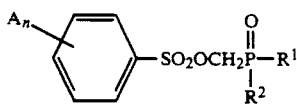

| Cpnd. | $A_n$ | $R^1$ | $R^2$ | $^{31}$P-NMR | State or Melting Point °C. |
|---|---|---|---|---|---|
| 66. | 2-Cl, 5-CH$_3$, 6-Cl | OC$_2$H$_5$ | OC$_2$H$_5$ | 14.6 | 52–54 |
| 69. | 2-CH$_3$, 4-CH$_3$, 6-CH$_3$ | OC$_2$H$_5$ | OC$_2$H$_5$ | 15.7 | oil |
| 84. | 2-F, 3-F, 4-F, 5-F, 6-F | OC$_2$H$_5$ | OC$_2$H$_5$ | 13.8 | 44.5–45 |
| 112. | 2-Cl, 4-Cl, 6-Cl | OC$_2$H$_5$ | OC$_2$H$_5$ | 14.3 | oil |
| 118. | 2-CH(CH$_3$)$_2$, 4-CH(CH$_3$)$_2$, 6-CH(CH$_3$)$_2$ | OC$_2$H$_5$ | OC$_2$H$_5$ | 15.9 | 64–65 |
| 124. | 2-OCH$_3$, 3-Cl, 6-OCH$_3$ | OC$_2$H$_5$ | OC$_2$H$_5$ | 15.5 | oil |
| 131. | 2-CH$_3$, 4-Cl, 6-CH$_3$ | OCH(CH$_3$)$_2$ | OCH(CH$_3$)$_2$ | 13.2 | oil |
| 133. | 2-CH$_3$, 4-Cl, 6-CH$_3$ | OCH$_3$ | OCH(CH$_3$)$_2$ | 15.6 | oil |
| 134. | 2-Cl, 4-Cl, 6-CH$_3$ | OCH(CH$_3$)$_2$ | OCH(CH$_3$)$_2$ | 12.7 | oil |
| 135. | 2-Cl, 4-Cl, 6-CH$_3$ | OCH$_3$ | OCH(CH$_3$)$_2$ | 15.0 | oil |
| 137. | 2-Cl, 4-Cl, 6-OCH$_3$ | OCH(CH$_3$)$_2$ | OCH(CH$_3$)$_2$ | 13.0 | oil |
| 138. | 2-Cl, 4-Cl, 6-OCH$_3$ | OCH$_3$ | OCH(CH$_3$)$_2$ | 15.4 | oil |
| 146. | 2-Cl, 3-CH$_3$, 5-Cl, 6-CH$_3$ | OCH(CH$_3$)$_2$ | OCH(CH$_3$)$_2$ | 12.7 | oil |
| 147. | 2-Cl, 3-CH$_3$, 5-Cl, 6-CH$_3$ | OCH$_3$ | OCH(CH$_3$)$_2$ | 15.1 | oil |
| 160. | 2-CH$_3$, 3-CH$_3$, 6-NO$_2$ | OC$_2$H$_5$ | OC$_2$H$_5$ | 14.6 | oil |
| 182. | 2-CH$_3$, 4-CH$_3$, 6-CH$_3$ | OCH(CH$_3$)$_2$ | CH$_2$CH$_3$ | 46.0 | oil |
| 189. | 2-Cl, 4-Cl, 5-CH$_3$ | OCH(CH$_3$)$_2$ | CH$_2$CH$_3$ | 45.5 | 68.5–69 |
| 190. | 2-Cl, 4-Cl, 6-Cl | OCH(CH$_3$)$_2$ | CH$_2$CH$_3$ | 45.1 | 70–70.5 |
| 194. | 2-Cl, 3-CH$_3$, 6-Cl | OCH(CH$_3$)$_2$ | CH$_2$CH$_3$ | 45.5 | 59–60 |
| 195. | 2-Cl, 3-Cl, 4-Cl | OCH(CH$_3$)$_2$ | CH$_2$CH$_3$ | 45.1 | 95.5–97.5 |
| 199. | 2-Cl, 3-CH$_3$, 6-Cl | OCH(CH$_3$)$_2$ | CH$_3$ | 42.2 | 60–62 |
| 202. | 2-Cl, 3-CH$_3$, 5-Cl, 6-CH$_3$ | OCH(CH$_3$)$_2$ | CH$_2$CH$_3$ | 45.6 | 68–69 |
| 204. | 2-CH(CH$_3$)$_2$, 4-CH(CH$_3$)$_2$, 6-CH(CH$_3$)$_2$ | OCH(CH$_3$)$_2$ | CH$_2$CH$_3$ | 46.5 | oil |
| 205. | 2-CH$_3$, 3-Cl, 4-Cl | OCH$_2$CH$_3$ | OCH$_2$CH$_3$ | 14.9 | oil |
| 210. | 2-Cl, 3-Cl, 4-Cl | OCH$_2$CH$_3$ | OCH$_2$CH$_3$ | 14.3 | oil |

TABLE 1D

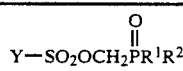

| Cpnd. | Y | $R^1$ | $R^2$ | $^{31}$P NMR | State or Melting Point °C. |
|---|---|---|---|---|---|
| 11. | 2-thienyl | OCH$_2$CH$_3$ | OCH$_2$CH$_3$ | 14.7 | oil |
| 18. | 5-chloro-2-thienyl | OCH$_2$CH$_3$ | OCH$_2$CH$_3$ | 14.5 | oil |
| 20. | 1,3-dimethyl-5-chloro-4-pyrazolyl | OCH$_2$CH$_3$ | OCH$_2$CH$_3$ | 15.2 | oil |
| 23. | benzyl | OCH$_2$CH$_3$ | OCH$_2$CH$_3$ | 15.5 | oil |
| 29. | 3,5-dimethyl-4-isoxazolyl | OCH$_2$CH$_3$ | OCH$_2$CH$_3$ | 14.9 | oil |
| 36. | 8-quinolinyl | OCH$_2$CH$_3$ | OCH$_2$CH$_3$ | 17.2 | oil |
| 40. | 2,3-dibromo-5-thienyl | OCH$_2$CH$_3$ | OCH$_2$CH$_3$ | 14.2 | wax |
| 41. | 2,5-dichloro-3-thienyl | OCH$_2$CH$_3$ | OCH$_2$CH$_3$ | 14.5 | oil |
| 42. | 2,5-dichloro-4-bromo-3-thienyl | OCH$_2$CH$_3$ | OCH$_2$CH$_3$ | 14.2 | 62–64 |
| 48. | 1-naphthyl | OCH$_2$CH$_3$ | OCH$_2$CH$_3$ | 14.9 | 58–59 |
| 51. | 2-naphthyl | OCH$_2$CH$_3$ | OCH$_2$CH$_3$ | 15.1 | oil |
| 67. | 1-(N,N-diethylcarbamoyl)-1,2,4-triazol-3-yl | OCH$_2$CH$_3$ | OCH$_2$CH$_3$ | 14.0 | 66–69 |
| 110. | cyclohexyl | OCH$_2$CH$_3$ | OCH$_2$CH$_3$ | 16.0 | oil |
| 136. | 3-(diethylphosphonoylmethyloxysulfonyl)-2,4-6-trimethylphenyl | OCH$_2$CH$_3$ | OCH$_2$CH$_3$ | 15.1 | 121–121.5 |
| 200. | 2,5-dichloro-3-thienyl | OCH(CH$_3$)$_2$ | CH$_2$CH$_3$ | 45.1 | 40.5–42 |
| 201. | 1,3-dimethyl-5-chloro-4-pyrazolyl | OCH(CH$_3$)$_2$ | CH$_2$CH$_3$ | 45.7 | 100.5–101 |
| 234. | 1,3-dimethyl-3-trifluoromethyl-4-pyrazolyl | OCH(CH$_3$)$_2$ | CH$_2$CH$_3$ | 45.0 | 81–84 |
| 235. | 1,3,5-trimethyl-4-pyrazolyl | OCH(CH$_3$)$_2$ | CH$_2$CH$_3$ | 46.3 | 106.5–108.5 |
| 236. | 3,5-dimethyl-4-isoxazolyl | OCH(CH$_3$)$_2$ | CH$_2$CH$_3$ | 45.1 | 57–58.5 |
| 238. | 1,5-dimethyl-3-trifluoromethyl-4-pyrazolyl | OCH$_2$CH$_3$ | OCH$_2$CH$_3$ | 14.8 | 74–77 |
| 242. | 2,4-dimethyl-5-thiazolyl | OCH(CH$_3$)$_2$ | CH$_2$CH$_3$ | 45.2 | oil |
| 244. | 2,5-dichloro-4-methyl-3-thienyl | OCH$_2$CH$_3$ | OCH$_2$CH$_3$ | 14.8 | oil |
| 245. | 2,5-dichloro-4-methyl-3-thienyl | OCH(CH$_3$)$_2$ | CH$_2$CH$_3$ | 45.3 | 52–54 |
| 246. | 2,5-dichloro-4-methyl-3-thienyl | OCH(CH$_3$)$_2$ | CH$_3$ | 41.9 | 80.5–82 |
| 247. | 2,5-dichloro-4-methyl-3-thienyl | OCH(CH$_3$)$_2$ | OCH$_2$CH$_3$ | 13.6 | 67–68 |
| 248. | 8-chloro-1-naphthyl | OCH(CH$_3$)$_2$ | CH$_2$CH$_3$ | 46.3 | 87.5–88.5 |
| 249. | 4-benzo-2,1,3-thiadiazolyl | OCH(CH$_3$)$_2$ | CH$_2$CH$_3$ | 45.7 | oil |
| 250. | 2,4-dimethyl-5-thiazolyl | OCH$_2$CH$_3$ | OCH$_2$CH$_3$ | — | oil |
| 251. | 5-chloro-1-methyl-3-isopropyl-4-pyrazolyl | OCH(CH$_3$)$_2$ | CH$_2$CH$_3$ | 45.9 | oil |

TABLE 1D-continued $$Y-SO_2OCH_2\overset{O}{\overset{\|}{P}}R^1R^2$$

| Cpnd. | Y | $R^1$ | $R^2$ | $^{31}P$ NMR | State or Melting Point °C. |
|---|---|---|---|---|---|
| 252. | 5-chloro-1,3-dimethyl-4-pyrazolyl | OCH(CH$_3$)$_2$ | CH$_3$ | 42.5 | 107–108.5 |
| 256. | 5-chloro-3-ethyl-1-methyl-4-pyrazolyl | OCH(CH$_3$)$_2$ | CH$_2$CH$_3$ | 45.8 | 69–70.5 |

TABLE 1E

| Cpnd. | | $^{31}$P-NMR | State |
|---|---|---|---|
| 168. | 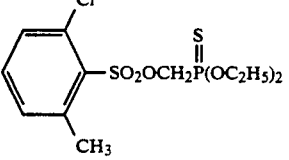 | 80.0 | oil |
| 174. | 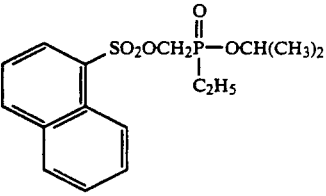 | 45.7 | oil |

PREPARATION OF SULFONYL CHLORIDE INTERMEDIATES OF FORMULA II

EXAMPLE 1

2-Methyl-6-(trifluoromethyl)benzenesulfonyl chloride

A: 2-{(Methylthio)methyl}-6-(trifluoromethyl)aniline

Dimethylsulfide, 16 ml, was syringed all at once into a solution of 25.0 grams (g) of 2-(trifluoromethyl)aniline in 400 milliliters (ml) of methylene chloride. The reaction solution was cooled to 15° C. and 29.0 g of N-chlorosuccinimide was added in small portions over a 20 minute period at such a rate that the reaction temperature did not exceed 20° C. The reaction mixture was stirred at 15° C. for 15 minutes, then 30.4 ml of triethylamine was added dropwise over 15 minutes at such a rate that the temperature did not exceed 15° C. After an additional five minutes of stirring, the reaction was refluxed overnight, allowed to cool to room temperature, washed with two 200 ml portions of 10% sodium hydroxide, the organic phase separated, dried with magnesium sulfate and filtered. The remainder of the solvent was distilled off to yield 35.8 g of the crude desired product which was used without any additional purification in subsequent reactions.

B: 2-Methyl-6-(trifluoromethyl)aniline

Several scoops of Raney nickel were added to 28.6 g of 2-{(methylthio)methyl}-6-(trifluoromethyl)aniline (Example 1A) in 50 ml of absolute ethanol. The reaction slurry was stirred at room temperature and the progress of the reaction was followed by gas-liquid chromatography (GLC). Periodically, additional Raney nickel was added to the reaction slurry. The reaction was allowed to stir overnight. Most but not all of the starting material had reacted. The Raney nickel was removed by filtration, the filter cake rinsed with 1200 ml of absolute ethanol and the filtrate concentrated. The concentrate was dissolved in 100 ml of ethyl acetate, washed with 70 ml of water, dried with magnesium sulfate, filtered, and concentrated to yield 19.2 g of the crude product as a yellow oil which was distilled at 30–40 torr, to give 6.2 g of the desired product at 93°–108° C. in 80% purity.

C: 2-Methyl-6-(trifluoromethyl)benzenesulfonyl chloride

A slurry of 6.2 g of 2-methyl-6-(trifluoromethyl)aniline, (from 1B), 30 ml. of concentrated hydrochloric acid and 30 ml of water was cooled to −15° C. and a solution of 2.76 g of sodium nitrite dissolved in 8 ml of water was added dropwise over ten minutes at such a rate that the reaction temperature was kept between −17° C. and −13° C. After the addition was complete, the resulting diazonium salt solution was cooled to −30° C. and held near that temperature until used. Meanwhile, a solution of sulfur dioxide in glacial acetic acid was prepared by bubbling sulfur dioxide for 20 minutes through a gas dispersion tube into 50 ml of glacial acetic acid. Copper (I) chloride, 0.5 g, was added to the solution and the flow of sulfur dioxide gas was continued for an additional 20 minutes. The flow of gas was then stopped, the resulting sulfur dioxide, copper (I) chloride and acetic acid solution was cooled to 10° C., and the cold diazonium salt solution, prepared previously, was added in 15 ml portions. The total time for addition was five minutes and some foaming occurred after each addition of the diazonium salt solution. When the additions were complete, the reaction was allowed to warm to room temperature, held for 2 hours, and then poured onto 300 g of ice. After the ice melted the aqueous mixture was extracted with 200 ml of ether, the ether extract washed with 75 ml of saturated sodium bicarbonate solution, dried with magnesium sulfate, filtered and concentrated to yield a yellow liquid. After drying at 50° C. in a vacuum oven overnight, 6.5 g of the desired sulfonyl chloride was obtained as a purple liquid. Using the procedure described in Example 1C, the following sulfonyl chlorides of Formula II were prepared from the indicated anilines:

2-cyanobenzenesulfonyl chloride from 2-cyanoaniline;
2-nitro-4-methylbenzenesulfonyl chloride from 2-nitro-4-methylaniline;
2-methyl-5-chlorobenzenesulfonyl chloride from 2-methyl-5-chloroaniline;
2-chloro-5-methylbenzenesulfonyl chloride from 2-chloro-5-methylaniline;
2-nitro-4-methoxybenzenesulfonyl chloride from 2-nitro-4-methoxyaniline;
2,6-dichloro-3-methylbenzenesulfonyl chloride from 2,6-dichloro-3-methylaniline;
2-methyl-6-nitrobenzenesulfonyl chloride from 2-methyl-6-nitroaniline;

2,4-dichloro-6-methylbenzenesulfonyl chloride from 2,4-dichloro-6-methylaniline;

2,3-dimethyl-6-nitrobenzenesulfonyl chloride from 2,3-dimethyl-6-nitroaniline;

2-methyl-6-(ethoxycarbonyl)benzenesulfonyl chloride from 2-methyl-6-(ethoxycarbonyl)aniline; and 2-methyl-6-(isopropyloxycarbonyl)benzenesulfonyl chloride from 2-methyl-6-(isopropyloxycarbonyl)aniline.

2,6-dibromobenzenesulfonyl chloride from 2,6-dibromoaniline.

EXAMPLE 2

2-Methoxy-6-(trifluoromethyl)benzenesulfonyl chloride and 2-Methoxy-4-(trifluoromethyl)benzenesulfonyl chloride To a solution of 25.0 g of 3-(trifluoromethyl)anisole in 120 ml of dry tetrahydrofuran (THF) at −70° C. was added dropwise 112 ml of a n-butyl lithium solution (1.6M in hexane) during a 60 minute period. After the addition of the n-butyl lithium solution was complete the reaction was allowed to warm to room temperature. A precipitate of lithio-3-(trifluoromethyl)anisole began to form at −20° C.

Concurrently, sulfur dioxide gas was bubbled into 150 ml of dry THF for 45 minutes and the resulting solution cooled to −70° C.

The lithio-3-(trifluoromethyl)anisole solution was cooled to −70° C. and subsequently added dropwise over 90 minutes to the sulfur dioxide and THF solution. No significant exotherm occurred. The resulting reaction mixture was slowly allowed to warm to room temperature and stirred overnight. As the solution warmed it began to darken. Upon standing a white solid phase (the lithium salt of the sulfinic acid) separated from the black THF phase. Most of the THF was decanted off, then 50 ml of methylene chloride was added and the reaction slurry was cooled to 8° C. Fourteen ml of sulfuryl chloride was diluted with 20 ml of methylene chloride and the resulting solution added dropwise over 20 minutes to the lithium sulfinate slurry. The addition caused the reaction to exotherm to 13° C. After 75% of the sulfuryl chloride solution was added, the addition was halted since the reaction had become mostly homogeneous. The reaction solution was concentrated, the residual material partitioned between 200 ml of ethyl acetate and 80 ml of water, the organic phase dried with magnesium sulfate, filtered and concentrated to yield 17.9 g of a waxy yellow solid containing two major components in an 82:18 ratio by GLC.

Using the procedure described above, a mixture of 2,6-dimethoxybenzenesulfonyl chloride and 3-chloro-2,6-dimethoxybenzenesulfonyl chloride, which results from ring chlorination of the 2,6-dimethoxybenzenesulfonyl chloride by sulfuryl chloride, was prepared from 1,3-dimethoxybenzene.

EXAMPLE 3

2-(Difluoromethoxy)-6-methylbenzenesulfuryl chloride

A: 2-(Difluoromethoxy)-6-methyl-nitrobenzene

To a mixture of 43.0 g of 3-methyl-2-nitrophenol, 250 ml of p-dioxane, 150 ml of water, and 75 ml of 50% sodium hydroxide solution at 70° C. was added gaseous difluorochloromethane at a steady rate. The pH of the reaction was checked periodically. If the pH became acidic, 30 to 40 ml of 50% sodium hydroxide solution was added. After six hours of heating, the flow of the difluorochloromethane was halted and the reaction allowed to cool to room temperature. After standing overnight the reaction solution was poured onto a mixture of 50 g of ice and 250 ml of water and extracted with two 450 ml portions of ethyl acetate. The organic phase was dried with magnesium sulfate, filtered and concentrated. The resulting brown liquid was dried in a vacuum oven at 45° C. overnight to yield 53.3 g of the desired intermediate.

B: 2-(Difluoromethoxy)-6-Methylaniline

A mixture of 400 ml of absolute ethanol, 50 ml of water, 72.6 g of zinc dust, 53.3 g of the 2-(difluoromethoxy)-6-methylnitrobenzene, (Example 3A), and a solution of 20.0 g of calcium chloride dissolved in 60 ml of water was refluxed for three hours, allowed to stand overnight, refluxed for an additional hour, and then an additional 43 g of zinc dust and a solution of 18 g of calcium chloride dissolved in 50 ml of water was added. Refluxing for an additional three hours was required to drive the reaction to completion. The reaction was vacuum filtered through Celite ®, the filter cake rinsed with 300 ml of ethanol and the filtrate concentrated to a volume of 100 ml. The liquid was diluted with 300 ml of ethyl acetate, 80 ml of 10% sodium hydroxide solution and 100 ml of water. A precipitate formed which was removed by vacuum filtration through Celite. The filter cake was rinsed with 200 ml of ethyl acetate. The phases were separated and the organic phase was dried with sodium sulfate, filtered and concentrated to yield 25.8 g of the desired intermediate as a black oil.

C: 2-(Difluoromethoxy)-6-methylphenyl-disulfide

Preparation of the disodium disulfide solution:

A slurry of 5.44 g of sulfur, 150 ml of water and 39.6 g of sodium sulfide nonahydrate was heated to boiling briefly and then allowed to cool to room temperature. Then, 60 g of a 50% sodium hydroxide solution was added.

Preparation of the diazonium salt solution:

2-(Difluoromethoxy)-6-methylaniline, prepared in Example 3B, 25.8 g, was added in small portions over 10 minutes to a solution of 45 ml of concentrated hydrochloric acid in 50 ml of water. The reaction slurry was cooled to 5° C. and a solution of 11.4 g of sodium nitrite dissolved in 30 ml of water was added dropwise over a 40 minute period at such a rate that the reaction slurry did not exceed 8° C. The diazonium salt solution was kept below 8° C. until used.

Preparation of the disulfide:

The disodium disulfide solution was cooled to 8° C. and the cooled diazonium salt solution was added in 20 to 30 ml portions over a 30 minute period. After each addition there was considerable foaming. After the addition of the diazonium salt solution was complete, the reaction was allowed to warm to room temperature. After stirring at room temperature for an additional 2.5 hours, 250 ml of ether was added and the two phases were allowed to stand at room temperature overnight.

The two phases were separated, the aqueous phase extracted with 250 ml of ether, the organic phases combined, dried with magnesium sulfate, filtered and concentrated to yield 14.8 g of the crude desired intermediate as a black oil which solidified upon standing.

D: 2-(Difluoromethoxy)-6-methylbenzenesulfonyl chloride

Chlorine gas was bubbled for 10 minutes through a reaction mixture at 12°-15° C. of 90 ml of 10% aqueous hydrochloric acid solution, 70 ml of water, 50 ml of acetic acid and 14.8 g of the crude 2-(difluoromethoxy)-6-methylphenyldisulfide, (Example 3C). The reaction slurry was extracted with two 150 ml portions of ether, the ether extracts combined, dried with magnesium sulfate, filtered, and concentrated to yield 17.7 g of the crude desired sulfonyl chloride as a black oil.

Using the procedures described in Examples 3C and 3D,
2,6-diethylbenzenesulfonyl chloride was prepared from 2,6-diethylaniline.

EXAMPLE 4

2-Isopropylbenzenesulfonyl chloride

2-Isopropylthiophenol, 20.0 g, was added to 200 ml of 10% aqueous hydrochloric acid solution and 50 ml of water and the resulting two phase system stirred vigorously and cooled to 5° C. Chlorine gas was then bubbled through the reaction mixture for two hours at such a rate that the reaction temperature was kept between 0° C. and 5° C. The reaction solution was extracted with ether (2×150 ml), the ether extracts combined, washed with 100 ml of saturated sodium bicarbonate solution, dried over anhydrous magnesium sulfate, filtered, and concentrated to yield 26.5 of the desired sulfonyl chloride as a black oil. Using the procedure described above, the following sulfonyl chlorides of Formula II were prepared from the indicated compounds:

2-methylbenzenesulfonyl chloride from 2-methylthiophenol; cyclohexylsulfonyl chloride from dicyclohexyl disulfide;
2,6-dimethylbenzenesulfonyl chloride from 2,6-dimethylthiophenol; 2-t-butylbenzenesulfonyl chloride from 2-t-butylthiophenol (prepared using the method disclosed in J. Org. Chem. 31 1966 pp. 3980); and
2-chloro-6-nitrobenzenesulfonyl chloride from 2-chloro-6-nitrobenzenethiol (Example 6).

A mixture of 2-methoxybenzenesulfonyl chloride and 5-chloro-2-methoxybenzenesulfonyl chloride, which results from ring chlorination, was prepared from 2-methoxythiophenol.

EXAMPLE 5

2,6-Dimethyl-4-chlorophenylsulfonyl chloride

A: 3,5-Dimethylchlorobenzene

A total of 33.0 g of 3,5-dimethylaniline was added dropwise over 20 minutes to 200 ml of concentrated hydrochloric acid at such a rate that the temperature of the reaction was kept below 35° C. After several minutes of vigorous stirring, the reaction was cooled to −10° C. A solution of 19.7 g of sodium nitrite dissolved in 50 ml of water was added dropwise over 30 minutes at such a rate that the reaction temperature was kept between −12° C. to −16° C. Then, 3.0 g of copper (I) chloride was added and the reaction was warmed to 27° C. At this temperature foaming was noted and the reaction temperature was maintained below 35° C. with an ice water bath. After one hour, the reaction was poured onto 350 g of ice. Once the ice melted the crude product was extracted with 400 ml of hexanes, the organic phase was dried with magnesium sulfate, filtered, and concentrated to yield 20.2 g of a liquid. This material was diluted with 5 ml of hexanes and chromatographed on neutral alumina (Brockman 1, 150 mesh), eluting with 1200 ml of hexanes and collecting 200 ml fractions. The desired 95% pure intermediate, 10.1 g, was isolated cleanly in fractions 1 and 2.

B: 2,6-Dimethyl-4-chlorophenylsulfonyl chloride

To 16.7 ml of chlorosulfonic acid at 10° C. was added 10.1 g of 3,5-dimethylchlorobenzene, (Example 5A), dropwise over a 10 minute period. The reaction was allowed to stir at about 10° C. for 90 minutes and then allowed to warm to room temperature and stirred overnight. The reaction was poured onto 150 g of ice, the solid that formed collected on a fritted glass funnel and dissolved in 150 ml of methylene chloride. The methylene chloride solution was washed with 70 ml of saturated sodium bicarbonate solution, dried with magnesium sulfate, filtered and concentrated to yield 13.5 g of the desired sulfonyl chloride. Using the procedure described in Example 5B, the following sulfonyl chlorides of Formula II were prepared from the indicated compounds:

2,4-dichloro-6-methoxybenzenesulfonyl chloride from 2,4-dichloroanisole and 2,5-dichloro-3,6-dimethylbenzenesulfonyl chloride from 2,5-dichloro-p-xylene.

EXAMPLE 6

2-Chloro-6-nitrobenzenethiol

Twenty grams of 2,3-dichloronitrobenzene was dissolved in 200 ml of absolute ethanol and the resulting solution added dropwise over three hours to a mixture of 40.0 g of sodium sulfide hydrate in 225 ml of absolute ethanol. The reaction temperature did not exceed 30° C. during the addition. The reaction was allowed to stir for 48 hours at room temperature. Since some of the 2,3-dichloronitrobenzene was still present, as indicated by GLC, an additional 9.0 g of the sodium sulfide hydrate was added at once and the reaction was allowed to stir overnight at room temperature. The ethanol was removed and the concentrate was partitioned between 300 ml of water and 250 ml of ether, the ether extract was discarded, and the aqueous phase made acidic by the dropwise addition of 50 ml of concentrated hydrochloric acid with the evolved gas being scrubbed through a bleach trap. A large amount of solid formed. Water, 100 ml, was added and the aqueous phase extracted with 350 ml of methylene chloride. The organic phase was dried with magnesium sulfate, filtered and concentrated to yield 11.8 g of a tan solid.

EXAMPLE 7

2-Acetoxy-3,5-dichlorobenzenesulfonyl chloride

A pyridine solution (1.1 g of pyridine in 10 ml of methylene chloride) was added dropwise over 30 minutes to a solution of 3.37 g of 3,5-dichloro-2-hydroxybenzenesulfonyl chloride, 25 ml of methylene chloride and 1.1 g of acetyl chloride. After two hours of stirring at room temperature the starting sulfonyl chloride was no longer present and one major product had formed. The reaction was concentrated and used immediately.

EXAMPLE 8

4-Methyl-3-nitrobenzenesulfonyl chloride

A: 4-Methyl-3-nitrobenzenesulfonic acid, sodium salt

A solution of 25.0 g of 4-toluenesulfonic acid and 95 ml of concentrated nitric acid was heated on a steam bath for 30 minutes during which time the solution turned deep red and gas was evolved. The reaction was allowed to cool to room temperature, poured into 250 ml of water and concentrated. An additional 30 ml of water was added and the solution again concentrated. This procedure was repeated three additional times. The resulting oil was dissolved in 30 ml of water and neutralized with the addition of 11.04 g of sodium bicarbonate. After the bubbling stopped the solution was concentrated to yield a white powder which was triturated with 300 ml of isopropanol, isolated via vacuum filtration and air dried to yield 28.9 g of the desired 4-methyl-3-nitrobenzenesulfonic acid, sodium salt.

B: 4-Methyl-3-nitrobenzenesulfonyl chloride

Two ml of dimethyl formamide (DMF) was added to a mixture of 20.0 g of 4-methyl-3-nitrobenzenesulfonic acid, sodium salt, 150 ml of chloroform and 19.9 g of thionyl chloride. Some hydrogen chloride was evolved. The reaction was heated to reflux; after one hour no hydrogen chloride was detected using wet pH paper. An additional 5 ml of DMF was added and immediate evolution of gas was noted. Heating was continued for an additional two hours. An additional two ml of DMF was added and the reaction was refluxed overnight. The reaction was allowed to cool, filtered and concentrated under reduced pressure. High vacuum was pulled on the sample with gentle heating. Yield was 18.8 g of the desired sulfonyl chloride isolated as a brown oil.

EXAMPLE 9

2-Chloro-6-isopropylbenzenesulfonyl chloride

To a stirred solution containing 22 ml of concentrated $H_2SO_4$, 20 ml of glacial acetic acid, 50 ml of concentrated HCl, and 100 ml of water was added dropwise over 40 minutes, a solution of 28.6 g of 2-chloro-6-isopropylaniline in 25 ml of glacial acetic acid. The resulting suspension was cooled to 5° C. with an ice bath and an aqueous solution of sodium nitrite (12.4 g in 30 ml of water) was added dropwise at such a rate that the temperature did not exceed 10° C. (50 minutes). The clear orange diazonium solution was kept below 10° C. until used. Meanwhile, a solution of sulfur dioxide in glacial acetic acid was prepared by bubbling sulfur dioxide through 130 ml of glacial acetic acid for 30 minutes. A slight exotherm to 35° C. was observed. The flow of sulfur dioxide was stopped so that 3.5 g of copper (I) chloride could be added and the flow was resumed for an additional 50 minutes. The gas flow was then stopped and the resulting green solution was cooled to 20° C.

The diazonium solution was then added in 40 ml portions to the sulfur dioxide/copper(I) chloride/acetic acid solution, during which time slow gas evolution was observed. With each addition of the diazonium solution the reaction mixture turned black and then slowly lightened to a green color. After all of the reagents were combined, the resulting mixture was warmed to room temperature and stirred for 3 hours, then heated to 40° C. for 30 minutes and 50° C. for 30 minutes to assure completion of reaction. The reaction mixture was then poured onto 450 g of ice and extracted with 300 ml of ether followed by 150 ml of ether. The combined ether phases were carefully washed with saturated sodium bicarbonate, 200 ml, dried with magnesium sulfate overnight, filtered and concentrated. Toluene, 100 ml, was added to the residue and the solution was reconcentrated under reduced pressure, in order to remove remaining acetic acid. The desired sulfonyl chloride was obtained as a black oil, 29.4 g (88% pure by GLC).

Using the procedure described in Example 9, the following sulfonyl chlorides of Formula II were prepared from the indicated anilines: 2,6-dichloro-3-methylsulfonyl chloride from 2,6-dichloro-3-methylaniline.

PREPARATION OF THE PHOSPHITE, PHOSPHONITE AND PHOSPHINE OXIDE INTERMEDIATES OF FORMULA IV

EXAMPLE 10

Diisopropyl phosphite

To a mixture of 78.7 g of isopropanol, 69.0 g of pyridine, and 220 ml of methylene chloride at 10° C. was added a solution of 60.0 g of phosphorus trichloride diluted with 50 ml of methylene chloride dropwise over 75 minutes. Thirty minutes after the addition was complete, the reaction mixture was allowed to stir for an additional thirty minutes while warming, heated to reflux for five hours, then allowed to cool to room temperature and stand overnight. A four ml aliquot of the reaction mixture was concentrated and analyzed by phosphorus NMR which indicated that the reaction was complete. The reaction mixture was gravity filtered, concentrated, the concentrate triturated with 250 ml of ether, gravity filtered and the filtrate concentrated to yield 68.7 g of the desired phosphite as a clear liquid.

Using the procedure described above, the following phosphites of Formula IV were prepared by reacting phosphorus trichloride with the indicated alcohol: diallyl phosphite from allyl alcohol; di-n-propyl phosphite from n-propanol; and bis-(2-chloroethyl) phosphite from 2-chloroethanol.

EXAMPLE 11

O-Isopropyl O-methylphosphite

A solution of 2.0 g of phosphorus trichloride in 20 ml of methylene chloride was cooled to 0 C. To this was slowly added a solution of 0.88 g of isopropanol in 10 ml methylene chloride, and the mixture was stirred for 5 minutes. Then, a solution of 1.15 g of pyridine in 10 ml of methylene chloride was added and the mixture was stirred for 1 hour. A solution of 1.03 g of methanol and 1.09 g of pyridine in 10 ml of methylene chloride was prepared and added slowly to the reaction mixture. The mixture was heated to reflux (40 C.) for four hours, cooled and filtered. The filtrate was concentrated to yield 1.9 g of product, as a mixture containing 71% of the desired mixed-ester product.

EXAMPLE 12

Diethyl thiophosphite

Triethylamine, 22.4 ml, was added at once to a solution of 100 ml of dry diethyl ether and 25.0 g of diethyl chlorophosphite at −30° C. The reaction warmed to −23° C. The reaction was allowed to warm to 10° C. and a flow of hydrogen sulfide was started. Little gas was consumed by the reaction, so the reaction slurry was allowed to warm and the rate of hydrogen sulfide consumption increased. The reaction temperature was kept between 23° C. and 28° C. for the remainder of the hydrogen sulfide addition, the total time for which was 150 minutes. The flow of hydrogen sulfide was stopped and the reaction set-up was swept with nitrogen. Ether, 40 ml, was added and then most of the ether was removed by atmospheric distillation. Eighty ml of ether was then added and again removed by atmospheric distillation. An additional 80 ml of ether was added and the insolubles were removed by gravity filtration. The ether filtrate was concentrated to yield 15.6 g of the desired thiophosphite as a yellow oil.

EXAMPLE 13

2-Oxo-4-methyl-1,3,2-dioxaphosphorinan

A: 2-Chloro-4-methyl-1,3,2-dioxaphosphorinan

To 300 ml of ether at 5° C. were added concurrently a solution of 32.8 g of 1,3-butanediol and 102 ml of triethylamine in 120 ml of ether and another solution of 32 ml of phosphorous trichloride in 125 ml of ether. The addition rates were adjusted to maintain a 1:1 ratio of diol to phosphorous trichloride and keep the reaction temperature below 20° C. Total time for the additions was 135 minutes. The reaction was allowed to stir for an additional 30 minutes after which the triethylamine hydrochloride salt was removed via vacuum filtration. The filter cake was rinsed with 1300 ml of ether and the combined filtrates were concentrated to yield 40.2 g of the crude intermediate. Phosphorus NMR indicated two major components in a 2:1 ratio with the major component being the desired product and the other component being the hydrolyzed product (2-oxo-4-methyl-1,3,2-dioxaphosphorinan).

B: 2-Oxo-4-methyl-1,3,2-dioxaphosphorinan

Toluene, 200 ml and 40.0 of crude 2-chloro-4-methyl-1,3,2-dioxaphosphorinan (Example 13A). were cooled with an ice water bath and then a solution of 10 ml of THF, 2.62 g of triethylamine, and 4.66 g of water was added dropwise over 40 minutes. The reaction was allowed to stir for an additional 30 minutes and then the cooling bath was removed. After stirring for an additional 30 minutes, the reaction was filtered, the filter cake rinsed with ethyl acetate and the combined filtrates concentrated to yield 23.5 g of the desired dioxaphosphorinan.

Using the procedures described above, the following phosphorinans of Formula IV were prepared from the indicated diols:

2-oxo-4,6-dimethyl-1,3,2-dioxaphosphorinan from 2,4-pentanediol;
2-oxo-1,3,2-dioxaphosphorinan from 1,3-propanediol; and
2-oxo-5,5-dimethyl-1,3,2-dioxaphosphorinan from 2,2-dimethyl-1,3-propanediol.

EXAMPLE 14

O-Isopropyl P-ethylphosphonite

A solution of 50 g of ethyl dichlorophosphine dissolved in 50 ml of methylene chloride was added dropwise over a 40 minute period to a solution of 48.0 g of isopropanol, 30.2 g of pyridine, and 150 ml of methylene chloride at 5° C. The reaction was stirred and cooled for an additional 30 minutes after the addition of the phosphine was complete, refluxed overnight and then concentrated. The concentrate was triturated with 350 ml of THF and the solids removed by filtration. The filtrate was concentrated, triturated with 250 ml of ether, filtered, and the filtrate concentrated to yield 49.0 g of the desired phosphonite as a clear liquid.

Using the procedure described above, the following phosphonites of Formula IV were prepared from the indicated dichlorophosphines and alcohols:
O-isopropyl P-n-propylphosphonite from n-propyl dichlorophosphine and isopropanol;
O-isopropyl P-methylphosphonite from methyl dichlorophosphine and isopropanol;
O-ethyl P-phenylphosphonite from phenyl dichlorophosphine and ethanol;
O-ethyl P-isopropylphosphonite from isopropyl dichlorophosphine and ethanol;
O-ethyl P-ethylphosphonite from ethyl dichlorophosphine and ethanol; and
O-ethyl P-methylphosphonite from methyl dichlorophosphine and ethanol.

EXAMPLE 15

O-Methyl P-neopentylphosphonite

Magnesium turnings, 8.38 g, were crushed in 40 ml of anhydrous ether and 3.0 ml of neopentyl bromide added. Mild heating was used to initiate the reaction. Once the reaction started, the heat was removed. Then a solution of 47 g of neopentyl bromide dissolved in 80 ml of ether was added dropwise over 90 minutes. The rate of the addition was such that the reaction mixture was kept at a gentle reflux. After the addition was complete the reaction was refluxed for an additional 30 minutes and allowed to cool to room temperature and stir overnight.

The Grignard solution prepared above was added dropwise over 100 minutes to a solution of 93.4 g of phosphorous trichloride in 240 ml of anhydrous ether which was cooled to −65° C. The reaction temperature was kept at or below −55° C. during the addition. The reaction solution was allowed to warm to room temperature over 90 minutes. After one hour of stirring at room temperature the reaction solution was cooled by an ice and water bath and a solution of 76.2 g of methanol and 165.9 g of pyridine was added dropwise over 90 minutes. The reaction temperature did not exceed 20° C. during the addition. After 30 minutes of additional stirring the cooling bath was removed and the reaction was allowed to stand at room temperature over the weekend. The reaction solution was vacuum filtered through Celite, the filter cake rinsed with 800 ml of ether and the filtrate concentrated to yield 43.2 g of a pale yellow oil. A vacuum of 3 Torr was pulled on the sample for 3 hours to remove the residual trimethyl phosphite. Yield was 12.6 g of a yellow liquid. The material was used without further purification.

Using the procedure described above, O-methyl P-isobutylphosphonite was prepared from isobutylmagnesium bromide.

EXAMPLE 16

Di-n-Propylphosphine oxide

Diethyl phosphite, 55.2 g, was added dropwise to 800 ml of 2.0M n-propylmagnesium chloride at 15° C. over a 40 minute period at such a rate that the temperature of the reaction mixture did not exceed 30° C. The reaction mixture was stirred for an additional 10 minutes, allowed to warm and stir for four hours at room temperature and then cooled to 10° C. A solution of 230 g of potassium carbonate in 400 ml of water was added dropwise over a 45 minute period at such a rate that the reaction temperature did not exceed 32° C. After stirring for an additional 15 minutes, the reaction was filtered through a fritted glass funnel, the filter cake rinsed with 1000 ml of 2/1 ethanol/methanol and the combined filtrates concentrated. The concentrate was triturated with 120 ml of methylene chloride and the insolubles removed by filtration. The filtrate was dried with 4A molecular sieves, filtered and concentrated to yield 29.2 g of the desired phosphine oxide as a tan solid, melting point 49°–51° C.

Using the procedure described above, diethylphosphine oxide was prepared from ethylmagnesium bromide and diethyl phosphite.

PREPARATION OF THE P-(HYDROXYMETHYL)PHOSPHONATE, P-(HYDROXYMETHYL)PHOSPHINATE AND (HYDROXYMETHYL)-PHOSPHINE OXIDE INTERMEDIATES OF FORMULA III

EXAMPLE 17

Diethyl P-(Hydroxymethyl)phosphonate

A slurry of 204.2 g of diethyl phosphite, 45.0 g of paraformaldehyde and 8 ml of triethylamine was heated to 65° C. The reaction then exothermed to 155° C. over 5 minutes and then the reaction temperature began to fall. The reaction became homogeneous when the reaction temperature reached 110° C. When the reaction had cooled to 65° C. the volatiles were removed in vacuo to yield 245.9 g of a cloudy oil as the desired P-(hydroxymethyl)phosphonate intermediate.

Using the procedure described above, the following P-(hydroxymethyl)phosphonates of Formula III were prepared from paraformaldehyde and the indicated phosphite of Formula IV: diallyl P-(hydroxymethyl)-phosphonate from diallyl phosphite (Example 10);
di-n-butyl P-(hydroxymethyl)phosphonate from di-n-butyl phosphite; diisopropyl P-(hydroxymethyl)-phosphonate from diisopropyl phosphite (Example 10);
di-n-propyl P-(hydroxymethyl)phosphonate from di-n-propyl phosphite (Example 10);
bis-(2-chloroethyl) P-(hydroxymethyl)phosphonate from bis-(2-chloroethyl) phosphite (Example 10);
dimethyl P-(hydroxymethyl)phosphonate from dimethyl phosphite; and
diethyl P-(hydroxymethyl)thiophosphonate from diethyl thiophosphite (Example 12).

EXAMPLE 18

O-Ethyl-O-isopropyl P-(hydroxymethyl) phosphonate

A: Diethyl P-(acetoxymethyl)phosphonate

To a solution cooled to 8° C. of 170 ml of THF, 27.07 g of diethyl P-(hydroxymethyl)phosphonate (Example 17) and 24.5 ml of triethylamine was added dropwise over 30 minutes a solution of 10 ml of THF and 13.7 g of acetyl chloride. The reaction temperature did not exceed 25° C. during the addition. After an additional 30 minutes of stirring the reaction was allowed to warm to room temperature and stir overnight, then gravity filtered, the filter cake rinsed with 200 ml of THF and the combined filtrates were concentrated to yield 28.8 g of the desired phosphonate intermediate as a brown liquid.

B: O-Ethyl P-(acetoxymethyl)phosphonoyl chloride

To a mixture of 35.3 g of phosphorous pentachloride and 180 ml of methylene chloride was added dropwise over a 50 minute period, a solution of 28.2 g of diethyl P-(acetoxymethyl)phosphonate, prepared in Example 18A, dissolved in 30 ml of methylene chloride. The reaction temperature was kept between 25°–29° C. during the phosphonate addition. After ⅓ of the solution had been added the reaction became homogeneous. The reaction was allowed to stir overnight at room temperature. The reaction was concentrated, 100 ml of toluene added and the resulting mixture reconcentrated. The concentrate was triturated with a mixture of 100 ml of hexanes and 100 ml of ether, the mixture gravity filtered and concentrated to yield 27.6 g of the desired phosphoryl chloride intermediate as a brown liquid.

C: O-Ethyl-O-isopropyl P-(acetoxymethyl)phosphonate

To a solution of 160 ml of THF and 26.7 g of O-ethyl P-(acetoxymethyl)phosphonoyl chloride, (Example 18B), that was cooled in an ice and water bath was added dropwise over a 60 minute period a solution of 8.7 g of isopropanol, 21.0 ml of triethylamine and 40 ml of THF. After an additional 30 minutes, the cooling bath was removed and the reaction was allowed to warm to room temperature and stir overnight. The reaction was gravity filtered and the filter cake washed with 150 ml of acetone. The combined filtrates were concentrated, the concentrate triturated with 150 ml of ether, filtered and concentrated to yield 24.8 g of the desired phosphonate intermediate as a brown liquid.

D: O-Ethyl-O-isopropyl P-(hydroxymethyl)phosphonate

Sodium metal spheres, 3.1 g, were cautiously added in small portions over a 20 minute period to 50 ml of ethanol. Once the sodium spheres had completely reacted, a solution of 23.2 g of O-ethyl-O-isopropyl P-(acetoxymethyl)phosphonate, (Example 18C), dissolved in 50 ml of absolute ethanol was added all at once to the room temperature reaction mixture. Periodically the pH of the reaction was checked and enough sodium spheres added to make the reaction strongly basic. The reaction was allowed to stir overnight at room temperature. The pH of the reaction was checked and found to be neutral. An additional 1.3 g of sodium spheres was added and the reaction was allowed to stir for six hours at room temperature. A reaction aliquot was examined by GLC which indicated that the starting material had been completely consumed. The reaction mixture was neutralized by the addition of an acidic ion exchange resin. The resin was removed by filtration, the filtrate concentrated, and 100 ml of toluene added and the resulting mixture concentrated to yield 18.8 g of the desired P-(hydroxymethyl)phosphonate as a yellow liquid.

Using the procedures described above, the following P-(hydroxymethyl)phosphonamides of Formula III were prepared except that the indicated amine replaced isopropanol in Example 18C:
N,N-diethyl-O-Ethyl P-(hydroxymethyl)phosphonamide using 2 equivalents of diethylamine in place of the isopropanol and triethylamine; and
N-methyl-N-phenyl-O-ethyl P-(hydroxymethyl)phosphonamide using N-methylaniline.

EXAMPLE 19

N-Allyl-O-ethyl P-(hydroxymethyl)phosphonamide

Freshly ground potassium carbonate, 1.5 g, was added to a mixture of 1.1 g of N-allyl-O-ethyl P-(acetoxymethyl)phosphonamide, prepared by substituting 2 equivalents of allylamine for the isopropanol and triethylamine in Example 18C, and 20 ml of methanol. After 15 minutes the reaction was complete as determined by GLC analysis. The reaction mixture was filtered through Celite ® and the filter cake rinsed with ethyl acetate. The combined filtrates were concentrated, the resulting solid triturated with a mixture of 15 ml of methylene chloride and 1 ml of methanol, the solution filtered and the filtrate concentrated to yield 0.29 g of the desired phosphonamide as an oil in 95% purity.

Using the procedure described in Example 19, N,N-diallyl-O-ethyl P-(hydroxymethyl)phosphonamide was prepared except that N,N-diallylamine was used in place of N-allylamine.

EXAMPLE 20

N,N'-[Bis(di-n-propyl)] P-(hydroxymethyl)phosphondiamide

A: [N,N-(Di-n-propyl)] P-(acetoxymethyl)phosphonamidoyl chloride

A solution of 9.8 g of O-ethyl-[N,N-(di-n-propyl)] P-(acetoxymethyl)phosphonamide, prepared by substituting di-n-propylamine for isopropanol in Example 18C, dissolved in 10 ml of methylene chloride was added dropwise to a mixture of 7.97 g of phosphorous pentachloride and 110 ml of methylene chloride over 15 minutes. No significant exotherm occurred and the reaction was allowed to stir overnight at room temperature. A reaction aliquot was concentrated under reduced pressure. Phosphorus NMR indicated that the reaction was complete. The reaction was concentrated, 100 ml of toluene added and the mixture concentrated to yield 7.4 g of the desired phosphonamidoyl chloride as a brown oil.

B: N,N'-[Bis(di-n-propyl)] P-(acetoxymethyl)phosphondiamide

A solution of 13.1 g of di-n-propylamine diluted with 15 ml of toluene was added dropwise over twenty minutes to 9.8 g of [N,N-(di-n-propyl)] P-(acetoxymethyl)-phosphonamidoyl chloride, (Example 20A), in 70 ml of toluene. No significant exotherm occurred. The reaction was then heated to reflux for one hour, then allowed to cool below the reflux temperature of the solvent and an additional 3.0 g of di-n-propylamine was added. The reaction was refluxed for an additional 45 minutes and then allowed to cool and stir overnight. The reaction slurry was gravity filtered and concentrated to yield 10.3 g of the crude phosphondiamide as a brown oil. The oil was dissolved in 8 ml of methylene chloride and flash chromatographed on Merck ® Silica gel (230-400 mesh). Similar fractions were combined to yield 2.2 g of the partially purified desired phosphondiamide as a yellow oil. The partially purified material was rechromatographed using the above flash chromatography conditions to yield 1.1 g of the desired phosphondiamide in 90% purity.

C: N,N'-[Bis(di-n-propyl)] P-(hydroxymethyl)phosphondiamide

A solution of 5 ml of 1.0M sodium ethoxide in ethanol was added at once to 1.1 g of N,N'-[bis(di-n-propyl)] P-(acetoxymethyl)phosphondiamide, (Example 20B), in 15 ml of absolute ethanol. After several hours of stirring at room temperature the reaction solution was strongly basic to pH paper and the reaction was allowed to stir overnight at room temperature. Dowex ® 50X8 acidic ion exchange resin (2.5 g) was added and the reaction mixture was allowed to stand at room temperature overnight. The ion exchange resin was removed by gravity filtration and the filtrate concentrated to yield 0.88 g of the desired phosphondiamide.

EXAMPLE 21

2-(Hydroxymethyl)-2-oxo-4-methyl-1,3,2-dioxaphosphorinan

A mixture of 23.0 g of 2-oxo-4-methyl-1,3,2-dioxaphosphorinan, prepared in Example 13B, 5.4 of paraformaldehyde, and 2 ml of triethylamine was heated to 50° C. After stirring for 40 minutes the reaction mixture had become homogeneous and the reaction was allowed to cool to room temperature. The reaction mixture was concentrated under high vacuum at room temperature to yield 28.4 g of the crude desired dioxaphosphorinan as a viscous oil ($^{31}$P NMR indicated a mixture of diastereomers).

Using the procedures described above, the following 2-(hydroxymethyl)-2-oxo-1,3,2-dioxaphosphorinans of Formula III were prepared from paraformaldehyde and the indicated 2-oxo-1,3,2-dioxaphosphorinans of Formula IV (Example 13):

4,6-dimethyl-2-(hydroxymethyl)-2-oxo-1,3,2-dioxaphosphorinan from 4,6-dimethyl-2-oxo-1,3,2-dioxaphosphorinan;

2-(hydroxymethyl)-2-oxo-1,3,2-dioxaphosphorinan from 2-oxo-1,3,2-dioxaphosphorinan; and 5,5-dimethyl-2-(hydroxymethyl)-2-oxo-1,3,2-dioxaphosphorinan from 5,5-dimethyl-2-oxo-1,3,2-dioxaphosphorinan.

EXAMPLE 22

O-Isopropyl P-ethyl(hydroxymethyl)phosphinate

Method A

A mixture of 90 ml of THF (dried over 4A molecular sieves), 4 ml of triethylamine, 13.2 g of O-isopropyl P-ethylphosphonite, (Example 14), and 3.2 g of paraformaldehyde was heated to 55° C. for 18 hours, then refluxed for an additional 4 hours. The reaction was allowed to cool to room temperature, filtered and concentrated. Then 100 ml of toluene was added and the solution reconcentrated. The sample was placed under vacuum (~2 torr) and heated to 80° C. for one hour to remove volatile impurities. The yield of the desired phosphinate was 16.2 g of a clear liquid in 90% purity.

Method B

A mixture of 20.27 g of O-isopropyl P-ethylphosphonite, (Example 14), 3.8 g of paraformaldehyde and 2 ml of triethylamine was heated to 80° C. After 40 minutes the reaction mixture became homogeneous. Then the reaction was allowed to stir and cool to room temperature. The triethylamine was removed under high vacuum. Several phosphorus containing compounds were present as indicated by $^{31}$P NMR in which the desired product was present as 55% of the mixture.

Using the procedure described above in Example 22, Method B, the following P-(hydroxymethyl)phosphinates of Formula III were prepared from paraformaldehyde and the indicated phosphonite:

O-ethyl P-phenyl(hydroxymethyl)phosphinate from O-ethyl P-phenylphosphonite (Example 14);

O-ethyl P-isopropyl(hydroxymethyl)phosphinate from O-ethyl P-isopropylphosphonite (Example 14);

O-ethyl P-ethyl(hydroxymethyl)phosphinate from O-ethyl P-ethylphosphonite (Example 14);

O-ethyl P-methyl(hydroxymethyl)phosphinate from O-ethyl P-methylphosphonite;

O-methyl P-isobutyl(hydroxymethyl)phosphinate from O-methyl P-isobutylphosphonite (Example 15);

O-methyl P-neopentyl(hydroxymethyl)phosphinate from O-methyl P-neopentylphosphonite (Example 15)

O-isopropyl P-n-propyl(hydroxymethyl)phosphinate from O-isopropyl P-n-propylphosphonite (Example 14); and O-isopropyl P-methyl(hydroxymethyl)phosphinate from O-isopropyl P-methylphosphonite (Example 14).

Method C

A mixture of 39.6 g of O-isopropyl P-ethylphosphonite, (Example 14), 8.52 g of paraformaldehyde, and 3 ml of triethylamine was heated to 80° C. for 6 hours. $^{31}$P NMR indicated the reaction was complete. The reaction was allowed to cool to room temperature and was then diluted with 150 ml of THF, gravity filtered, and concentrated under reduced pressure. The colorless oil was then further concentrated under high vacuum at 75° C. for 2 hours to yield 46.6 g of the desired hydroxymethyl compound in 90+% purity, as determined by GLC and $^{31}$P NMR.

Using the procedure described above in Example 22, Method C, the following P-(hydroxymethyl)phosphinates of Formula III were prepared from paraformaldehyde and the indicated phosphonite:

O-isopropyl P-methyl(hydroxymethyl)phosphinate from O-isopropyl P-methylphosphonite (Example 14); and O-isopropyl P-n-propyl(hydroxymethyl)phosphinate from O-isopropyl P-n-propylphosphonite (Example 14).

EXAMPLE 23

Di-n-Propyl(Hydroxymethyl)phosphine oxide

A 37% of formaldehyde solution, 16.2 g, was added in small portions over a five minute period to solution of 40 ml of methanol, 21.78 g of di-n-propyl phosphine oxide, (Example 16), and 1.5 ml of triethylamine. The reaction exothermed to 30° C. and was allowed to stir for ten minutes before it was warmed to 70° C. for three hours. The reaction was then allowed to cool to room temperature and stand overnight. The reaction was concentrated, the concentrate dissolved in 70 ml of THF, filtered and reconcentrated. The concentrate was diluted with 60 ml of 1,4-dioxane which was distilled off to yield 19.8 g of the desired phosphine oxide as an oil.

Using the procedure described above, diethyl(hydroxymethyl)phosphine oxide was prepared from diethylphosphine oxide (Example 16).

PREPARATION OF THE PHOSPHOSULFONATES OF FORMULA I

Example 24

Diethyl P-[[(2-chloro-6-methylphenyl)sulfonyloxy]methyl]-phosphonate (Compound 45)

A solution of 4.63 g of 2-chloro-6-methylbenzenesulfonyl chloride dissolved in 20 ml of anhydrous ether was added dropwise over a 15 minute period to a mixture of 3.50 g of diethyl P-(hydroxymethyl)phosphonate (Example 17), 5 ml of triethylamine and 15 ml of anhydrous ether. The addition was mildly exothermic and a white precipitate began to form shortly after the addition of the sulfonyl chloride was begun. The reaction was stirred at room temperature overnight. After 48 hours of additional stirring the reaction solution was diluted with 200 ml of ethyl acetate and 80 ml of water. The organic phase was washed with two 90 ml portions of water, dried with magnesium sulfate, filtered and concentrated to yield 6.4 g of an oil which solidified upon standing, mp 41°–43° C.

Using the procedure described in this example, the following phosphosulfonates as described in Table I were prepared from the indicated commercially available sulfonyl chloride of Formula II and a P-(hydroxymethyl)phosphonate of Formula III unless otherwise noted.

Compound 1: p-toluenesulfonyl chloride and diethyl P-(hydroxymethyl)phosphonate (Example 17);

Compound 2: p-toluenesulfonyl chloride and dimethyl P-(hydroxymethyl)phosphonate (Example 17);

Compound 3: 2-chlorobenzenesulfonyl chloride and diethyl P-(hydroxymethyl)phosphonate (Example 17);

Compound 4: 4-chlorobenzenesulfonyl chloride and diethyl P-(hydroxymethyl)phosphonate (Example 17);

Compound 5: benzenesulfonyl chloride and diethyl P-(hydroxymethyl)phosphonate (Example 17);

Compound 6: 2-methoxycarbonylbenzenesulfonyl chloride and diethyl P-(hydroxymethyl)phosphonate (Example 17);

Compound 7: 3-chloro-4-methylbenzenesulfonyl chloride and diethyl P-(hydroxymethyl)phosphonate (Example 17);

Compound 8: 2-nitrobenzenesulfonyl chloride and diethyl P-(hydroxymethyl)phosphonate (Example 17);

Compound 9: 2,5-dichlorobenzenesulfonyl chloride and diethyl P-(hydroxymethyl)phosphonate (Example 17);

Compound 10: 2,4,5-trichlorobenzenesulfonyl chloride and diethyl P-(hydroxymethyl)phosphonate (Example 17);

Compound 11: 2-thiophenesulfonyl chloride and diethyl P-(hydroxymethyl)phosphonate (Example 17);

Compound 12: 4-fluorobenzenesulfonyl chloride and diethyl P-(hydroxymethyl)phosphonate (Example 17);

Compound 13: 2,3-dichlorobenzenesulfonyl chloride and diethyl P-(hydroxymethyl)phosphonate (Example 17);

Compound 14: 3,4-dichlorobenzenesulfonyl chloride and diethyl P-(hydroxymethyl)phosphonate (Example 17);

Compound 15: p-toluenesulfonyl chloride and di-n-butyl P-(hydroxymethyl)phosphonate (Example 17);

Compound 16: 2,5-dichlorobenzenesulfonyl chloride and di-n-butyl P-(hydroxymethyl)phosphonate (Example 17);

Compound 17: 4-methoxybenzenesulfonyl chloride and diethyl P-(hydroxymethyl)phosphonate (Example 17);

Compound 18: 5-chloro-2-thiophenesulfonyl chloride and diethyl P-(hydroxymethyl)phosphonate (Example 17);

Compound 19: 2,5-dichlorobenzenesulfonyl chloride and N-allyl-O-ethyl P-(hydroxymethyl)phosphonamide (Example 19);

Compound 20: 1,3-dimethyl-5-chloro-4-pyrazolesulfonyl chloride and diethyl P-(hydroxymethyl)phosphonate (Example 17);

Compound 21: 3-chlorobenzenesulfonyl chloride and diethyl P-(hydroxymethyl)phosphonate (Example 17);

Compound 22: 3-methylbenzenesulfonyl chloride and diethyl P-(hydroxymethyl)phosphonate (Example 17);

Compound 23: benzylsulfonyl chloride and diethyl P-(hydroxymethyl)phosphonate (Example 17);

Compound 24: 2,5-dimethoxybenzenesulfonyl chloride and diethyl P-(hydroxymethyl)phosphonate (Example 17);

Compound 25: 3,5-dichlorobenzenesulfonyl chloride and diethyl P-(hydroxymethyl)phosphonate (Example 17);

Compound 26: 3-nitrobenzenesulfonyl chloride and diethyl P-(hydroxymethyl)phosphonate (Example 17);

Compound 27: 2,5-dichlorobenzenesulfonyl chloride and diallyl P-(hydroxymethyl)phosphonate (Example 17);

Compound 28: 2-methyl-5-nitrobenzenesulfonyl chloride and diethyl P-(hydroxymethyl)phosphonate (Example 17);

Compound 29: 3,5-dimethyl-4-isoxazolesulfonyl chloride and diethyl P-(hydroxymethyl)phosphonate (Example 17);

Compound 31: 3-(trifluoromethyl)benzenesulfonyl chloride and diethyl P-(hydroxymethyl)phosphonate (Example 17);

Compound 32: 4-(trifluoromethyl)benzenesulfonyl chloride and diethyl P-(hydroxymethyl)phosphonate (Example 17);

Compound 33: 3-nitro-4-methylbenzenesulfonyl chloride (Example 8) and diethyl P-(hydroxymethyl)phosphonate (Example 17);

Compound 34: 2,4-dichlorobenzenesulfonyl chloride and diethyl P-(hydroxymethyl)phosphonate (Example 17);

Compound 35: 2,5-dichlorobenzenesulfonyl chloride and bis-(2-chloroethyl) P-(hydroxymethyl)phosphonate (Example 17);

Compound 36: 8-quinolinesulfonyl chloride and diethyl P-(hydroxymethyl)phosphonate (Example 17);

Compound 37: 2,5-dichlorobenzenesulfonyl chloride and dimethyl P-(hydroxymethyl)phosphonate (Example 17);

Compound 38: 2-nitrobenzenesulfonyl chloride and dimethyl P-(hydroxymethyl)phosphonate (Example 17);

Compound 40: 2,3-dibromo-5-thiophenesulfonyl chloride and diethyl P-(hydroxymethyl)phosphonate (Example 17);

Compound 41: 2,5-dichloro-3-thiophenesulfonyl chloride and diethyl P-(hydroxymethyl)phosphonate (Example 17);

Compound 42: 4-bromo-2,5-dichlorothiophenesulfonyl chloride and diethyl P-(hydroxymethyl)phosphonate (Example 17);

Compound 43: 2-nitro-4-chlorobenzenesulfonyl chloride and diethyl P-(hydroxymethyl)phosphonate (Example 17);

Compound 44: 2,6-dichlorobenzenesulfonyl chloride and diethyl P-(hydroxymethyl)phosphonate (Example 17);

Compound 46: 2,5-dichlorobenzenesulfonyl chloride and diisopropyl P-(hydroxymethyl)phosphonate (Example 17);

Compound 47: 2-chloro-5-nitrobenzenesulfonyl chloride and diethyl P-(hydroxymethyl)phosphonate (Example 17);

Compound 48: 1-naphthalenesulfonyl chloride and diethyl P-(hydroxymethyl)phosphonate (Example 17);

Compound 49: 2,5-dichlorobenzenesulfonyl chloride and di-n-propyl P-(hydroxymethyl)phosphonate (Example 17);

Compound 51: 2-naphthalenesulfonyl chloride and diethyl P-(hydroxymethyl)phosphonate (Example 17);

Compound 52: 2-bromo-5-(trifluoromethyl)benzenesulfonyl chloride and diethyl P-(hydroxymethyl)phosphonate (Example 17);

Compound 53: 2,5-dibromobenzenesulfonyl chloride and diethyl P-(hydroxymethyl)phosphonate (Example 17);

Compound 54: 2-cyanobenzenesulfonyl chloride (Example 1C) and diethyl P-(hydroxymethyl)phosphonate (Example 17);

Compound 56: 2-nitro-5-chlorobenzenesulfonyl chloride and diethyl P-(hydroxymethyl)phosphonate (Example 17);

Compound 57: 2-(trifluoromethyl)-4-chlorobenzenesulfonyl chloride and diethyl P-(hydroxymethyl)phosphonate (Example 17);

Compound 58: 2-nitro-4-methylbenzenesulfonyl chloride (Example 1C) and diethyl P-(hydroxymethyl)phosphonate (Example 17);

Compound 59: 2,4-dichloro-5-methylbenzenesulfonyl chloride and diethyl P-(hydroxymethyl)phosphonate (Example 17);

Compound 60: 2-methyl-5-chlorobenzenesulfonyl chloride (Example 1C) and diethyl P-(hydroxymethyl)phosphonate (Example 17);

Compound 61: 2-chloro-5-methylbenzenesulfonyl chloride (Example 1C) and diethyl P-(hydroxymethyl)phosphonate (Example 17);

Compound 62: 2-nitro-4-methoxybenzenesulfonyl chloride (Example 1C) and diethyl P-(hydroxymethyl)phosphonate (Example 17);

Compound 63: 2,6-dichlorobenzenesulfonyl chloride and N,N-diethyl-O-ethyl P-(hydroxymethyl)phosphonamide (Example 18);

Compound 66: 2,6-dichloro-3-methylbenzenesulfonyl chloride (Example 1C) and diethyl P-(hydroxymethyl)phosphonate (Example 17);

Compound 69: 2,4,6-trimethylbenzenesulfonyl chloride and diethyl P-(hydroxymethyl)phosphonate (Example 17);

Compound 70: 2-bromobenzenesulfonyl chloride and diethyl P-(hydroxymethyl)phosphonate (Example 17);

Compound 75: 2-(trifluoromethyl)-4-fluorobenzenesulfonyl chloride and diethyl P-(hydroxymethyl)phosphonate (Example 17);

Compound 109: 2,6-dichlorobenzenesulfonyl chloride and dimethyl P-(hydroxymethyl)phosphonate (Example 17);

Compound 115: 2-chloro-6-methylbenzenesulfonyl chloride and dimethyl P-(hydroxymethyl)phosphonate (Example 17); and Compound 136: 2,4,6-trimethylbenzene-1,3-bis(sulfonyl chloride) and diethyl P-(hydroxymethyl)phosphonate (Example 17).

EXAMPLE 25

Diethyl P-[[(2-(trifluoromethyl)phenyl)sulfonyloxy]methyl]phosphonate (Compound 30)

A solution of 11.1 g of diethyl P-(hydroxymethyl)phosphonate (Example 17), 11 ml of triethylamine and 30 ml of ether was added dropwise over one hour to 15.5 g of 2-(trifluoromethyl)benzenesulfonyl chloride and 50 ml of anhydrous ether. The addition was mildly exothermic and a white precipitate began to form shortly after the addition was begun. The reaction was stirred overnight, then diluted with 300 ml of ethyl acetate and washed with three 85 ml portions of water. The organic phase was dried with magnesium sulfate, filtered and concentrated. The resulting crude product was purified via flash chromatography on Merck® silica gel (230–400 mesh) eluting with hexanes and ethyl acetate to yield 10.5 g of the desired product as an oil.

Using the procedure described in this example, the following phosphosulfonates as described in Table I were prepared from the indicated commercially available sulfonyl chloride of Formula II and P-(hydroxymethyl)phosphonate or P-(hydroxymethyl)phosphinate of Formula III unless otherwise noted:

Compound 39: 2,6-dichlorobenzenesulfonyl chloride and N,N-diallyl-O-ethyl P-(hydroxymethyl)phosphonamide (Example 19);

Compound 64: 2-chloro-6-methylbenzenesulfonyl chloride and N-methyl-N-phenyl-O-ethyl P-(hydroxymethyl)phosphonamide (Example 18);

Compound 68: 2-fluoro-4-bromobenzenesulfonyl chloride and diethyl P-(hydroxymethyl)phosphonate (Example 17);

Compound 71: 2-fluorobenzenesulfonyl chloride and diethyl P-(hydroxymethyl)phosphonate (Example 17);

Compound 76: 2-fluoro-5-(trifluoromethyl)benzenesulfonyl chloride and diethyl P-(hydroxymethyl)phosphonate (Example 17);

Compound 77: 2,4-difluorobenzenesulfonyl chloride and diethyl P-(hydroxymethyl)phosphonate (Example 17);

Compound 80: 2-(trifluoromethyl)benzenesulfonyl chloride and O-ethyl P-ethyl(hydroxymethyl)phosphinate (Example 22, Method B);

Compound 81: 2-(trifluoromethyl)-4-bromobenzenesulfonyl chloride and diethyl P-(hydroxymethyl)phosphonate (Example 17);

Compound 82: 2-methylbenzenesulfonyl chloride (Example 4) and diethyl P-(hydroxymethyl)phosphonate (Example 17);

Compound 83: 2-isopropylbenzenesulfonyl chloride (Example 4) and diethyl P-(hydroxymethyl)phosphonate (Example 17);

Compound 84: 2,3,4,5,6-pentafluorobenzenesulfonyl chloride and diethyl P-(hydroxymethyl)phosphonate (Example 17);

Compound 87: 2-(trifluoromethoxy)benzenesulfonyl chloride and diethyl P-(hydroxymethyl)phosphonate (Example 17);

Compound 107: 2-methyl-6-nitrobenzenesulfonyl chloride (Example 1C) and diethyl P-(hydroxymethyl)phosphonate (Example 17);

Compound 110: cyclohexanesulfonyl chloride (Example 4) and diethyl P-(hydroxymethyl)phosphonate (Example 17);

Compound 112: 2,4,6-trichlorobenzenesulfonyl chloride and diethyl P-(hydroxymethyl)phosphonate (Example 17);

Compound 113: 2-chloro-6-nitrobenzenesulfonyl chloride (Examples 4 and 6) and diethyl P-(hydroxymethyl)phosphonate (Example 17);

Compound 114: 2,6-dimethylbenzenesulfonyl chloride (Example 4) and diethyl P-(hydroxymethyl)phosphonate (Example 17);

Compound 118: 2,4,6-tri-isopropylbenzenesulfonyl chloride and diethyl P-(hydroxymethyl)phosphonate (Example 17);

Compound 126: 2,6-diethylbenzenesulfonyl chloride (Examples 3C and 3D) and diethyl P-(hydroxymethyl)phosphonate (Example 17);

Compound 131: 2,6-dimethyl-4-chlorobenzenesulfonyl chloride (Example 5) and diisopropyl P-(hydroxymethyl)phosphonate (Example 17);

Compound 134: 2,4-dichloro-6-methylbenzenesulfonyl chloride (Example 1C) and diisopropyl P-(hydroxymethyl)phosphonate (Example 17);

Compound 137: 2,4-dichloro-6-methoxybenzenesulfonyl chloride (Example 5B) and diisopropyl P-(hydroxymethyl)phosphonate (Example 17);

Compound 146: 2,5-dichloro-3,6-dimethylbenzenesulfonyl chloride (Example 5B) and diisopropyl P-(hydroxymethyl)phosphonate (Example 17);

Compound 158: 2-methyl-3-chlorobenzenesulfonyl chloride and diisopropyl P-(hydroxymethyl)phosphonate (Example 17);

Compound 159: 2-methoxy-5-chlorobenzenesulfonyl chloride and diisopropyl P-(hydroxymethyl)phosphonate (Example 17);

Compound 160: 2,3-dimethyl-6-nitrobenzenesulfonyl chloride (Example 1C) and diethyl P-(hydroxymethyl)phosphonate (Example 17);

Compound 167: 2-(trifluoromethyl)benzenesulfonyl chloride and O-ethyl-O-isopropyl P-(hydroxymethyl)phosphonate (Example 17);

Compound 168: 2-chloro-6-methylbenzenesulfonyl chloride and diethyl P-(hydroxymethyl)thiophosphonate (Example 12);

Compound 170: 2-(trifluoromethyl)benzenesulfonyl chloride and O-isopropyl P-ethyl(hydroxymethyl)phosphinate (Example 22, Method A);

Compound 180: 2,4-dichlorobenzenesulfonyl chloride and O-isopropyl P-ethyl(hydroxymethyl)phosphinate (Example 22, Method C), wherein methylene chloride was used in place of ether as the solvent and 1.1 equivalents of DMAP were added to the sulfonyl chloride solution;

Compound 184: 2-chloro-6-isopropylbenzenesulfonyl chloride (Example 9) and diisopropyl P-(hydroxymethyl)phosphonate (Example 17), wherein methylene chloride was used in place of ether as the solvent and 0.05 equivalent of DMAP was added to the sulfonyl chloride solution;

Compound 205: 3,4-dichloro-2-methylbenzenesulfonyl chloride (Example 5B) and diethyl P-(hydroxymethyl)phosphonate (Example 17), wherein 0.05 equivalent of DMAP was added to the sulfonyl chloride solution;

Compound 207: 2-t-butylbenzenesulfonyl chloride (Example 4) and diethyl P-(hydroxymethyl)phosphonate (Example 17), wherein 0.1 equivalent of DMAP was added to the sulfonyl chloride solution; and Compound 210: 2,3,4-trichlorobenzenesulfonyl chloride and diethyl P-(hydroxymethyl)phosphonate (Example 17), wherein methylene chloride was used in place of ether as the solvent and 0.1 equivalent of DMAP was added to the sulfonyl chloride solution.

Compound 223: 2-methoxy-6-(trifluoromethyl)benzenesulfonyl chloride (Example 2) and O-ethyl-O-isopropyl P-(hydroxymethyl)phosphonate (Example 18), wherein 0.1 g of DMAP was added to the sulfonyl chloride solution;

Compound 226: 2-chlorobenzenesulfonyl chloride and diisopropyl P-(hydroxymethyl)phosphonate (Example 17), wherein 0.1 g of DMAP was added to the sulfonyl chloride solution;

Compound 237: 2-methoxy-6-(trifluoromethyl)benzenesulfonyl chloride (Example 2) and diethyl P-(hydroxymethyl)phosphonate (Example 17), wherein methylene chloride was used in place of ether as the solvent and 0.1 g of DMAP was added to the sulfonyl chloride solution;

Compound 238: 1,5-dimethyl-3-trifluoromethyl-4-pyrazolesulfonyl chloride (Example 63) and diethyl P-(hydroxymethyl)phosphonate (Example 17), wherein methylene chloride was used in place of ether as the solvent and 0.1 g of DMAP was added to the sulfonyl chloride solution;

Compound 244: 2,5-dichloro-4-methyl-3-thiophenebenzenesulfonyl chloride (Example 61) and diethyl P-(hydroxymethyl)phosphonate (Example 17), wherein methylene chloride was used in place of ether as the solvent and 0.1 g of DMAP was added to the sulfonyl chloride solution;

Compound 257: 2-ethoxy-6-(trifluoromethyl)benzenesulfonyl chloride (Example 65) and diisopropyl P-(hydroxymethyl)phosphonate (Example 17, wherein methylene chloride was used in place of ether as the solvent and 0.1 g of DMAP was added to the sulfonyl chloride solution;

EXAMPLE 26

Diisopropyl P-[[(2-chloro-6-methylphenyl)sulfonyloxy]methyl]-phosphonate (Compound 72)

A solution of 21.7 g of 2-chloro-6-methylbenzenesulfonyl chloride dissolved in 40 ml of ether was added dropwise over 90 minutes to a mixture of 20.6 g of diisopropyl P-(hydroxymethyl)-phosphonate, (Example 17), 80 ml of ether, and 15.4 ml of triethylamine. The addition was mildly exothermic and the reaction was cooled using a cool water bath (no ice). The reaction was allowed to stir overnight at room temperature and then was diluted with 300 ml of ethyl acetate, washed with three 100 ml portions of water, the organic phase dried with magnesium sulfate, filtered and concentrated under reduced pressure to yield 34.0 g of the desired product as a yellow oil.

EXAMPLE 27

Diisopropyl P-[[(2-(trifluoromethyl)phenyl)sulfonyloxy]methyl]-phosphonate (Compound 143)

A solution of 30 ml of ether, 13.3 g of diisopropyl P-(hydroxymethyl)phosphonate, prepared in Example 17, and 10.5 ml of triethylamine was added dropwise over 60 minutes to a solution of 15.35 g of 2-(trifluoromethyl)benzenesulfonyl chloride and 50 ml of ether. After the mild exotherm, the reaction was allowed to stir at room temperature overnight and then was diluted with 200 ml of ethyl acetate, the ethyl acetate solution washed with two 100 ml portions of water, dried with magnesium sulfate, filtered, and concentrated to yield 16.3 g of the desired product as an oil.

EXAMPLE 28

Diisopropyl P-[[(2,6-dichlorophenyl)sulfonyloxy]methyl]phosphonate (Compound 55)

A solution of 20.6 g of diisopropyl P-(hydroxymethyl)-phosphonate, prepared in Example 17, and 14.7 ml of triethylamine diluted in 35 ml of ether was added dropwise over 60 minutes to a mixture of 23.97 g of 2,6-dichlorobenzenesulfonyl chloride and 140 ml of ether. The addition was mildly exothermic. The reaction was allowed to stir at room temperature overnight and then was diluted with 220 ml of ethyl acetate, the ethyl acetate solution washed with two 80 ml portions of water, dried with magnesium sulfate, filtered, and concentrated to yield 35.1 g of the crude desired product as a yellow oil. The oil was dissolved in 25 ml of methylene chloride and flash chromatographed using ethyl acetate and hexanes. Similar fractions were combined to yield 20.5 g of the desired product as an oil.

EXAMPLE 29

Diisopropyl P-[[(2-(difluoromethyoxy)-6-methylphenyl)sulfonyloxy]methyl]phosphonate (Compound 129)

A solution of 20 ml of ether, 8.6 g of diisopropyl P-(hydroxymethyl)phosphonate, prepared in Example 17, and 6.9 ml of triethylamine was added dropwise over 25 minutes to 15.2 g of crude 2-methyl-6-(difluoromethoxy)benzenesulfonyl chloride, prepared in Example 3, in 70 ml of ether. After the mild exotherm, the reaction was allowed to stir overnight at room temperature and was then diluted with 200 ml of ethyl acetate, the resulting ethyl acetate solution washed with two 80 ml portions of water, dried with magnesium sulfate, filtered, and concentrated to yield 10.2 g of the very crude desired product as a black oil. The crude product was dissolved in 10 ml of methylene chloride and flash chromatographed on Merck silica gel using ethyl acetate and hexanes. After combining similar fractions, the desired product was isolated as an amber oil in low yield.

EXAMPLE 30

Diethyl P-[[1-(N,N-diethyl-carbamoyl)-1,2,4-triazolyl-3-sulfonyloxy]methyl]phosphonate (Compound 67)

A: Diethyl P-[(1,2,4-Triazole-3-Sulfonyloxy)methyl]-phosphonate

Triethylamine, 9.2 ml, was added all at once via a syringe to a mixture of 11.0 g of 1,2,4-triazole-3-sulfonyl chloride, 11.0 g of diethyl P-(hydroxymethyl)phosphonate (Example 17) and 30 ml of dry THF that was cooled in an ice and water bath. A precipitate formed immediately. The reaction was allowed to stir overnight at room temperature, the reaction mixture was concentrated, and the concentrate was partitioned between 100 ml of ethyl acetate and 100 ml of water. The aqueous phase was back extracted with 100 ml of ethyl acetate and the combined organic extracts were dried with magnesium sulfate, filtered and concentrated to yield a clear oil which was dried at 35° C. in a vacuum oven to yield 11.0 g of the desired phosphonate intermediate.

B: Diethyl P-[[1-(N,N-diethyl-carbamoyl)-1,2,4-triazolyl-3-sulfonyloxy]methyl]phosphonate Diethylcarbamoyl chloride, 3.4 ml, was added dropwise at room temperature followed by one spatula full of 4-dimethylaminopyridine (DMAP) to a solution of 8.0 g of diethyl P-[(1,2,4-triazole-3-sulfonyloxy)methyl]phosphonate, (Example 30A), and 150 ml of THF. The solution was cooled to 5° C. and triethylamine (3.8 ml) added dropwise. A precipitate formed and the reaction warmed to room temperature. The reaction was heated to 50° C. for 20 minutes, allowed to cool and stir overnight at room temperature, and then concentrated to yield an oil. Water (100 ml) was added to the oil and the mixture extracted with ethyl acetate, dried with magnesium sulfate, filtered and concentrated. The resulting oil was triturated with a minimal amount of ethyl acetate. A solid formed which was removed by filtration and discarded. The ethyl acetate solution was concentrated to yield a solid which was crystallized from ethyl acetate and hexanes to yield 0.87 g of the desired product, mp 66°-69° C.

Using the procedure described in Example 30A, the following phosphosulfonates as described in Table I were prepared from the indicated commercially available sulfonyl chloride of Formula II and P-(hydroxymethyl)phosphonate of Formula III unless otherwise noted.

Compound 50: 2-acetoxy-3,5-dichlorobenzenesulfonyl chloride (Example 7) and diethyl P-(hydroxymethyl)phosphonate (Example 17); and Compound 91: 2-chloro-6-methylbenzenesulfonyl chloride and N,N'-[bis(di-n-propyl)] P-(hydroxymethyl)phosphonate (Example 19).

EXAMPLE 31

O-Isopropyl P-ethyl[[(2-chloro-6-methylphenyl)sulfonyloxy]methyl]phosphinate (Compound 119) and O-Isopropyl P-ethyl[[(2-methylphenyl)sulfonyloxy]methyl]phosphinate (Compound 169)

A solution of 9.90 g of 2-chloro-6-methylbenzenesulfonyl chloride, containing a small amount of 2-methylbenzenesulfonyl chloride as an impurity, dissolved in 30 ml of ether was added dropwise over 35 minutes to a solution of 8.70 g of O-isopropyl P-ethyl(hydroxymethyl)phosphinate, (Example 22), 50 ml of ether and 4.9 g of triethylamine and was allowed to stir at room temperature for 60 hours.

The reaction solution was diluted with 200 ml of ethyl acetate, washed with two 70 ml portions of water, the organic phase dried with magnesium sulfate, filtered, and concentrated to yield 7.2 g of a viscous oil. The concentrate was diluted with 6 ml of methylene chloride and flash chromatographed on Merck silica gel (230–400 mesh) using hexanes and ethyl acetate to yield 2.7 g of O-isopropyl P-ethyl[[(2-chloro-6-methylphenyl)sulfonyloxy]methyl]phosphinate (Compound 119) as a clear oil and a very small amount of O-isopropyl P-ethyl[[(2-methylphenyl)sulfonyloxy]methyl]phosphinate (Compound 169).

Using the procedure described in this example, the following phosphosulfonates as described in Table I were prepared from the indicated commercially available sulfonyl chloride of Formula II and P-(hydroxymethyl)phosphonate of Formula III unless otherwise noted:

Compound 65: 2-chloro-6-methylbenzenesulfonyl chloride and O-ethyl P-ethyl(hydroxymethyl)phosphinate (Example 21, Method B);

Compound 120: 2,6-dichlorobenzenesulfonyl chloride and O-isopropyl P-n-propyl(hydroxymethyl)phosphinate (Example 22, Method B);

Compound 121: 2-chloro-6-methylbenzenesulfonyl chloride and O-methyl P-isobutyl(hydroxymethyl)phosphinate (Example 22, Method B);

Compound 122: 2-chloro-6-methylbenzenesulfonyl chloride and O-methyl P-neopentyl(hydroxymethyl)phosphinate (Example 22, Method B); and Compound 123: 2-chloro-6-methylbenzenesulfonyl chloride and O-isopropyl P-methyl(hydroxymethyl)phosphinate (Example 22, Method B).

EXAMPLE 32

O-Isopropyl P-ethyl[[(2-chloro-6-isopropylphenyl)sulfonyloxy]methyl]phosphinate (Compound 191)

A two-phase system prepared from 25 ml of toluene and 4.64 g of 50% aqueous sodium hydroxide diluted with 5 ml of water was cooled in an ice bath before 0.5 g of benzyltriethylammonium chloride and 3.90 g of O-isopropyl-P-ethyl(hydroxymethyl)phosphinate (Example 22, Method C) was added. Then a solution of 6.12 g of 2-chloro-6-isopropylbenzenesulfonyl chloride (Example 9) in 15 ml of toluene was added and the mixture was stirred for 30 minutes. GLC analysis of an aliquot of the reaction showed that starting material was still present so an additional 2.8 g of 50% aqueous sodium hydroxide in 3 ml of water was added along with 0.2 g of benzyltriethylammonium chloride. The two-phase system was rapidly stirred for an additional 30 minutes, then the ice bath was removed and the reaction was allowed to warm to room temperature and stirred for 90 minutes. The reaction mixture was diluted with water (100 ml) and ethyl acetate (150 ml) and the separated organic phase was washed with 100 ml of water, dried with magnesium sulfate, filtered, and concentrated. The resulting 4.5 g of yellow oil was dissolved in 3 ml of methylene chloride and flash chromatographed on Merck silica gel (230–400 mesh) using ethyl acetate and hexanes mixtures. Similar fractions were combined to give 2.9 g of the desired product as a yellow oil.

Using the procedure described in this example, the following phosphosulfonates as described in Table I were prepared from the indicated commercially available sulfonyl chloride of Formula II and P-(hydroxymethyl)phosphonate or P-(hydroxymethyl)phosphinate of Formula III unless otherwise noted:

Compound 132: 2,6-dichlorobenzenesulfonyl chloride and O-isopropyl P-ethyl(hydroxymethyl)phosphinate (Example 22, Method C);

Compound 185: 2,3-dichlorobenzenesulfonyl chloride and O-isopropyl P-ethyl(hydroxymethyl)phosphinate (Example 22, Method C);

Compound 186: 2-cyanobenzenesulfonyl chloride and O-isopropyl P-ethyl(hydroxymethyl)phosphinate (Example 22, Method C);

Compound 187: 2-(trifluoromethyl)benzenesulfonyl chloride and O-isopropy P-methyl(hydroxymethyl)phosphinate (Example 22, Method C);

Compound 188: 2-cyanobenzenesulfonyl chloride and O-isopropyl P-methyl(hydroxymethyl)phosphinate (Example 22, Method C);

Compound 189: 2,4-dichloro-5-methylbenzenesulfonyl chloride and O-isopropyl P-ethyl(hydroxymethyl)phosphinate (Example 22, Method C);

Compound 190: 2,4,6-trichlorobenzenesulfonyl chloride and O-isopropyl P-ethyl(hydroxymethyl)phosphinate (Example 22, Method C);

Compound 192: 2-chloro-6-isopropylbenzenesulfonyl chloride (Example 9) and diethyl P-(hydroxymethyl)-phosphonate (Example 17);

Compound 193: 2-chloro-6-methylbenzenesulfonyl chloride and O-isopropyl P-n-propyl(hydroxymethyl)phosphinate (Example 22, Method C);

Compound 194: 2,6-dichloro-3-methylbenzenesulfonyl chloride (Example 9) and O-isopropyl P-ethyl(hydroxymethyl)-phosphinate (Example 22, Method C);

Compound 195: 2,3,4-trichlorobenzenesulfonyl chloride and O-isopropyl P-ethyl(hydroxymethyl)phosphinate (Example 22, Method C);

Compound 200: 2,5-dichlorothien-3-ylsulfonyl chloride and O-isopropyl P-ethyl(hydroxymethyl)phosphinate (Example 22, Method C);

Compound 201: 5-chloro-1,3-dimethylpyrazo-4-ylsulfonyl chloride and O-isopropyl P-ethyl(hydroxymethyl)phosphinate (Example 22, Method C);

Compound 202: 2,5-dichloro-3,6-dimethylbenzenesulfonyl chloride (Example 5B) and O-isopropyl P-ethyl(hydroxymethyl)-phosphinate (Example 22, Method C);

Compound 204: 2,4,6-triisopropylbenzenesulfonyl chloride and O-isopropyl P-ethyl(hydroxymethyl)phosphinate (Example 22, Method C);

Compound 206: 2-(methoxycarbonyl)benzenesulfonyl chloride and O-isopropyl P-ethyl(hydroxymethyl)phosphinate (Example 22, Method C); and Compound 208: 2-t-butylbenzenesulfonyl chloride (Example 4) and O-isopropyl P-ethyl(hydroxymethyl)phosphinate (Example 22, Method C).

Compound 219: 2-methyl-6-(trifluoromethyl)benzenesulfonyl chloride (Example 1) and O-isopropyl P-methyl(hydroxymethyl)phosphinate (Example 22, Method C);

Compound 221: 2-methoxy-6-(trifluoromethyl)benzenesulfonyl chloride (Example 2) and O-isopropyl P-ethyl(hydroxymethyl)phosphinate (Example 22, Method C);

Compound 224: 2-methoxy-4-(trifluoromethyl)benzenesulfonyl chloride (Example 2) and O-isopropyl P-ethyl(hydroxymethyl)phosphinate (Example 22, Method C);

Compound 231: 2-bromobenzenesulfonyl chloride and O-isopropyl P-ethyl(hydroxymethyl)phosphinate (Example 22, Method C);

Compound 233: 2-chloro-5-methylbenzenesulfonyl chloride (Example 1C) and O-isopropyl P-ethyl(hydroxymethyl)phosphinate (Example 22, Method C);

Compound 234: 1,5-dimethyl-3-(trifluoromethyl)-4-pyrazolesulfonyl chloride (Example 63) and O-isopropyl P-ethyl(hydroxymethyl)phosphinate (Example 22, Method C);

Compound 235: 1,3,5-trimethyl-4-pyrazolesulfonyl chloride (Example 63B) and O-isopropyl P-ethyl(hydroxymethyl)phosphinate (Example 22, Method C);

Compound 236: 3,5-dimethyl-4-isoxazolesulfonyl chloride and O-isopropyl P-ethyl(hydroxymethyl)phosphinate (Example 22, Method C);

Compound 242: 2,4-dimethyl-5-thiazolesulfonyl chloride and O-isopropyl P-ethyl(hydroxymethyl)phosphinate (Example 22, Method C);

Compound 246: 2,5-dichloro-3-methyl-4-thiophenesulfonyl chloride (Example 61) and O-isopropyl P-ethyl(hydroxymethyl)phosphinate (Example 22, Method C);

Compound 248: 8-chloro-1-naphthalenesulfonyl chloride (Example 64) and O-isopropyl P-ethyl(hydroxymethyl)phosphinate (Example 22, Method C);

Compound 249: benzo-2,1,3-thiadiazole-4-sulfonyl chloride and O-isopropyl P-ethyl(hydroxymethyl)phosphinate (Example 22, Method C);

Compound 251: 5-chloro-1-methyl-3-isopropyl-4-pyrazolesulfonyl chloride (Example 62) and O-isopropyl P-ethyl(hydroxymethyl)phosphinate (Example 22, Method C);

Compound 252: 5-chloro-1,3-dimethyl-4-pyrazolesulfonyl chloride and O-isopropyl P-methyl(hydroxymethyl)phosphinate (Example 22, Method C);

Compound 253: 2-ethoxy-4-(trifluoromethyl)benzenesulfonyl chloride Example 65) and O-isopropyl P-ethyl(hydroxymethyl)phosphinate (Example 22, Method C);

Compound 254: 2-ethoxy-6-(trifluoromethyl)benzenesulfonyl chloride Example 65) and O-isopropyl P-ethyl(hydroxymethyl)phosphinate (Example 22, Method C);

Compound 256: 5-chloro-3-ethyl-1-methyl-4-pyrazolesulfonyl chloride (Example 62) and O-isopropyl P-ethyl(hydroxymethyl)phosphinate (Example 22, Method C);

EXAMPLE 33

O-Isopropyl P-methyl[[(2-chloro-6-isopropylphenyl)sulfonyloxy]-methyl]phosphinate (Compound 197)

To a solution of 2.5 g of 2-chloro-6-isopropylbenzenesulfonyl chloride (Example 9) and 1.15 g of O-isopropyl P-methyl(hydroxymethyl)phosphinate (Example 22, Method C) dissolved in 35 ml of methylene chloride at 5° C. was added 0.23 g of benzyltriethylammonium chloride followed by 2.5 ml of 20% aqueous sodium hydroxide. The reaction mixture was allowed to warm to room temperature over 1 hour then was stirred overnight. The pale yellow mixture was diluted with saturated ammonium chloride, 25 ml, and water, 25 ml, then the layers were separated and the aqueous phase was extracted with three 50 ml portions of methylene chloride. The combined organic layers were washed with brine, dried with magnesium sulfate, filtered, and concentrated to give 3.6 of a semisolid which was flash chromatographed on silica gel using 70% ethyl acetate/30% hexanes. Similar fractions were combined to give a white solid which was recrystallized from ether and hexanes to yield 1.0 g of desired product, mp 69.5°–70.5° C.

Using the procedure described in this example, the following phosphosulfonates as described in Table I were prepared from the indicated commercially available sulfonyl chloride of Formula II and P-(hydroxymethyl)phosphonate or P-(hydroxymethyl)phosphinate of Formula III unless otherwise noted:

Compound 196: 2,6-dichlorobenzenesulfonyl chloride and O-isopropyl P-methyl(hydroxymethyl)phosphinate (Example 22, Method C);

Compound 198: 2-chlorobenzenesulfonyl chloride and O-isopropyl P-methyl(hydroxymethyl)phosphinate (Example 22, Method C);

Compound 199: 2,6-dichloro-3-methylbenzenesulfonyl chloride (Example 9) and O-isopropyl P-methyl(hydroxymethyl)-phosphinate (Example 22, Method C);

Compound 203: 2-(methoxycarbonyl)benzenesulfonyl and O-isopropyl P-methyl(hydroxymethyl)phosphinate (Example 22, Method C);

Compound 209: 2-methyl-6-(ethoxycarbonyl)benzenesulfonyl chloride (Example 1C) and O-isopropyl P-methyl(hydroxymethyl)-phosphinate (Example 22, Method C); and Compound 211: 2-methyl-6-(isopropyloxycarbonyl)-benzenesulfonyl chloride (Example 1C) and O-isopropyl P-methyl(hydroxymethyl)phosphinate (Example 22, Method C).

Compound 218: 2-methyl-6-(trifluoromethyl)benzenesulfonyl chloride (Example 1) and O-isopropyl P-ethyl(hydroxymethyl)phosphinate (Example 22, Method C);

Compound 222: 2-methoxy-6-(trifluoromethyl)benzenesulfonyl chloride (Example 2) and O-isopropyl P-methyl(hydroxymethyl)phosphinate (Example 22, Method C);

Compound 227: 2-methoxy-4-(trifluoromethyl)benzenesulfonyl chloride (Example 2) and O-isopropyl P-methyl(hydroxymethyl)phosphinate (Example 22, Method C);

Compound 239: 2,6-dibromobenzenesulfonyl chloride (Example 1C) and O-isopropyl P-ethyl(hydroxymethyl)phosphinate (Example 22, Method C);

Compound 243: 2,6-dibromobenzenesulfonyl chloride (Example 1C) and diethyl P-(hydroxymethyl)phosphonate (Example 17);

Compound 245: 2,5-dichloro-4-methyl-3-thiophenesulfonyl chloride (Example 61) and O-isopropyl P-ethyl(hydroxymethyl)phosphinate (Example 22, Method C);

Compound 250: 2,4-dimethyl-5-thiazolesulfonyl chloride and diethyl P-(hydroxymethyl)phosphonate (Example 17).

EXAMPLE 34

O-Isopropyl P-ethyl[[(2-trifluoromethylphenyl)sulfonyloxy]methyl]phosphinate (Compound 170)

To a suspension of hexanes washed NaH (1.28 g, 60% dispersion in oil) in 30 ml of THF was added dropwise over 10 minutes 4.3 g of O-isopropyl P-ethyl(hydroxymethyl)phosphinate (Example 22, Method C) in 10 ml of THF. The evolution of hydrogen occurred during the addition and the resulting suspension was stirred at room temperature for 45 minutes. It was then transferred to an addition funnel and added portionwise over 1 hour to a cooled, −30° C., solution of 12.23 g of 2-(trifluoromethyl)benzenesulfonyl chloride in 30 ml of THF. The reaction temperature was kept between −30° C. and −10° C. during the addition then the reaction was slowly warmed to room temperature and stirred overnight. The reaction mixture was diluted with 200 ml of ethyl acetate and 100 ml of water and the separated organic phase was dried with magnesium sulfate, filtered, and concentrated to yield 11.0 g of a clear oil. The oil was then dissolved in 5 ml of methylene chloride and flash chromatographed on Merck silica gel using blends of ethyl acetate and hexanes. Similar fractions were combined to yield 3.5 g of product as an oil.

Using the procedure described in this example, the following phosphosulfonates as described in Table I were prepared from the indicated commercially available sulfonyl chloride of Formula II and P-(hydroxymethyl)phosphinate of Formula III unless otherwise noted:

Compound 181: 2,3-dichlorobenzenesulfonyl chloride and O-isopropyl P-ethyl(hydroxymethyl)phosphinate (Example 22, Method C);

Compound 182: 2,4,6-trimethylbenzenesulfonyl chloride and O-isopropyl P-ethyl(hydroxymethyl)phosphinate (Example 22, Method C); and Compound 183: 2-isopropylbenzenesulfonyl chloride (Example 4) and O-isopropyl P-ethyl(hydroxymethyl)phosphinate (Example 22, Method C).

EXAMPLE 35

O-Isopropyl P-Ethyl[[(2,6-dichlorophenyl)sulfonyloxy]methyl]-phosphinate (Compound 132)

A solution of 19.6 g of 2,6-dichlorobenzenesulfonyl chloride dissolved in 70 ml of methylene chloride was added dropwise over 40 minutes to a mixture of 25 ml of methylene chloride, 15.0 ml of triethylamine, 1.0 g of DMAP, and 16.5 g of O-isopropyl P-ethyl(hydroxymethyl)phosphinate, (Example 22, Method A). The addition caused a mild exotherm and the reaction was allowed to stir at room temperature overnight. The reaction mixture was then washed with two 50 ml portions of water, the phases separated, the organic phase dried with magnesium sulfate, filtered, and concentrated to yield 19.6 g of the desired product as a yellow oil. The crude product was diluted with 10 ml of methylene chloride and flash chromatographed using blends of ethyl acetate and hexanes. Similar fractions were combined and rechromatographed to yield 0.95 g of the desired product.

EXAMPLE 36

O-Ethyl P-methyl[[(2-(trifluoromethyl)phenyl)sulfonyloxy]methyl]phosphinate (Compound 103)

A solution of 8 ml of triethylamine diluted with 25 ml of THF was slowly added dropwise over two hours to a mixture of 11.2 g of 2-(trifluoromethyl)benzenesulfonyl chloride, 6.05 g of O-ethyl P-methyl(hydroxymethyl)phosphinate, (Example 22, Method B), and 60 ml of THF. A white precipitate began to form shortly after the addition of the triethylamine solution was begun. No significant exotherm occurred and the reaction was allowed to stir overnight. The reaction mixture was concentrated and the concentrate was partitioned between 220 ml of ethyl acetate and 50 ml of water. The organic phase was washed with an additional 50 ml of water, dried with magnesium sulfate, gravity filtered, and concentrated to yield an orange solid. The solid was flash chromatographed on silica gel using ethyl acetate to yield 2.2 g of the desired product, melting point 91°–92.5° C.

Using the procedure described in this example, the following phosphosulfonates as described in Table I were prepared from the indicated commercially available sulfonyl chloride of Formula II and P-(hydroxymethyl)phosphinate of Formula III unless otherwise noted:

Compound 89: 2-chloro-6-methylbenzenesulfonyl chloride and O-ethyl P-phenyl(hydroxymethyl)phosphinate (Example 22, Method B);

Compound 90: 2-(trifluoromethyl)benzenesulfonyl chloride and O-ethyl P-phenyl(hydroxymethyl)phosphinate (Example 22, Method B);

Compound 99: 2-chloro-6-methylbenzenesulfonyl chloride and O-ethyl P-isopropyl(hydroxymethyl)phosphinate (Example 22, Method B);

Compound 101: 2-(trifluoromethyl)benzenesulfonyl chloride and O-ethyl P-isopropyl(hydroxymethyl)phosphinate (Example 22, Method B); and Compound 102: 2-chloro-6-methylbenzenesulfonyl chloride and O-ethyl P-methyl(hydroxymethyl)phosphinate (Example 22, Method B).

EXAMPLE 37

O-Isopropyl P-ethyl[[(2-chlorophenyl)sulfonyloxy]methyl]phosphinate (Compound 171)

A solution of 4.10 g of O-isopropyl P-ethyl-(hydroxymethyl)phosphinate, prepared in Example 22, Method A, 4.4 ml of triethylamine and 20 ml of methylene chloride was added dropwise over 40 minutes to a mixture of 25 ml of methylene chloride, 5.75 g of 2-chlorobenzenesulfonyl chloride, and 0.1 g of DMAP. The reaction temperature was kept between 15° C. and 28° C. during the addition. The reaction was allowed to stir at room temperature for eight days and was then diluted with 100 ml of water and 100 ml of methylene chloride. The organic phase was separated, dried with magnesium sulfate, filtered and concentrated to yield the crude product. Phosphorus NMR indicated two products in a 5:1 ratio. The crude product was dissolved in 30 ml of 1,2-dichloroethane and then 1.8 g of 3-chloroperoxybenzoic acid (MCPBA) was added. The reaction mixture was refluxed for three hours, allowed to cool to room temperature and stand overnight. The reaction mixture was diluted with 100 ml of methylene chloride. Then 100 ml of 10% of sodium sulfite solution was added, followed by the careful addition of 100 ml of saturated sodium bicarbonate solution in small portions. Once the foaming ceased small portions of solid sodium bicarbonate were added until all foaming ceased. The phases were separated, the organic phase washed with 100 ml of water, dried with magnesium sulfate, filtered and concentrated to yield 3.3 g of the crude product as an oil. The oil was dissolved in 4 ml of methylene chloride and flash chromatographed on Merck silica gel (230-400 mesh) using blends of hexanes and ethyl acetate ranging from 1/1 to 0/100 hexanes/ethyl acetate, respectively. Similar fractions were combined and concentrated to yield 2.5 g of the desired product.

Using the procedure described in this example, the following phosphosulfonates as described in Table I were prepared from the indicated commercially available sulfonyl chloride of Formula II and the P-(hydroxymethyl)phosphinate of Formula III unless indicated otherwise:

Compound 170: 2-(trifluoromethyl)benzenesulfonyl chloride and O-isopropyl P-ethyl(hydroxymethyl)phosphinate, (Example 22, Method A), except that DMAP and the oxidation step were omitted and the reaction was stirred overnight instead of 8 days;

Compound 172: 2-(trifluoromethoxy)benzenesulfonyl chloride and O-isopropyl P-ethyl(hydroxymethyl)phosphinate, (Example 22, Method A), except that tetrahydrofuran (THF) was used as the reaction solvent in the first reaction, no oxidation was performed and the reaction was run overnight instead of 8 days;

Compound 173: Benzenesulfonyl chloride and O-isopropyl P-ethyl(hydroxymethyl)phosphinate, (Example 22, Method A), except that methylene chloride was used as the solvent in the oxidation step, the oxidation was conducted at room temperature and the first reaction was run overnight instead of 8 days;

Compound 174: 1-naphthylenesulfonyl chloride and O-isopropyl P-ethyl(hydroxymethyl)phosphinate, (Example 22, Method A), except that the oxidation step was omitted and the reaction was run overnight instead of 8 days;

Compound 175: 2-nitrobenzenesulfonyl chloride and O-isopropyl P-ethyl(hydroxymethyl)phosphinate, (Example 22, Method B), except that the first reaction was run overnight instead of 8 days;

Compound 176: 2,6-dimethylbenzenesulfonyl chloride and O-isopropyl P-ethyl(hydroxymethyl)phosphinate, (Example 22, Method B), except that the oxidation step was omitted and the reaction was run overnight instead of 8 days;

Compound 177: 2,5-dichlorobenzenesulfonyl chloride and O-isopropyl P-ethyl(hydroxymethyl)phosphinate, (Example 22, Method B), except that the first reaction was run overnight instead of 8 days.

EXAMPLE 38

O-Isopropyl P-Ethyl[[(2-methoxyphenyl)sulfonyloxy]methyl]phosphinate (Compound 178)

A solution of 5.65 g of O-isopropyl P-ethyl(hydroxymethyl)phosphinate, (Example 22, Method B), 7.0 ml of triethylamine and 25 ml of methylene chloride was added dropwise over 45 minutes to a mixture of 50 ml of methylene chloride, 8.03 g of crude 2-methoxybenzenesulfonyl chloride, (Example 4), and 0.1 g of DMAP. The reaction temperature was kept between 20° C. and 27° C. during the addition. The reaction was allowed to stir at room temperature for four days and was then diluted with 80 ml of water and 100 ml of methylene chloride. The phases were separated, the organic phase dried with magnesium sulfate, filtered and concentrated to yield 7.8 g of the crude product as a brown oil. Phosphorus NMR indicated two products in a 1:1 ratio. The crude product was dissolved in 35 ml of acetic acid and 12 ml of 30% hydrogen peroxide solution was added. After stirring for 10 minutes, the reaction temperature was slowly increased to 90° C. for 2.5 hours. The reaction was allowed to cool to room temperature and stand overnight and was then poured onto 100 g of ice and the mixture diluted with 100 ml of water. After the ice had melted, the aqueous mixture was extracted with 200 ml of ethyl acetate, the phases separated, the organic phase washed with 100 ml of saturated sodium bicarbonate solution, dried with magnesium sulfate, filtered, and concentrated to yield the crude product as an oil. The oil was dissolved in 4 ml of methylene chloride and flash chromatographed on Merck silica gel (230-400 mesh) using blends of hexanes and ethyl acetate ranging from 30/70 to 10/90 hexanes and ethyl acetate, respectively. Similar fractions were combined and concentrated to yield 0.5 g of the desired product.

EXAMPLE 39

Di-n-propyl[[(2-chloro-6-methylphenyl)sulfonyloxy]methyl]phosphine oxide (Compound 98)

A solution of 7.20 g of 2-chloro-6-methylbenzenesulfonyl chloride dissolved in 30 ml of THF was added dropwise over 30 minutes to a reaction mixture 5.80 g of di-n-propyl(hydroxymethyl)-phosphine oxide, (Example 23), 30 ml of THF, and 4.04 g of triethylamine. The addition caused a mild exotherm and the reaction was allowed to stir at room temperature over the weekend. Most of the THF was removed and the resulting material was partitioned between 200 ml of ethyl acetate and 70 ml of water, the organic phase rewashed with an additional 70 ml of water, dried with magnesium sulfate, filtered and concentrated to yield 6.5 g of the crude desired product as a dark tan oil. The crude product was diluted with 4 ml of methylene chloride and flash chromatographed on Merck silica gel (230-400 mesh) using blends of isopropanol and ethyl acetate, similar fractions were combined and concentrated under reduced pressure to yield the partially purified product. This material was dissolved in 150 ml of ethyl acetate, washed with three 50 ml portions of water, dried with magnesium sulfate, filtered and concentrated to yield 2.4 g of the desired product as a white solid: melting point 51°-53° C.

Using the procedure described in this example, the following phosphosulfonates as described in Table I were prepared from the indicated commercially available sulfonyl chloride of Formula II and P-(hydroxymethyl)phosphine oxide of Formula III unless otherwise noted:

Compound 92: 2-chloro-6-methylbenzenesulfonyl chloride and diethyl(hydroxymethyl)phosphine oxide (Example 23) and Compound 100: 2-(trifluoromethyl)benzenesulfonyl chloride and di-n-propyl(hydroxymethyl)phosphine oxide (Example 23).

EXAMPLE 40

Diisopropyl P-[[(2-methoxy-6-(trifluoromethyl)phenyl)sulfonyloxy]methyl]-phosphonate (Compound 153), and Diisopropyl P-[[(2-methoxy-4-(trifluoromethyl)phenyl)sulfonyloxy]methyl]phosphonate, (Compound 154)

The crude sulfonyl chloride, prepared in Example 2, was reacted with diisopropyl P-(hydroxymethyl)phosphonate, prepared in Example 17, as described in Example 24. The two major sulfonate products were isolated via flash chromatography on Merck silica gel (230-400 mesh) eluting with hexanes and ethyl acetate. Similar fractions were combined and concentrated to yield 5.8 g of the desired diisopropyl P-[[(2-methoxy-6-(trifluoromethyl)phenyl)sulfonyloxy]methyl]phosphonate, (Compound 153), and 0.85 g of diisopropyl P-[[(2-methoxy-4-(trifluoromethyl)phenyl)sulfonyloxy]methyl]phosphonate, (Compound 154).

EXAMPLE 41

Diethyl P-[[(2-methoxyphenyl)sulfonyloxy]methyl]phosphonate (Compound 86) and Diethyl P-[[(5-Chloro-2-methoxyphenyl)sulfonyloxy]methyl]-phosphonate (Compound 85)

2-Methoxythiophenol was oxidezed to the corresponding sulfonyl chloride as described in Example 4. After an extractive workup, GLC analysis indicated three components were present in a 67:13:20 ratio. These components were the desired 2-methoxybenzenesulfonyl chloride, 5-chloro-2-methoxybenzenesulfonyl chloride and 2-methoxyphenyldisulfide, in that order. The crude sulfonyl chloride mixture was reacted with diethyl P-(hydroxymethyl)phosphonate (Example 17) as described in Example 24. The desired products were isolated via flash chromatography using solvent blends ranging from 2/1 hexanes/ethyl acetate to 9/1 ethyl acetate/isopropanol. Similar fractions were combined and concentrated to yield 4.0 g of the desired diethyl P-[[(2-methoxyphenyl)sulfonyloxy]methyl]-phosphonate (Compound 86) and 0.55 of diethyl P-[[(5-chloro-2-methoxyphenyl)sulfonyloxy]methyl]phosphonate (Compound 85).

EXAMPLE 42

Diethyl P-[[(2,6-dimethoxyphenyl)sulfonyloxy]methyl]phosphonate (Compound 125) and Diethyl P-[[(3-chloro-2,6-dimethoxyphenyl)sulfonyloxy]methyl]phosphonate (Compound 124)

Lithio-1,3-dimethoxybenzene was prepared and reacted with sulfur dioxide gas as described in Example 2. The resulting lithium sulfinate was converted to the sulfonyl chloride by reacting the lithium sulfinate with 0.77 equivalent of sulfuryl chloride. GLC analysis indicated two major components were present. The crude sulfonyl chloride was reacted as described in Example 25. After an extractive workup, the desired products were isolated via flash chromatography using a blend of eluting solvents ranging from 2/1 hexanes/ethyl acetate to straight ethyl acetate. Similar fractions were combined and concentrated to yield 1.5 g of diethyl P-[[(3-chloro-2,6-dimethoxyphenyl)sulfonyloxy]methyl]phosphonate (Compound 124) and 0.18 g of the desired diethyl P-[[(2,6-dimethoxyphenyl)sulfonyloxy]methyl]-phosphonate (Compound 125).

EXAMPLE 43

Preparation and Separation of the Two Diastereomers of 2-Oxo-4-methyl-2-[[(2-chloro-6-methylphenyl)sulfonyloxy]methyl]-1,3,2-dioxaphosphorinan (Compounds 139 and 140)

A solution of 12.65 g of 2-(hydroxymethyl)-2-oxo-4-methyl-1,3,2-dioxaphosphorinan, (Example 21), was prepared by dissolving the phosphorinan in a mixture of 40 ml of p-dioxane, 30 ml of ether, and 20 ml of THF with stirring and gentle heating on a steam bath. When all of the phosphorinan had dissolved, 11.8 ml of triethylamine was added to the cooled (room temperature) phosphorinan solution. The phosphorinan/base solution was then added dropwise to a solution of 16.4 g of 2-chloro-6-methylbenzenesulfonyl chloride in 70 ml of ether over 50 minutes. The addition caused a mild exotherm and the reaction was allowed to stir overnight at room temperature. The reaction solution was gravity filtered and the filter cake was rinsed with 75 ml of ethyl acetate, the combined filtrates concentrated, the concentrate partitioned between 300 ml of ethyl acetate and 100 ml of water, the phases separated, the organic phase rewashed with an additional 100 ml of water, dried with magnesium sulfate, filtered and concentrated to yield 18.2 g of the crude desired product as an off white solid. Phosphorus NMR indicated two diastereomers were present. The product was purified by flash chromatographing 7.4 g of the crude reaction product, dissolved in 12 ml of methylene chloride, on Merck silica gel (230-400 mesh) eluting with blends of hexanes and ethyl acetate. Similar fractions were combined and concentrated to yield the two diastereomers: isomer A, 3.05 g, mp 113°-114° C. (Compound 139) and isomer B, 1.46 g, mp 76.5°-78° C. (Compound 140).

Using the procedure described in this example, the following phosphosulfonates as described in Table IB were prepared from the indicated commercially available sulfonyl chloride of Formula II and the indicated 2-(hydroxymethyl)-2-oxo-1,3,2-dioxaphosphorinan of Formula III, prepared in Example 21, unless otherwise noted:

Compound 144 (isomer A): 2-(trifluoromethyl)benzenesulfonyl chloride and 2-(hydroxymethyl)-2-oxo-4-methyl-1,3,2-dioxaphosphorinan;

Compound 145 (isomer B): 2-(trifluoromethyl)benzenesulfonyl chloride and 2-(hydroxymethyl)-2-oxo-4-methyl-1,3,2-dioxaphosphorinan;

Compound 148: 2-chloro-6-methylbenzenesulfonyl chloride and 2-(hydroxymethyl)-2-oxo-5,5-dimethyl-1,3,2-dioxaphosphorinan, using a 1:1:1:1 solvent mixture of methylene chloride, tetrahydrofuran, ether and p-dioxane and adding 0.15 g of DMAP;

Compound 149: 2-chloro-6-methylbenzenesulfonyl chloride and 2-(hydroxymethyl)-2-oxo-1,3,2-dioxaphosphorinan, using a 1:1 solvent mixture of ether and methylene chloride and adding 0.1 g of DMAP;

Compound 150 (isomer A): 2-chloro-6-methylbenzenesulfonyl chloride and 2-(hydroxymethyl)-2-oxo-4,6-dimethyl-1,3,2-dioxaphosphorinan, using a 1:1 solvent mixture of ether and methylene chloride and adding 0.15 g of DMAP;

Compound 151: 2-(trifluoromethyl)benzenesulfonyl chloride and 2-(hydroxymethyl)-2-oxo-5,5-dimethyl-1,3,2-dioxaphosphorinan, using a 1:1 solvent mixture of ether and methylene chloride and adding 0.2 g of DMAP;

Compound 152 (isomer B): 2-chloro-6-methylbenzenesulfonyl chloride and 2-(hydroxymethyl)-2-oxo-4,6-dimethyl-1,3,2-dioxaphosphorinan, using a 1:1 solvent mixture of ether and methylene chloride and adding 0.15 g of DMAP;

Compound 155 (isomer A): 2-(trifluoromethyl)benzenesulfonyl chloride and 2-(hydroxymethyl)-2-oxo-4,6-dimethyl-1,3,2-dioxaphosphorinan, using methylene chloride as solvent and adding 0.1 g of DMAP; and Compound 156 (mixture of isomers A & B): 2-(trifluoromethyl)benzenesulfonyl chloride and 2-(hydroxymethyl)-2-oxo-4,6-dimethyl-1,3,2-dioxaphosphorinan, using methylene chloride as solvent and adding 0.1 g of DMAP.

PREPARATION OF THE P-(SULFONYLOXYMETHYL)-PHOSPHONOYL CHLORIDES AND THE P-(SULFONYLOXYMETHYL)-PHOSPHINOYL CHLORIDES OF FORMULAS IX AND X

EXAMPLE 44

O-Isopropyl P-[[(2-chloro-6-methylphenyl)sulfonyloxy]methyl]-phosphonoyl chloride (Compound 130)

Phosphorous pentachloride, 19.4 g, was added in small portions over 5 minutes to a mixture of 130 ml of methylene chloride and 32.0 of diisopropyl P-[[(2-chloro-6-methylphenyl)sulfonyloxy]methyl]phosphonate (Compound 72). The addition caused a mild exotherm to 32° C. The reaction slowly cooled to room temperature and was allowed to stir overnight. The progress of the reaction was determined by removing a 3 ml aliquot, concentrating it and taking a phosphorus NMR. The $^{31}$P NMR indicated that the reaction was 85% complete. An additional 1.5 g of phosphorous pentachloride was added and the reaction was heated to reflux for 90 minutes. The reaction was then concentrated, the concentrate dissolved in 100 ml of toluene and then reconcentrated to yield the desired product as a yellow liquid.

Using the above procedure, the following phosphonoyl chlorides of Formula IX were prepared from the indicated compounds except as noted:

O-isopropyl P-[[(4-chloro-2,6-dimethylphenyl)sulfonyloxy]methyl]phosphonoyl chloride was prepared from Compound 131;

O-isopropyl P-[[(2,4-dichloro-6-methylphenyl)sulfonyloxy]methylphosphonoyl chloride was prepared from Compound 134;

O-isopropyl P-[[(2,4-dichloro-6-methoxyphenyl)sulfonyloxy]methyl]phosphonoyl chloride was prepared from Compound 137;

O-isopropyl P-[[(2,5-dichloro-3,6-dimethylphenyl)sulfonyloxy]methyl]phosphonoyl chloride was prepared from Compound 146;

O-isopropyl P-[[(2-methoxy-6-(trifluoromethyl)phenylsulfonyloxy]methyl]phosphonoyl chloride was prepared from Compound 153; and O-isopropyl P-[[(2-chloro-6-isopropylphenyl)sulfonyloxy]methyl]phosphonoyl chloride was prepared from Compound 184.

EXAMPLE 45

O-Ethyl P-[[(2-chloro-6-methylphenyl)sulphonyloxy]methyl]-phosphonoyl chloride

Diethyl P-[[(2-chloro-6-methylphenyl)sulfonyloxy]methyl]phosphonate (20.0 g) (Compound 45), 14.1 g of phosphorous pentachloride and 70 ml of toluene were heated to reflux for seven hours and then allowed to cool to room temperature and stand overnight. A four ml reaction aliquot was concentrated and 10 ml of toluene was added and subsequently removed. Analysis of the aliquot by phosphorus NMR indicated that the reaction was complete. The remainder of the reaction mixture was concentrated, 100 ml of toluene added and subsequently removed along with the residual phosphorus oxychloride by-product to yield 19.3 g of the desired product as a yellow oil.

Using the above procedure, the following phosphonoyl chlorides of Formula IX were prepared from the indicated compounds except as otherwise noted:

O-ethyl P-[[(2-(trifluoromethyl)phenyl)sulphonyloxy]methyl]phosphonoyl chloride was prepared from Compound 30;

O-ethyl P-[[(2,6-dichlorophenyl)sulphonyloxy]methyl]phosphonoyl chloride was prepared from Compound 44.

O-ethyl P-[[(2,5-dichloro-4-methyl-3-thienyl)sulfonyloxy]methyl]phosphonoyl chloride was prepared from Compound 244 only the reaction temperature was room temperature.

EXAMPLE 46

O-Methyl P-[[(2-chloro-6-methylphenyl)sulfonyloxy]methyl]-phosphonoyl chloride

Eleven grams of phosphorous pentachloride was added all at once to a mixture of 16.0 g of dimethyl P-[[(2-chloro-6-methylphenyl)sulfonyloxy]methyl]-phosphonate (Compound 115) and 80 ml of methylene chloride. A mild exotherm resulted, and the reaction was allowed to stir overnight at room temperature. Then, the reaction was refluxed for 3.5 hours and allowed to cool to room temperature. A 3 ml aliquot of the reaction mixture was concentrated and examined by phosphorus NMR which indicated that the reaction was 95% complete. The reaction was again allowed to stir overnight at room temperature. Then, the reaction was concentrated, the concentrate dissolved with 100 ml of toluene, the toluene removed and the concentrate placed under high vacuum with stirring at 45° C. to yield 14.5 g of the desired product as a yellow liquid.

EXAMPLE 47

O-Isopropyl P-[[(2-(Trifluoromethyl)phenyl)sulfonyloxy]methyl]-phosphonoyl chloride Phosphorous pentachloride, 13.5 g, was added all at once to 100 ml of methylene chloride and 23.4 of diisopropyl P-[[(2-(trifluoromethyl)phenyl)sulfonyloxy]methyl]phosphonate (Compound 143). The addition did not cause an exotherm. The reaction was allowed to stir at room temperature overnight and was monitored by removing a 3 ml aliquot from the reaction mixture, concentrating it checking it by phosphorus NMR. The $^{31}$P NMR indicated that the reaction was 90% complete. An additional 1.6 g of phosphorous pentachloride was added and the reaction was allowed to again stir at room temperature overnight. The reaction was concentrated, the concentrate dissolved in 100 ml of toluene and the resulting solution reconcentrated to yield 20.9 of the desired product as a yellow liquid.

EXAMPLE 48

O-Isopropyl P-[[(2-methyl-6-(trifluoromethyl)phenyl)sulfonyloxy]-methyl]phosphonoyl chloride A: Diisopropyl P-[[(2-methyl-6-(trifluoromethyl)-phenyl)sulfonyloxyl]methyl]phosphonate A solution of 5.25 g of diisopropyl P-(hydroxymethyl)-phosphonate, (Example 17), 4.1 ml of triethylamine, and 20 ml of ether was added dropwise over 10 minutes to 30 ml of ether and 6.3 g of 2-methyl-6-(trifluoromethyl)-benzenesulfonyl chloride (Example 1). The addition was mildly exothermic and the reaction was allowed to stir at room temperature overnight. The reaction solution was then diluted with 200 ml of ethyl acetate and washed with two 100 ml portions of water. The separated organic phase was dried with magnesium sulfate, filtered and concentrated. Yield was 8.3 g of a brown oil. The desired phosphonate was isolated via chromatography on Merck silica gel (230–400 mesh) eluting with hexanes and ethyl acetate. Yield was 1.9 g of the desired phosphonate.

B: O-Isopropyl P-[[(2-methyl-6-(trifluoromethyl)-phenyl)sulfonyloxy]methyl]phosphonoyl chloride Phosphorous pentachloride, 1.04 g, was added all at once to 25 ml of methylene chloride and 1.93 g of diisopropyl P-[[(2-methyl-6-(trifluoromethyl)phenyl)sulfonyloxy]methyl]phosphonate (Example 48A) and allowed to stir at room temperature overnight. A 3 ml aliquot was removed, concentrated and checked by −P NMR which indicated that the reaction was 80% complete. An additional 0.1 g of phosphorous pentachloride was added and the reaction was again allowed to stir at room temperature overnight. Again, a 3 ml reaction aliquot was removed and checked by phosphorus NMR which indicated that the starting material was no longer present. The reaction was concentrated, the concentrate dissolved in 50 ml of toluene and the toluene solution concentrated to yield 1.8 g of the crude desired product as a yellow liquid.

EXAMPLE 49

O-Isopropyl P-[[(2,6-dichlorophenyl)sulfonyloxy]methyl]phosphonoyl chloride

Phosphorous pentachloride, 11.6 g, was added all at once to 100 ml of methylene chloride and 19.3 g of diisopropyl P-[[(2,6-dichlorophenyl)sulfonyloxy]methyl]phosphonate (Compound 55). The addition caused a mild exotherm and the phosphorous pentachloride dissolved in the reaction mixture within five minutes. The reaction slowly cooled to room temperature and was allowed to stir over the weekend. An additional 1.5 g of phosphorous pentachloride was then added and the reaction heated to reflux for 4.5 hours. The reaction was concentrated, the concentrate dissolved in 100 ml of toluene, then reconcentrated to yield 17.2 g of the desired product as a yellow liquid.

Using the above procedure, the following phosphonoyl chlorides of Formula IX were prepared form the indicated compounds except as noted:

O-isopropyl P-[[(2-chlorophenyl)sulfonyloxy]methyl]-phosphonoyl chloride was prepared from Compound 226;

O-isopropyl P-[[(2-ethoxy-6-(trifluoromethyl)phenyl)-sulfonyloxy]methyl]phosphonoyl chloride was prepared from Compound 257.

EXAMPLE 50

P-[[(2-Chloro-6-methylphenyl)sulfonyloxy]methyl]-phosphonoyl dichloride

A solution of 24.9 g of diisopropyl P-[[(2-chloro-6-methylphenyl)sulfonyloxy]methyl]phosphonate (Compound 72), 80 ml of toluene and 16.2 g of phosphorous pentachloride was heated to 80° C. for four hours. The temperature was then increased to 90° C. and held at that temperature for 14 hours. A 5 ml reaction aliquot was concentrated and examined by phosphorus NMR which indicated that the reaction was complete. The reaction solution was concentrated, 100 ml of toluene added and the mixture reconcentrated to yield 22.5 g of the desired product as a black oil.

EXAMPLE 51

P-Ethyl[[(2-chloro-6-methylphenyl)sulfonyloxy]methyl]phosphinoyl chloride

A mixture of 20.0 g of O-isopropyl P-ethyl[[2-chloro-6-methylphenyl)sulfonyloxy]methyl]phosphinate (Compound 119), 80 ml of 1,2-dichloroethane and 4.6 ml of thionyl chloride was heated to 50° C. for four hours. $^{31}$P NMR analysis of an aliquot of the reaction showed that one third of the starting material was still present so the reaction was heated to 50° C. for 1.5 hours, cooled and let stand at room temperature for 65 hours, heated again to 50° C. for 4 hours and let stand overnight. $^{31}$P NMR indicated that starting material was still present so 2 ml of thionyl chloride was added and the reaction was heated to 50° C. for 3.5 hours. The reaction mixture was concentrated under reduced pressure to yield 19.4 g of the desired phosphinoyl chloride which was shown to be 95% pure by $^{31}$P NMR. Using the above procedure, the following phosphinoyl chloride of Formula IX was prepared form the indicated compound: P-methyl[[(2-chloro-6isopropylphenyl)sulfonyloxy]methyl]phosphinoyl chloride was prepared from Compound 197 (Example 33).

EXAMPLE 52

P-Ethyl[[(2-chloro-6-methylphenyl)sulfonyloxy]methyl]phosphinoyl chloride

Phosphorus pentachloride, 8.32 g, was added in approximately three equal portions over 15 minutes to a mixture at 20° C. of 11.4 g of O-isopropyl P-ethyl[[(2-chloro-6-methylphenyl)-sulfonyloxy]methyl]phosphinate (Compound 119) and 30 ml of 1,2-dichloroethane. Each addition of the phosphorus pentachloride caused a mild exotherm, but the reaction temperature did not exceed 32° C. The reaction slowly cooled to room temperature and was allowed to stir for 72 hours. A 3 ml aliquot of the reaction mixture was concentrated and analyzed by $^{31}$P NMR. The $^{31}$P NMR indicated that the reaction was complete. The remainder of the reaction mixture was concentrated, 100 ml of toluene was added, the mixture reconcentrated and then high vacuum was pulled on the sample at 55° C. for one hour to yield 10.5 g of the crude desired product.

PREPARATION OF THE PHOSPHOSULFONATES OF FORMULA I FROM THE CORRESPONDING PHOSPHONOYL AND PHOSPHINOYL CHLORIDES OF FORMULAS IX AND X

EXAMPLE 53

O-Ethyl-O-isopropyl P-[[(2-chloro-6-methylphenyl)sulfonyloxy]methyl]phosphonate (Compound 96)

A solution of 5.0 g of O-ethyl P-[[(2-chloro-6-methylphenyl)sulfonyloxy]methyl]phosphonoyl chloride, prepared in Example 45, and 17 ml of ether was cooled to 5° C. and a solution of 0.99 gram of 2-propanol dissolved in 5 ml of ether was added dropwise over a five minute period. A solution of 3 ml of triethylamine dissolved in 10 ml of ether was added dropwise over a 10 minute period and a white precipitate began to form. The reaction was slowly allowed to warm to room temperature and stirred overnight. The reaction solution was diluted with 150 ml of ethyl acetate and 50 ml of water. The phases were separated and the organic phase dried with magnesium sulfate, filtered and concentrated to yield an oil. The oil was flash chromatographed on Merck silica gel (230-400 mesh) eluting with hexanes and ethyl acetate. Similar fractions were combined and concentrated to yield 1.95 g of the desired product as a clear oil.

Using the procedure described in this example, the following phosphosulfonates as described in Table I were prepared from O-ethyl P-[[(2-chloro-6-methylphenyl)sulphonyloxy]methyl]phosphonoyl chloride (Example 45), and the indicated alcohol, amine or mercaptan unless otherwise noted:

Compound 73: 2,2,2-trifluoroethanol;
Compound 74: O-ethyl P-[[(2-(trifluoromethyl)phenyl)sulphonyloxy]methyl]phosphonoyl chloride (Example 45) was reacted with 2,2,2-trifluoroethanol;
Compound 78: phenol;
Compound 79: isopropylamine, 2 equivalents, no triethylamine used;
Compound 88: di-n-propylamine, 2 equivalents, no triethylamine used;
Compound 93: isopropyl mercaptan;
Compound 94: 2-methoxyethanol;
Compound 95: n-propanol;
Compound 97: dimethylamine, 2 equivalents, no triethylamine used;
Compound 104: cyclopentanol;
Compound 105: isobutyl alcohol;
Compound 106: sec-butyl alcohol;
Compound 108: O-ethyl P-[[(2,6-dichlorophenyl)sulphonyloxy]methyl]phosphonoyl chloride (Example 45) was reacted with isopropanol;
Compound 117: methanol, pyridine used in place of triethylamine.

EXAMPLE 54

O-Isopropyl-O-methyl P-[[(2-chloro-6-methylphenyl)sulfonyloxy]methyl]phosphonate (Compound 116)

A solution of 50 ml of ether, 14.0 ml of triethylamine, and 3.2 g of methanol was added dropwise over 70 minutes to a solution at 10° C. of 32.0 g of O-isopropyl P-[[(2-chloro-6-methylphenyl)sulfonyloxy]methyl]phosphonoyl chloride, (Example 44), and 130 ml of ether. The reaction was then allowed to warm to room temperature. After stirring for an additional 90 minutes, the reaction was diluted with 260 ml of ethyl acetate, the ethyl acetate solution washed with 100 ml of water, then washed with 80 ml of water, dried with magnesium sulfate, filtered and concentrated to yield 24.5 g of the crude desired product as a yellow oil. The crude product was flash chromatographed using ethyl acetate and hexanes. Similar fractions were combined to yield 11.1 g of the desired product.

Using the procedure described above, the following phosphosulfonates as described in Table I were prepared by reacting the indicated phosphonoyl chlorides of Formula IX with the indicated alcohol unless noted otherwise:

Compound 127: 3-butyn-2-ol;
Compound 128: propargyl alcohol;
Compound 133: O-isopropyl P-[[(4-chloro-2,6-dimethylphenyl)sulfonyloxy]methyl]phosphonoyl chloride (Example 44) was reacted with methanol;
Compound 135: O-isopropyl P-[[(2,4-dichloro-6-methylphenyl)sulfonyloxy]methyl]phosphonoyl chloride (Example 44) was reacted with methanol;
Compound 138: O-isopropyl P-[[(2,4-chloro-6-methoxyphenyl)sulfonyloxy]methyl]phosphonoyl chloride (Example 44) was reacted with methanol;
Compound 147: O-isopropyl; P-[[(2,5-dichloro-3,6-dimethylphenyl)sulfonyloxymethyl]phosphonoyl chloride (Example 44) was reacted with methanol;
Compound 157: O-isopropyl P-[[(2-methoxy-6-(trifluoromethyl)phenyl)sulfonyloxy]methyl]phosphonoyl chloride (Example 44) was reacted with methanol; and
Compound 179: O-isopropyl P-[[(2-chloro-6-isopropylphenyl)sulfonyloxy]methyl]phosphonoyl chloride (Example 44) was reacted with ethanol (0.1 g DMAP added).
Compound 215: O-isopropyl P-[[(2-chloro-6-isopropylphenyl)sulfonyloxy]-methyl]phosphonoyl chloride (Example 60) was reacted with methanol, wherein methylene chloride was used in place of ether as the solvent and 0.1 g of DMAP was added to the phosphonoyl chloride solution;

Compound 216: O-isopropyl P-[[(2-chlorophenyl)sulfonyloxy]methyl]phosphonoyl chloride (Example 49) was reacted with ethanol, wherein methylene chloride was used in place of ether as the solvent and 0.1 g of DMAP was added to the phosphonoyl chloride solution;

Compound 247: O-ethyl P-[[(2,5-dichloro-4-methyl-3-thienyl)sulfonyloxy]-methyl]phosphonoyl chloride (Example 45) was reacted with isopropanol, wherein methylene chloride was used in place of ether as the solvent and 0.1 g of DMAP was added to the phosphonoyl chloride solution;

Compound 255: O-isopropyl P-[[(2-ethoxy-6-(trifluoromethyl)phenyl)sulfonyloxy]-methyl]phosphonoyl chloride (Example 49) was reacted with ethanol, wherein methylene chloride was used in place of ether as the solvent and 0.1 g of DMAP was added to the phosphonoyl chloride solution;

EXAMPLE 55

Dimethyl P-[[(2-Chloro-6-methylphenyl)sulfonyloxy]methyl]phosphonate (Compound 115)

A solution of 5.0 g of methanol, 9.3 ml of triethylamine and 40 ml of anhydrous ether was slowly added to a solution at 5° C. of 22.5 g of P-[[(2-chloro-6-methylphenyl)sulfonyloxy]methyl]phosphonoyl dichloride, (Example 50), and 90 ml of anhydrous ether. Shortly after the addition of the methanol solution was complete the reaction was allowed to warm to room temperature and stir overnight. The reaction solution was diluted with 200 ml of ethyl acetate and 80 ml of water, the phases separated and the organic phase dried with magnesium sulfate, filtered and concentrated to yield 17.6 g of the desired product, mp 55°–57.5° C.

EXAMPLE 56

O-Isopropyl-O-methyl P-[[(2-(trifluoromethyl)phenyl)sulfonyloxy]methyl]phosphonate (Compound 141)

A solution of 40 ml of THF, 9.1 ml of triethylamine and 1.86 g of methanol was added dropwise over 100 minutes to a solution at −20° C. of 20.9 g of O-isopropyl P-[[(2-(trifluoromethyl)phenyl)sulfonyloxy]methyl]phosphonoyl chloride, (Example 47), 0.1 g of DMAP and 50 ml of THF. The reaction temperature was maintained between −25° C. and −10° C. during the addition. The reaction was allowed to slowly warm to room temperature and stir overnight at room temperature. The reaction was then diluted with 200 ml of ethyl acetate, the ethyl acetate solution washed with two 100 ml portions of water, dried with magnesium sulfate, filtered, and concentrated to yield 17.7 g of the desired product as a yellow oil.

Compound 162 was prepared using the procedure described above and using O-ethyl P-[[(2-chloro-6-methylphenyl)sulfonyloxy]methyl]phosphonoyl chloride (Example 52) and cyclopentyl alcohol.

Using the procedure described above except using a reaction temperature of 10° C., the following phosphosulfonates as described in Table I were prepared by reacting the indicated phosphonoyl chloride of Formula IX with the indicated nucleophile unless noted otherwise:

Compound 161: O-ethyl P-[[(2-chloro-6-methylphenyl)sulfonyloxy]methyl]phosphonoyl chloride, (Example 45), and neopentyl alcohol, using ether as solvent;

Compound 163: O-ethyl P-[[(2-chloro-6-methylphenyl)sulfonyloxy]methyl]phosphonoyl chloride, (Example 45), and 2-hydroxypropionitrile, using ether as solvent;

Compound 164: O-ethyl P-[[(2-chloro-6-methylphenyl)sulfonyloxy]methyl]phosphonoyl chloride, (Example 45), and acetone oxime;

Compound 165: O-ethyl P-[[(2-chloro-6-methylphenyl)sulfonyloxy]methyl]phosphonoyl chloride, (Example 45), and cyclopropylmethyl alcohol; and Compound 166: O-ethyl P-[[(2-chloro-6-methylphenyl)sulfonyloxy]methyl]phosphonoyl chloride, (Example 45), and α-methylbenzyl alcohol, using ether as solvent.

EXAMPLE 57

O-Isopropyl-O-methyl P-[[(2-methyl-6-(trifluoromethyl)phenyl]sulfonyloxyl]-methyl] phosphonate (Compound 142)

A solution of 10 ml of ether, 0.7 ml of triethylamine, and 0.16 g of methanol was added dropwise over 5 minutes to a solution at 10° C. of 1.80 g of O-isopropyl P-[[(2-methyl-6-(trifluoromethyl)phenyl)sulfonyloxy]-methyl]phosphonoyl chloride, (Example 48A), and 15 ml of ether. After one hour the reaction was allowed to warm to room temperature and stir for an additional three hours. The reaction was diluted with 150 ml of ethyl acetate, the ethyl acetate solution washed with 40 ml of water, dried with sodium sulfate, filtered and concentrated to yield 1.6 g of the crude desired product as a yellow oil. The crude product was diluted with 2 ml of methylene chloride and flash chromatographed using ethyl acetate and hexanes. Similar fractions were combined to yield 0.7 g of the desired product as an amber oil.

EXAMPLE 58: O-Isopropyl-O-methyl P-[[(2,6-dichlorophenyl)sulfonyloxy]methyl]phosphonate (Compound 111)

A solution of 20 ml of ether, 7.0 ml of triethylamine and 1.50 g of methanol was added dropwise over 25 minutes to a solution at 10° C. of 17.0 g of O-isopropyl P-[[(2,6-dichlorophenyl)sulfonyloxy]methyl]phosphonoyl chloride, (Example 49), and 80 ml of ether. The reaction mixture then was allowed to warm to room temperature. After an additional 2 hours of stirring, the reaction was diluted with 220 ml of ethyl acetate, the ethyl acetate solution washed with two 60 ml portions of water, dried with magnesium sulfate, filtered and concentrated to yield 19.8 g of the crude desired product as a yellow oil. The crude product was purified by flash chromatography eluting with ethyl acetate and hexanes. Similar fractions were combined and impure fractions that contained the desired product were rechromatographed using similar conditions. A total of 9.8 g of the desired product was isolated.

EXAMPLE 59

O-(2-Butyl) P-ethyl[[(2-chloro-6-methylphenyl)sulfonyloxy]methyl]phosphinate (Compound 214)

To a solution of 5.83 g of P-ethyl[[(2-chloro-6-methylphenyl)sulfonyloxy]-methyl]phosphinoyl chloride (Example 51) and 0.2 g of 4-dimethylaminopyridine (DMAP) in 15 ml of methylene chloride at 10° C. was added dropwise over 10 minutes a solution of 1.52 g of sec-butanol and 2.32 g of triethylamine in 8 ml of methylene chloride. After 1 hour, the cooling bath was removed and the reaction was warmed to room temperature and stirred an additional two hours. The reaction mixture was diluted with ethyl acetate, 20 ml, ether, 50 ml, and water, 60 ml, and the organic phase was separated, washed with an additional 50 ml of water, dried with magnesium sulfate, filtered and concentrated. The resulting oil was dissolved in 4 ml of methylene chloride and flash chromatographed on Merck silica gel using blends of ethyl acetate and hexanes. Similar fractions were combined to yield 3.2 g of desired product as a tan oil.

Using the procedure described in this example, the following phosphosulfonates as described in Table I were prepared from P-ethyl[[(2-chloro-6-methylphenyl)sulfonyloxy]-methyl]phosphinoyl chloride (Example 51) and the indicated alcohol:
Compound 212: n-propanol
Compound 213: cyclobutanol.
Compound 225: t-butanol
Compound 229: 2-methyl-1-propanol
Compound 230: n-butanol
Compound 232: methanol Also, using the procedure above, the following phosphosulfonates as described in Table 1 were prepared from P-methyl[[(2-chloro-6-isopropylphenyl)sulfonyloxy]methyl]phosphinoyl chloride (Example 51) and the indicated alcohol:
Compound 228: ethanol
Compound 240: n-propanol
Compound 241: 2-methyl-1-propanol

ADDITIONAL EXAMPLES

EXAMPLE 60

O-Isopropyl P[[(2-chloro-6-isopropylphenyl)sulfonyloxy])methyl]-phosphonoyl chloride The phosphorus pentachloride (2.5 g) was added to 120 ml of methylene chloride and stirred for 60 minutes. Not all of the phosphorus pentachloride dissolved. A solution of 4.3 g of O-diisopropyl P-[[(2-chloro-6-isopropylphenyl)sulfonyloxy]methyl]phosphonate (Compound 184) in 10 ml of methylene chloride was added at once. The reaction was allowed to stir overnight. A two ml reaction aliquot was concentrated under reduced pressure and phosphorus NMR indicated the reaction was complete. The reaction was concentrated under reduced pressure and 100 ml of toluene was added to help azeotrope the residual phosphorus oxychloride during a second concentration under reduced pressure to yield an amber oil.

EXAMPLE 61

2,5-Dichloro-3-methyl-4-thiophenesulfonyl chloride

A: 2,5-Dichloro-3-methylthiophene

To a solution of 25.0 g of 3-methylthiophene in 60 ml of 1,2-dichloroethane at 10 C. was added dropwise over 50 minutes a solution of 43 ml of sulfurylchloride in 10 ml of 1,2-dichloroethane. The temperature did not exceed 30 C. during the addition. Thirty minutes after the addition was complete, the cooling bath was removed and the reaction was allowed to stir overnight. The reaction was concentrated under reduced pressure to yield 30.7 g of the desired product.

B: 2,5-Dichloro-3-methyl-4-thiophenesulfonyl chloride

The title compound was prepared as described in Example 5B.

EXAMPLE 62

5-Chloro-3-isopropyl-1-methyl-4-pyrazolesulfonyl chloride

A: 5-Hydroxy-3-isopropyl-1-methylpyrazole

To a solution of 30.0 grams of ethyl isobutyrylacetate in 130 ml of ethanol (anhydrous,5% methanol) at 10 C. was added dropwise over 30 minutes a solution of 8.7 grams of methyl hydrazine in 30 mls of ethanol. The reaction temperature did not exceed 20 C. After twenty minutes of additional stirring the cooling bath was removed and 2 ml of glacial acetic acid was added. After one hour of stirring at room temperature the reaction was then refluxed for four hours. After stirring overnight at room temperature the reaction was concentrated to yield a yellowish solid. This solid was stirred with 100 ml of hexanes for 30 minutes and the off-white solid was collected and rinsed with 75 ml of hexanes. The solid was dried in a vacuum oven at 45 C. overnight to yield 23.3 g of the desired product, mp 120–122 C.

B: 5-Chloro-3-isopropyl-1-methylpyrazole

The 5-hydroxy-3-isopropyl-1-methylpyrazole (20.5 g) was added in small portions over five minutes to 60 ml of phosphorus oxychloride cooled at 10 C. No significant exotherm resulted and after five minutes the cooling bath was removed. After stirring for one hour, the reaction was heated to 70 C. overnight and then 90 C. for four hours. The cooled reaction was cautiously added to 500 g of ice. The desired product was extracted with two 200 ml portions of ethyl acetate and the combined extracts were concentrated under reduced pressure to yield 13.7 g of the desired product as an oil.

C: 5-Chloro-3-isopropyl-1-methyl-4-pyrazolesulfonyl chloride

The title compound was prepared as described in example 63B without the use of thionyl chloride.

Following the above procedures 62A–C, the 5-chloro-3-ethyl-1-methyl-4-pyrazolesulfonyl chloride was prepared using ethyl propionylacetate instead of ethyl isobutyrylacetate.

EXAMPLE 63

1,5-Dimethyl-3-(trifluoromethyl)-4-pyrazolesulfonyl chloride

A: 1,5-Dimethyl-3-(trifluoromethyl)pyrazole

To a solution 25.0 grams of 1,1,1,-trifluoro-2,4-pentanedione in 150 ml of ethanol (anhydrous, 5% methanol) at 10 C. was added dropwise over 35 minutes a solution 8.3 grams of methyl hydrazine in 25 ml of ethanol. The reaction temperature did not exceed 20 C. After an additional 30 minutes of stirring, the cooling bath was removed and the reaction was allowed to stir for one hour. Then five ml of glacial acetic acid was added and the reaction was refluxed for four hours. The reaction was then concentrated under reduced pressure and 100 ml of toluene was added to help azeotrope the residual acetic acid during a second concentration under reduced pressure. High vacuum was pulled on the sample for one hour at 50 C. to yield 25.3 g of the desired product as an oil.

B: 1,5-Dimethyl-3-(trifluoromethyl)--4-pyrazolesulfonyl chloride

To 53 mls of chlorosulfonic acid at 10 C. was added dropwise over fifteen minutes 1,5-dimethyl-3-(trifluoromethyl)pyrazole (24.0 grams). No significant exotherm resulted and after 15 minutes the cooling bath was removed and the reaction was heated to 110 C. for three hours. After standing overnight, the reaction was heated to 110 C. for an additional four hours and allowed to cool to 50 C. Then 19.0 g of thionyl chloride was dropwise over fifteen minutes. The reaction was then heated to 80 C. for twenty minutes and 110 C. for one hour. After cooling, the reaction was cautiously added to 600 g of ice. The aqueous phase was extracted with two 250 ml portions of ether. The combined organic extracts were dried with MgSO$_4$ and concentrated under reduced pressure to yield 7.8 g of the desired product as a tan oil.

Using the procedure described in Example 63B, except the use of thionyl chloride was omitted, the following sulfonyl chloride was prepared from the indicated pyrazole:

1,3,5-trimethyl-4-pyrazolesulfonyl chloride from the 1,3,5-trimethylpyrazole.

EXAMPLE 64

8-Chloro-1-naphthalenesulfonyl chloride

To 28.0 g of phenylphosphonic dichloride was added the solid 8-chloronapthalene-1-sulfonic acid (10.0 g) in small portions over three minutes. No significant exotherm occurred and the reaction was heated to 110 C. for eighteen hours. After cooling, the reaction was cautiously added to 300 g of ice and then extracted with two 200 ml portions of ether. The combined organic extracts were dried with MgSO$_4$ and concentrated under reduced pressure to yield 22 g of a white solid which was triturated with a mixture of 70 ml of methylene chloride and 50 ml of toluene. Not all of the solid dissolved and 80 ml of water was added which dissolved the remaining solid. The organic phase was washed with an additional 80 ml of water, dried with MgSO$_4$ and concentrated under reduced pressure to yield 7.4 g of a white solid which contained a 1:1 mixture of the desired product and the phenyl phosphonic acid. The material was used without further purification.

EXAMPLE 65

2-Ethoxy-6-(trifluoromethyl)benzenesulfonyl chloride and 2-ethoxy-4-(trifluoromethyl)benzenesulfonyl chloride To a solution of 100 ml of ether and 90 ml of 1.6M solution of n-butyllithium in hexane was added a solution of 3-ethoxybenzo-trifluoride (23.6 g) in 30 ml of ether at −20 C. After ½ of the 3-ethoxybenzotrifluoride/ether solution was added over twenty minutes the reaction was allowed to warm to room temperature and the remainder of the solution was added over fifteen minutes. A warm water bath(30 C.) was used to heat the reaction and the reaction temperature rose to 35 C. and held at that temperature for two hours. The warming bath was removed and the reaction was allowed to stir overnight at room temperature.

Sulfur dioxide was condensed into 70 ml of ether for 90 minutes and the resulting solution was cooled to −30 C. The solution of litho-3-ethoxybenzotrifluoride was added in small portions over 60 minutes at −30 C. to −40 C. and a precipitate readily formed. The reaction was allowed to warm to room temperature and stir for one hour. To the cooled reaction(8 C.) was added dropwise over ten minutes a solution of 14.9 g of sulfuryl chloride in 10 ml of hexanes. The reaction warmed to 12 C. and after 40 minutes of stirring the cooling bath was removed and the reaction was stirred overnight. Ten ml of water was added which caused a mild exotherm (decomposition of the excess sulfuryl chloride) and after twenty minutes an additional 40 ml of water was added. The organic phase was separated, dried with MgSO$_4$, and concentrated under reduced pressure to yield 28.6 g of a brown oil. Fluorine NMR and GC indicated a mixture of the desired products as well as a small amount of the starting material. The material was used without further purification.

Herbicidal Activity Tests:

The following test procedure was employed to assess the herbicidal activity of the compounds of the invention.

Seeds of selected plants were planted in flats or pots. For pre-emergence tests, immediately after planting, the test compound was sprayed directly onto the soil surface. The flats or pots were then placed in a greenhouse and watered. For postemergence tests, the seeds were allowed to germinate and grow in a greenhouse for 10 to 21 days. Before application, each series of test plants were selected for uniformity, size and stage of development. The test plants were then treated with the test compound. The plants for postemergence tests were returned to the greenhouse and then watered. Test species employed were:

| | MONOCOTS | |
|---|---|---|
| CODE | COMMON NAME | SCIENTIFIC NAME |
| BYG | Barnyardgrass | *Echinochloa crus-galli* |
| CRB | Crabgrass | *Digitaria sanguinalis* |
| FOX | Green Foxtail | *Setaria viridis* |
| JON | Johnsongrass | *Sorghum halepense* |
| MF | Meadow Foxtail | *Alopecurus pratensis* |
| NUT | Nutsedge | *Cyperus esculentus* |
| WO | Wild Oat | *Avena fatua* |

| | DICOTS | |
|---|---|---|
| CODE | COMMON NAME | SCIENTIFIC NAME |
| BID | Beggartick | *Bidens pilosa* |
| CKL | Cocklebur | *Xanthium strumarium* |
| MG | Morningglory | *Ipomoea lacunosa* |
| NS | Nightshade | *Solanum nigrum* |
| PIG | Pigweed | *Amaranthus retroflexus* |
| SMT | Smartweed | *Polygonum lapathifolium* |
| VEL | Velvetleaf | *Abutilon theophrasti* |

The compound to be evaluated was dissolved in an appropriate solvent, usually acetone, and sprayed over the flats or pots using a carrier volume equivalent to 25 or 50 gallons per acre at the rate of application in pounds per acre (lb/A) specified in the table. About two or three weeks after application of the test compound, the state of growth of the plants was observed. Each species was evaluated on a scale of 0–100 in which 0 equals no activity and 100 equals total control.

The results are shown in Tables 2A, 2B and 2C.

TABLE 2A

| Cpd No. | Appl Type | Rate lb/acre | CKL | MG | PIG | SMT | VEL | BYG | FOX | JON | NUT | WO |
|---|---|---|---|---|---|---|---|---|---|---|---|---|
| 1. | Pre | 4.00 | 0 | 16 | 100 | 100 | 90 | 100 | 100 | 90 | 91 | 81 |
|  | Post | 4.00 | 10 | 20 | 70 | 10 | 15 | 10 | 10 | 15 | 0 | 10 |
| 2. | Pre | 4.00 | 0 | 0 | 81 | 0 | 0 | 100 | 90 | 76 | —* | 0 |
|  | Post | 4.00 | 0 | 0 | 0 | 0 | 0 | 0 | 0 | 0 | 0 | 0 |
| 3. | Pre | 4.00 | 0 | 0 | 71 | 0 | 41 | 100 | 100 | 81 | 0 | 0 |
|  | Post | 4.00 | 0 | 0 | 0 | 0 | 0 | 0 | 0 | 0 | 0 | 0 |
| 4. | Pre | 4.00 | 0 | 0 | 100 | 21 | 0 | 100 | 98 | 86 | 0 | 0 |
|  | Post | 4.00 | 0 | 15 | 10 | 5 | 0 | 0 | 10 | 0 | 0 | 0 |
| 5. | Pre | 4.00 | — | 0 | 65 | 15 | 0 | 100 | 100 | 56 | 0 | 0 |
|  | Post | 4.00 | 0 | 10 | 15 | 5 | 5 | 0 | 10 | 0 | 0 | 0 |
| 6. | Pre | 4.00 | 0 | 10 | 100 | 0 | 0 | 100 | 95 | 100 | 41 | 81 |
|  | Post | 4.00 | 0 | 10 | 0 | 0 | 0 | 0 | 0 | 0 | 0 | 0 |
| 7. | Pre | 4.00 | 0 | 0 | 0 | 0 | 0 | 95 | 85 | 95 | 0 | 0 |
|  | Post | 4.00 | 0 | 0 | 0 | 0 | 0 | 0 | 0 | 0 | 0 | 0 |
| 8. | Pre | 4.00 | 0 | 0 | 100 | 0 | 0 | 100 | 98 | 100 | 21 | 51 |
|  | Post | 4.00 | 0 | 10 | 0 | 0 | 0 | 0 | 0 | 10 | 0 | 0 |
| 9. | Pre | 4.00 | 0 | 31 | 100 | 0 | 26 | 100 | 100 | 98 | 61 | 90 |
|  | Post | 4.00 | 0 | 20 | 0 | 0 | 10 | 51 | 61 | 15 | 0 | 0 |
| 10. | Pre | 4.00 | 0 | 0 | 100 | 0 | 100 | 100 | 100 | 0 | 51 |  |
|  | Post | 4.00 | 0 | 15 | 0 | 0 | 0 | 0 | 0 | 0 | 0 | 0 |
| 11. | Pre | 4.00 | 0 | 0 | 0 | 71 | 0 | 100 | 86 | 31 | 0 | 0 |
|  | Post | 4.00 | 0 | 0 | 0 | 0 | 0 | 0 | 0 | 0 | 0 | 0 |
| 12. | Pre | 4.00 | 0 | 0 | 0 | 0 | 0 | 100 | 90 | 41 | 0 | 0 |
|  | Post | 4.00 | 0 | 0 | 0 | 0 | 0 | 0 | 0 | 0 | 0 | 0 |
| 13. | Pre | 4.00 | 100 | 0 | 100 | — | 0 | 100 | 100 | 100 | 0 | 81 |
|  | Post | 4.00 | 0 | 10 | 0 | 0 | 0 | 0 | 20 | 35 | 0 | 10 |
| 14. | Pre | 4.00 | 100 | 17 | 100 | 0 | 99 | 100 | 100 | 99 | 0 | 0 |
|  | Post | 4.00 | 0 | 0 | 0 | — | 0 | 0 | 0 | 0 | 0 | 0 |
| 15. | Pre | 4.00 | 0 | 0 | 0 | 0 | 0 | 6 | 16 | 0 | 0 | 0 |
|  | Post | 4.00 | 0 | 0 | 0 | 0 | 0 | 0 | 0 | 0 | 0 | 0 |
| 16. | Pre | 4.00 | — | 0 | 0 | 0 | 0 | 65 | 76 | 35 | 0 | 0 |
|  | Post | 4.00 | 0 | 0 | 0 | — | 0 | 0 | 0 | 0 | 0 | 0 |
| 17. | Pre | 4.00 | — | 0 | 0 | 0 | 0 | 15 | 30 | 0 | — | 0 |
|  | Post | 4.00 | 0 | 15 | 0 | — | 0 | 0 | 0 | 0 | 0 | 0 |
| 18. | Pre | 4.00 | 0 | 0 | 100 | 0 | 0 | 98 | 100 | 100 | 0 | 81 |
|  | Post | 4.00 | 0 | 0 | 0 | 0 | 0 | 46 | 36 | 0 | 0 | 0 |
| 19. | Pre | 4.00 | 0 | 0 | 100 | 0 | 0 | 100 | 100 | 100 | 0 | 71 |
|  | Post | 4.00 | 0 | 0 | 0 | 0 | 0 | 86 | 16 | 0 | 0 | 0 |
| 20. | Pre | 4.00 | 36 | 10 | 100 | 0 | 0 | 100 | 98 | 100 | 81 | 81 |
|  | Post | 4.00 | 0 | 20 | 0 | 15 | 0 | 70 | 100 | 25 | 76 | 46 |
| 21. | Pre | 4.00 | — | 0 | 0 | 0 | 0 | 100 | 95 | 90 | 0 | 0 |
|  | Post | 4.00 | 0 | 10 | 0 | 0 | 0 | 75 | 100 | 0 | 0 | 100 |
| 22. | Pre | 4.00 | 0 | 0 | 0 | 0 | 0 | 100 | 90 | 86 | 0 | 0 |
|  | Post | 4.00 | 0 | 0 | 0 | 0 | 0 | 10 | 100 | 0 | 0 | 90 |
| 23. | Pre | 4.00 | 0 | 0 | 0 | 0 | 0 | 86 | 0 | 0 | 0 | 0 |
|  | Post | 4.00 | 0 | 0 | 0 | 0 | 0 | 0 | 0 | 0 | 0 | 0 |
| 24. | Pre | 4.00 | 0 | 0 | 100 | 0 | 100 | 100 | 100 | 98 | 0 | 31 |
|  | Post | 4.00 | 0 | 0 | 0 | 0 | 0 | 15 | 20 | 0 | 0 | 0 |
| 25. | Pre | 4.00 | 0 | 0 | 90 | 0 | 0 | 98 | 98 | 100 | 0 | 76 |
|  | Post | 4.00 | 0 | 10 | 0 | 15 | 46 | 10 | 20 | 25 | 0 | 0 |
| 26. | Pre | 4.00 | 0 | 0 | 0 | 0 | 0 | 76 | 0 | 0 | — | 0 |
|  | Post | 4.00 | 0 | 0 | 0 | 0 | 0 | 0 | 0 | 0 | 0 | 0 |
| 27. | Pre | 4.00 | 0 | 0 | 0 | 0 | 0 | 66 | 0 | 11 | 0 | 0 |
|  | Post | 4.00 | 0 | 0 | 0 | 0 | 0 | 16 | 26 | 0 | 0 | 0 |
| 28. | Pre | 4.00 | — | 100 | 0 | 0 | 0 | 86 | 86 | 15 | 61 | 11 |
|  | Post | 4.00 | 0 | 0 | 0 | 0 | 0 | 60 | 60 | 0 | 0 | 0 |
| 29. | Pre | 4.00 | 0 | 15 | 100 | 0 | 0 | 96 | 96 | 96 | 100 | 81 |
|  | Post | 4.00 | 0 | 5 | 0 | 0 | 0 | 41 | 31 | 0 | — | 0 |
| 30. | Pre | 4.00 | — | 80 | 100 | 5 | 80 | 100 | 100 | 100 | 100 | 90 |
|  | Post | 4.00 | 0 | 10 | 0 | 0 | 0 | 6 | 86 | 15 | 0 | 21 |
| 31. | Pre | 4.00 | — | 0 | 0 | 0 | 0 | 100 | 98 | 98 | 100 | 70 |
|  | Post | 4.00 | 0 | 0 | 0 | 0 | 0 | 10 | 25 | 20 | 0 | 0 |
| 32. | Pre | 4.00 | 0 | 0 | 0 | 0 | 0 | 86 | 96 | 86 | 0 | 31 |
|  | Post | 4.00 | 0 | 0 | 0 | 0 | 0 | 0 | 0 | 0 | 0 | 0 |
| 33. | Pre | 4.00 | — | 0 | 0 | 0 | 0 | 86 | 99 | 36 | 0 | 3 |
|  | Post | 4.00 | 0 | 10 | 0 | 0 | 0 | 0 | 0 | 0 | 0 | 0 |
| 34. | Pre | 4.00 | — | 0 | 100 | 0 | 0 | 96 | 100 | 96 | 100 | 5 |
|  | Post | 4.00 | 0 | 0 | 0 | 0 | 0 | 41 | 0 | 51 | 0 | 0 |
| 35. | Pre | 4.00 | 0 | 0 | 0 | 0 | 0 | 86 | 86 | 76 | — | 0 |
|  | Post | 4.00 | 0 | 0 | 0 | 0 | 0 | 0 | 0 | 0 | 0 | 0 |
| 36. | Pre | 4.00 | 0 | 0 | 0 | 0 | 0 | 76 | 86 | 66 | — | 0 |
|  | Post | 4.00 | 0 | 5 | 0 | 0 | 0 | 0 | 0 | 0 | 0 | 0 |
| 37. | Pre | 4.00 | 0 | 0 | 0 | 0 | 0 | 100 | 100 | 86 | 0 | 31 |
|  | Post | 4.00 | 0 | 5 | 0 | 0 | 10 | 15 | 35 | 10 | 15 | 0 |
| 38. | Pre | 4.00 | 0 | 0 | 0 | 0 | 0 | 96 | 100 | 96 | 0 | 11 |
|  | Post | 4.00 | 0 | 10 | 5 | 0 | 0 | 20 | 15 | 25 | 0 | 0 |
| 39. | Pre | 4.00 | 0 | 0 | 0 | — | 0 | 56 | 76 | 76 | 71 | 0 |
|  | Post | 4.00 | 0 | 0 | 0 | 0 | 16 | 0 | 0 | 0 | 0 | 0 |
| 40. | Pre | 4.00 | 0 | 0 | 0 | — | 0 | 86 | 100 | 96 | 0 | 0 |
|  | Post | 4.00 | 0 | 0 | 0 | — | 0 | 0 | 0 | 0 | 0 | 0 |

TABLE 2A-continued

| Cpd No. | Appl Type | Rate lb/acre | CKL | MG | PIG | SMT | VEL | BYG | FOX | JON | NUT | WO |
|---|---|---|---|---|---|---|---|---|---|---|---|---|
| 41. | Pre | 4.00 | 0 | 0 | 100 | — | 0 | 96 | 100 | 100 | 100 | 41 |
|  | Post | 4.00 | 0 | 10 | 0 | 0 | 0 | 15 | 0 | 0 | 0 | 0 |
| 42. | Pre | 4.00 | 0 | 0 | 100 | — | 0 | 96 | 100 | 100 | 100 | 0 |
|  | Post | 4.00 | 0 | 0 | 0 | — | 0 | 0 | 0 | 0 | 0 | 0 |
| 43. | Pre | 4.00 | 0 | 0 | 0 | — | 0 | 96 | 60 | 86 | 0 | 0 |
|  | Post | 40 | 0 | 0 | 0 | — | 0 | 0 | 0 | 0 | 0 | 0 |
| 44. | Pre | 40 | 0 | 20 | 100 |  | 99 | 86 | 100 | 100 | 100 | 81 |
|  | Post | 4.00 | 0 | 25 | 0 | 0 | 15 | 51 | 36 | 66 | 36 | 51 |
| 45. | Pre | 4.00 | 0 | 90 | 100 | — | 45 | 99 | 100 | 100 | 100 | 91 |
|  | Post | 4.00 | 0 | 0 | 0 | — | 0 | 36 | 26 | 6 | 46 | 51 |
| 46. | Pre | 4.00 | 0 | 10 | 100 | 0 | 0 | 100 | 100 | 90 | 91 | 81 |
|  | Post | 4.00 | 0 | 30 | 0 | 0 | 0 | 25 | 15 | 35 | 0 | 0 |
| 47. | Pre | 4.00 | 0 | 0 | 0 | 0 | 0 | 86 | 100 | 0 | 0 | 0 |
|  | Post | 4.00 | 0 | 10 | 0 | 0 | 0 | 0 | 0 | 0 | 0 | 0 |
| 48. | Pre | 4.00 | 0 | — | 0 | 0 | 0 | 96 | 100 | 75 | 0 | 61 |
|  | Post | 4.00 | 0 | 15 | 0 | 0 | 0 | 20 | 0 | 0 | 0 | 0 |
| 49. | Pre | 4.00 | 0 | 0 | 100 | 0 | 0 | 100 | 100 | 36 | 0 | 21 |
|  | Post | 4.00 | 0 | 0 | 0 | 0 | 0 | 0 | 0 | 20 | 0 | 0 |
| 50. | Pre | 4.00 | 11 | 0 | 100 | 0 | 0 | 0 | 0 | 21 | 0 | 0 |
|  | Post | 4.00 | 0 | 100 | 0 | 0 | 20 | 0 | 0 | 0 | 0 | 0 |
| 51. | Pre | 4.00 | 0 | 100 | 100 | 0 | 0 | 81 | 81 | 41 | 41 | 0 |
|  | Post | 4.00 | 0 | 0 | 0 | 0 | 0 | 0 | 0 | 0 | 0 | 0 |
| 52. | Pre | 4.00 | 0 | 0 | 0 | 0 | 0 | 100 | 100 | 90 | 100 | 71 |
|  | Post | 4.00 | 0 | 16 | 0 | 0 | 0 | 25 | 10 | 41 | 10 | 51 |
| 53. | Pre | 4.00 | 0 | 10 | — | — | 31 | 100 | 100 | 86 | 100 | 71 |
|  | Post | 4.00 | 0 | 15 | 0 | 0 | 0 | 5 | 5 | 0 | 0 | 0 |
| 54. | Pre | 4.00 | 0 | 41 | 0 | — | 0 | 95 | 99 | 86 | 100 | 31 |
|  | Post | 4.00 | 0 | 10 | 0 | 0 | 0 | 21 | 10 | 0 | 0 | 0 |
| 55. | Pre | 4.00 | 0 | 61 | — | — | 100 | 100 | 100 | 86 | 100 | 91 |
|  | Post | 4.00 | 0 | 70 | 0 | 0 | 5 | 21 | 15 | 31 | 0 | 31 |
| 56. | Pre | 4.00 | 0 | 0 | 0 | — | 0 | 86 | 0 | 56 | 0 | 0 |
|  | Post | 4.00 | 0 | 10 | — | 0 | 0 | 0 | 0 | 0 | 0 | 0 |
| 57. | Pre | 4.00 | 0 | 0 | 100 | — | 0 | 96 | 100 | 100 | 100 | 86 |
|  | Post | 4.00 | 0 | 25 | — | 0 | 0 | 25 | 15 | 35 | 0 | 0 |
| 58. | Pre | 4.00 | — | 0 | 100 | — | 0 | 98 | 100 | 61 | 51 | 31 |
|  | Post | 4.00 | 0 | 0 | 0 | 0 | 0 | 0 | 0 | 0 | 0 | 0 |
| 59. | Pre | 4.00 | — | 0 | 71 | — | 0 | 100 | 100 | 90 | 100 | 61 |
|  | Post | 4.00 | 0 | 15 | 0 | 0 | 0 | 0 | 0 | 0 | 0 | 0 |
| 60. | Pre | 4.00 | 0 | 0 | 71 | — | 0 | 99 | 100 | 61 | 61 | 51 |
|  | Post | 4.00 | 0 | 25 | 0 | 0 | 10 | 0 | 0 | 0 | 0 | 0 |
| 61. | Pre | 4.00 | — | 0 | 100 | — | 20 | 98 | 100 | 96 | 100 | 71 |
|  | Post | 4.00 | 0 | 0 | 0 | 0 | 15 | 0 | 0 | 0 | 0 | 0 |
| 62. | Pre | 4.00 | 0 | 0 | 100 | — | 0 | 100 | 100 | 6 | 0 | 8 |
|  | Post | 4.00 | 0 | 15 | 0 | 0 | 0 | 0 | 0 | 0 | 0 | 0 |
| 63. | Pre | 4.00 | 0 | 0 | 0 | 0 | 0 | 36 | 96 | 66 | 0 | 0 |
|  | Post | 4.00 | 0 | 20 | 10 | 0 | 0 | 5 | 0 | 0 | 0 | 0 |
| 64. | Pre | 4.00 | 0 | 0 | 0 | 0 | 0 | 90 | 100 | 80 | 0 | 21 |
|  | Post | 4.00 | 0 | 0 | 0 | 0 | 0 | 0 | 0 | 0 | 0 | 0 |
| 65. | Pre | 4.00 | 0 | 20 | 100 | 90 | 100 | 100 | 100 | 100 | 100 | 81 |
|  | Post | 4.00 | 10 | 35 | 10 | 10 | 15 | 15 | 26 | 10 | 0 | 20 |
| 66. | Pre | 4.00 | — | 21 | 100 | 0 | 25 | 100 | 100 | 100 | 100 | 21 |
|  | Post | 4.00 | 0 | 0 | 0 | 0 | 0 | 0 | 0 | 0 | 0 | 0 |
| 67. | Pre | 2.00 | 0 | 0 | 90 | 0 | 0 | 75 | 65 | 10 | 0 | 0 |
|  | Post | 2.00 | 0 | 20 | 0 | 0 | 0 | 0 | 0 | 0 | 0 | 0 |
| 68. | Pre | 4.00 | 0 | 0 | 100 | 0 | 0 | 100 | 100 | 56 | 10 | 0 |
|  | Post | 4.00 | 0 | 10 | 0 | 0 | 5 | 0 | 0 | 10 | 0 | 0 |
| 69. | Pre | 4.00 | 0 | 0 | 90 | 0 | 0 | 76 | 100 | 56 | 10 | 11 |
|  | Post | 4.00 | 0 | 10 | 0 | 0 | 5 | 0 | 0 | 15 | 0 | 0 |
| 70. | Pre | 4.00 | 0 | 0 | 100 | 100 | 0 | 99 | 100 | 66 | 90 | 61 |
|  | Post | 4.00 | 0 | 10 | 0 | 0 | 5 | 0 | 0 | 5 | 0 | 0 |
| 71. | Pre | 4.00 | 0 | 0 | 100 | 50 | 0 | 100 | 100 | 66 | 15 | 10 |
|  | Post | 4.00 | 0 | 10 | 0 | 0 | 0 | 0 | 0 | 5 | 0 | 0 |
| 72. | Pre | 4.00 | 0 | 0 | 100 | 100 | 60 | 100 | 100 | 66 | 98 | 100 |
|  | Post | 4.00 | 15 | 20 | 10 | 0 | 10 | 10 | 26 | 15 | 0 | 66 |
| 73. | Pre | 4.00 | 0 | 0 | 0 | 0 | 0 | 98 | 100 | 95 | 0 | 51 |
|  | Post | 4.00 | 0 | 0 | 0 | 0 | 0 | 0 | 0 | 0 | 0 | 0 |
| 74. | Pre | 4.00 | 0 | 0 | 51 | 100 | 0 | 100 | 46 | 76 | 46 | 16 |
|  | Post | 4.00 | 0 | 0 | 0 | 0 | 0 | 6 | 6 | 0 | 0 | 0 |
| 75. | Pre | 4.00 | 0 | 35 | 100 | 51 | 26 | 100 | 100 | 96 | 66 | 86 |
|  | Post | 4.00 | 0 | 0 | 0 | 0 | 0 | 0 | 0 | 0 | 0 | 0 |
| 76. | Pre | 4.00 | 51 | 0 | 51 | 0 | 0 | 100 | 100 | 96 | 26 | 61 |
|  | Post | 4.00 | 0 | 0 | 0 | 0 | 0 | 0 | 0 | 0 | 0 | 0 |
| 77. | Pre | 4.00 | 0 | 0 | 100 | 61 | 16 | 100 | 100 | 86 | 81 | 11 |
|  | Post | 4.00 | 0 | 0 | 0 | 0 | 0 | 0 | 0 | 0 | 0 | 0 |
| 78. | Pre | 4.00 | 0 | 0 | 0 | 0 | 0 | 76 | 96 | 31 | 0 | 0 |
|  | Post | 4.00 | 0 | 0 | 0 | 0 | 0 | 0 | 0 | 0 | 0 | 0 |
| 79. | Pre | 4.00 | 0 | 0 | 0 | 0 | 0 | 86 | 86 | 86 | 0 | 71 |
|  | Post | 4.00 | 0 | 25 | 0 | 0 | 0 | 0 | 0 | 0 | 0 | 0 |
| 80. | Pre | 4.00 | 100 | 0 | 100 | 0 | 100 | 100 | 100 | 99 | — | 21 |
|  | Post | 4.00 | 0 | 0 | 0 | 0 | 0 | 0 | 10 | 0 | 0 | 0 |

TABLE 2A-continued

| Cpd No. | Appl Type | Rate lb/acre | CKL | MG | PIG | SMT | VEL | BYG | FOX | JON | NUT | WO |
|---|---|---|---|---|---|---|---|---|---|---|---|---|
| 81. | Pre | 4.00 | 100 | 0 | 100 | 21 | 16 | 100 | 100 | 100 | 26 | 31 |
| | Post | 4.00 | 0 | 0 | 0 | 0 | 0 | 0 | 15 | 0 | 0 | 0 |
| 82. | Pre | 4.00 | 51 | 21 | 0 | 0 | 0 | 86 | 86 | 96 | 0 | 11 |
| | Post | 4.00 | 0 | 15 | 10 | 10 | 15 | 0 | 0 | 0 | 0 | 0 |
| 83. | Pre | 4.00 | 0 | 0 | 0 | 0 | 0 | 95 | 100 | 100 | 0 | 30 |
| | Post | 4.00 | 0 | 0 | 0 | 0 | 0 | 0 | 0 | 0 | 0 | 0 |
| 84. | Pre | 4.00 | 0 | 0 | 0 | — | 0 | 70 | 80 | 90 | 0 | 0 |
| | Post | 4.00 | 0 | 0 | 0 | 0 | 0 | 0 | 0 | 0 | 0 | 0 |
| 85. | Pre | 4.00 | 0 | 0 | 0 | 0 | 0 | 100 | 100 | 100 | 0 | 15 |
| | Post | 4.00 | 0 | 0 | 0 | 0 | 0 | 0 | 0 | 0 | 0 | 0 |
| 86. | Pre | 4.00 | 0 | 0 | 0 | 0 | 0 | 70 | 85 | 90 | 0 | 0 |
| | Post | 4.00 | 0 | 0 | 0 | 0 | 0 | 0 | 0 | 0 | 0 | 0 |
| 87. | Pre | 4.00 | 0 | 0 | 50 | 0 | 0 | 100 | 100 | 90 | 26 | 51 |
| | Post | 4.00 | 0 | 5 | 0 | 0 | 0 | 0 | 0 | 0 | 0 | 0 |
| 88. | Pre | 4.00 | 0 | 0 | 0 | 0 | 0 | 0 | — | 0 | 0 | 0 |
| | Post | 4.00 | 0 | 60 | 0 | 0 | 10 | 0 | 0 | 0 | 0 | 0 |
| 89. | Pre | 4.00 | 0 | 0 | 0 | 80 | 0 | 100 | 95 | 100 | — | 0 |
| | Post | 4.00 | 0 | 10 | 0 | 0 | 0 | 26 | 66 | 6 | 0 | 0 |
| 90. | Pre | 4.00 | 0 | 0 | 0 | 100 | 0 | 90 | 5 | 100 | — | 0 |
| | Post | 4.00 | 0 | 25 | 0 | 0 | 0 | 46 | 16 | 16 | 0 | 0 |
| 91. | Pre | 4.00 | 0 | 0 | 100 | 0 | 0 | 0 | 0 | 0 | 0 | 0 |
| | Post | 4.00 | 15 | 35 | 90 | 10 | 50 | 10 | 50 | 0 | 0 | 0 |
| 92. | Pre | 2.00 | 0 | 0 | 0 | 0 | 0 | 36 | 6 | 36 | 0 | 2 |
| | Post | 2.00 | 0 | 0 | 0 | 0 | 0 | 0 | 0 | 0 | 0 | 0 |
| 93. | Pre | 4.00 | 0 | 0 | 0 | — | 0 | 98 | 100 | 90 | — | 71 |
| | Post | 4.00 | 0 | 20 | 0 | 0 | 15 | 20 | 15 | 0 | 0 | 0 |
| 94. | Pre | 4.00 | 0 | 0 | 100 | — | 0 | 100 | 100 | 100 | — | 71 |
| | Post | 4.00 | 0 | 15 | 0 | 0 | 46 | 10 | 15 | 15 | 0 | 0 |
| 95. | Pre | 4.00 | 100 | 0 | 61 | 100 | 100 | 100 | 100 | 100 | 100 | 91 |
| | Post | 4.00 | 0 | 35 | 10 | 0 | 31 | 71 | 0 | 21 | 0 | 21 |
| 96. | Pre | 4.00 | 0 | 5 | 100 | 100 | 100 | 100 | 100 | 99 | 100 | 98 |
| | Post | 4.00 | 0 | 20 | 0 | 0 | 31 | 25 | 0 | 26 | 85 | 21 |
| 97. | Pre | 4.00 | 0 | 0 | 0 | 0 | 0 | 85 | 100 | 90 | 0 | 70 |
| | Post | 4.00 | 0 | 0 | 0 | 0 | 0 | 0 | 0 | 0 | 0 | 0 |
| 98. | Pre | 4.00 | 0 | 100 | 0 | 0 | 0 | 5 | 98 | 5 | 0 | 40 |
| | Post | 4.00 | 0 | 0 | 0 | 0 | 0 | 0 | 0 | 0 | 0 | 0 |
| 99. | Pre | 4.00 | 0 | 0 | 0 | 0 | — | 85 | 100 | 90 | 0 | 0 |
| | Post | 4.00 | 0 | 0 | 0 | 0 | 0 | 0 | 0 | 0 | 0 | 0 |
| 100. | Pre | 4.00 | 0 | 0 | 0 | 0 | 0 | 75 | 10 | 35 | 0 | 0 |
| | Post | 4.00 | 0 | 0 | 0 | 0 | 0 | 0 | 0 | 0 | 0 | 0 |
| 101. | Pre | 4.00 | 0 | 0 | 0 | 0 | 0 | 80 | 90 | 90 | 0 | 0 |
| | Post | 4.00 | 0 | 0 | 0 | 0 | 0 | 0 | 0 | 0 | 0 | 0 |
| 102. | Pre | 4.00 | 0 | 0 | 100 | 0 | 90 | 100 | 98 | 100 | 100 | 95 |
| | Post | 4.00 | 0 | 0 | 0 | 0 | 0 | 30 | 15 | 5 | 0 | 0 |
| 103. | Pre | 4.00 | 0 | 50 | 100 | 60 | 70 | 98 | 100 | 100 | 90 | 70 |
| | Post | 4.00 | 0 | 15 | 0 | 0 | 0 | 50 | 10 | 0 | 0 | 0 |
| 104. | Pre | 4.00 | 0 | 10 | 100 | 0 | 95 | 100 | 100 | 85 | 0 | 80 |
| | Post | 4.00 | 0 | 0 | 0 | 0 | 0 | 15 | 0 | 0 | 0 | 20 |
| 105. | Pre | 4.00 | 0 | 0 | 90 | 0 | 0 | 100 | 100 | 40 | 0 | 20 |
| | Post | 4.00 | 0 | 0 | 0 | 0 | 0 | 10 | 25 | 0 | 0 | 0 |
| 106. | Pre | 4.00 | 0 | 0 | 100 | 45 | 0 | 100 | 100 | 100 | 0 | 20 |
| | Post | 4.00 | 5 | 5 | 10 | 0 | 0 | 30 | 0 | 0 | 0 | 0 |
| 107. | Pre | 4.00 | 0 | 0 | 100 | 0 | 0 | 100 | 100 | 85 | 100 | 85 |
| | Post | 4.00 | 0 | 15 | 0 | 10 | 0 | 0 | 0 | 0 | 0 | 0 |
| 108. | Pre | 4.00 | 0 | 65 | 100 | 99 | 100 | 100 | 100 | 100 | 100 | 100 |
| | Post | 4.00 | 0 | 5 | 0 | 0 | 15 | 40 | 20 | 60 | 0 | 0 |
| 109. | Pre | 4.00 | 0 | 0 | 100 | 100 | 60 | 100 | 100 | 100 | 75 | 85 |
| | Post | 4.00 | 10 | 0 | 10 | 0 | 20 | 15 | 15 | 20 | 15 | 0 |
| 110. | Pre | 4.00 | 0 | 0 | 0 | 0 | 0 | 50 | 0 | 0 | 0 | 0 |
| | Post | 4.00 | 10 | 15 | 10 | 0 | 0 | 0 | 0 | 0 | 0 | 0 |
| 111. | Pre | 4.00 | 45 | 95 | 100 | 100 | 80 | 100 | 100 | 100 | 80 | 100 |
| | Post | 4.00 | 0 | 25 | 0 | 10 | 10 | 35 | 10 | 30 | 10 | 25 |
| 112. | Pre | 4.00 | 0 | 0 | 100 | 65 | 0 | 90 | 98 | 85 | 55 | 95 |
| | Post | 4.00 | 0 | 5 | 0 | 0 | 0 | 0 | 0 | 0 | 20 | 0 |
| 113. | Pre | 4.00 | 0 | 0 | 100 | 0 | 0 | 99 | 100 | 100 | 0 | 85 |
| | Post | 4.00 | 0 | 0 | 0 | 0 | 0 | 0 | 0 | 0 | 0 | 0 |
| 114. | Pre | 4.00 | 0 | 0 | 0 | 0 | 20 | 100 | 100 | 100 | 0 | 95 |
| | Post | 4.00 | 0 | 0 | 0 | 0 | 0 | 0 | 0 | 0 | 0 | 0 |
| 115. | Pre | 4.00 | 0 | 20 | 100 | 100 | 40 | 100 | 100 | 100 | 100 | 100 |
| | Post | 4.00 | 0 | 0 | 0 | 0 | 0 | 15 | 30 | 15 | 0 | 0 |
| 116. | Pre | 4.00 | 25 | 30 | 100 | 100 | 80 | 100 | 100 | 100 | 100 | 100 |
| | Post | 4.00 | 10 | 15 | 10 | 15 | 0 | 50 | 45 | 25 | 15 | 60 |
| 117. | Pre | 4.00 | 25 | 30 | 100 | 100 | 70 | 100 | 100 | 100 | 100 | 100 |
| | Post | 4.00 | 0 | 0 | 0 | 0 | 0 | 50 | 50 | 25 | 0 | 80 |
| 118. | Pre | 4.00 | 0 | 0 | 0 | 0 | 0 | 90 | 95 | 75 | 10 | 15 |
| | Post | 4.00 | 0 | 0 | 0 | 0 | 0 | 0 | 0 | 0 | 0 | — |
| 119. | Pre | 4.00 | 25 | 25 | 100 | 90 | 75 | 100 | 100 | 100 | 50 | 100 |
| | Post | 4.00 | 10 | 10 | 0 | 0 | 10 | 50 | 40 | 30 | 10 | — |
| 120. | Pre | 1.00 | 60 | 0 | 0 | 0 | 15 | 100 | 100 | 90 | 0 | 30 |
| | Post | 1.00 | 0 | 10 | 0 | 0 | 0 | 25 | 0 | 50 | 0 | — |

TABLE 2A-continued

| Cpd No. | Appl Type | Rate lb/acre | CKL | MG | PIG | SMT | VEL | BYG | FOX | JON | NUT | WO |
|---|---|---|---|---|---|---|---|---|---|---|---|---|
| 121. | Pre | 1.00 | 15 | 0 | 100 | 25 | 10 | 100 | 100 | 95 | 0 | 70 |
| | Post | 1.00 | 0 | 10 | 0 | 0 | 0 | 80 | 0 | 65 | 0 | — |
| 122. | Pre | 1.00 | 0 | 0 | 0 | 35 | 0 | 100 | 100 | 100 | 0 | 20 |
| | Post | 1.00 | 0 | 0 | 0 | 0 | 0 | 45 | 0 | 0 | 0 | — |
| 123. | Pre | 1.00 | 65 | 20 | 100 | 85 | 85 | 100 | 100 | 100 | 75 | 80 |
| | Post | 4.00 | 0 | 20 | 0 | 0 | 55 | 80 | 30 | 35 | 15 | — |
| 124. | Pre | 4.00 | 0 | 25 | 100 | 100 | 60 | 100 | 100 | 100 | 100 | 90 |
| | Post | 4.00 | 0 | 15 | 0 | 0 | 25 | 5 | 85 | 15 | 0 | 0 |
| 125. | Pre | 2.00 | 0 | 0 | 0 | 0 | 0 | 15 | 20 | 0 | 0 | 0 |
| | Post | 2.00 | 0 | 0 | 0 | 0 | 0 | 0 | 0 | 0 | 0 | 0 |
| 126. | Pre | 4.00 | 0 | 0 | 100 | 40 | 15 | 100 | 100 | 100 | 100 | 85 |
| | Post | 4.00 | 0 | 0 | 0 | 0 | 25 | 80 | 80 | 30 | 80 | 10 |
| 127. | Pre | 1.00 | 10 | 100 | 100 | 85 | 65 | 100 | 100 | 98 | 80 | 100 |
| | Post | 1.00 | 0 | 15 | 90 | 10 | 0 | 80 | 85 | 25 | 70 | 70 |
| 128. | Pre | 1.00 | 0 | 100 | 100 | 85 | 10 | 100 | 100 | 100 | 100 | 98 |
| | Post | 1.00 | 0 | 0 | 0 | 0 | 0 | 80 | 80 | 35 | 40 | 20 |
| 129. | Pre | 1.00 | 0 | 0 | — | 100 | 10 | 100 | 100 | 95 | 10 | 95 |
| | Post | 1.00 | 0 | 15 | 0 | 0 | 20 | 0 | 10 | 0 | 0 | 0 |
| 130. | Pre | 4.00 | 0 | 0 | — | 0 | 0 | 95 | 90 | 85 | 0 | 0 |
| | Post | 4.00 | 0 | 0 | — | 0 | 0 | 0 | 0 | 0 | 0 | 0 |

*"—" means Not Tested

TABLE 2B

| Cpd No. | Appl Type | Rate lb/acre | BID | NS | PIG | SMT | VEL | BYG | CRB | FOX | MF | WO |
|---|---|---|---|---|---|---|---|---|---|---|---|---|
| 131. | Pre | 1.00 | 0 | 0 | —* | 0 | 0 | 100 | 80 | 99 | — | 20 |
| | Post | 1.00 | 0 | 15 | 35 | 0 | 10 | 0 | 0 | 10 | 0 | 0 |
| 132. | Pre | 1.00 | 100 | 90 | — | 100 | 75 | 100 | 100 | 100 | — | 90 |
| | Post | 1.00 | 0 | 45 | 20 | 0 | 0 | 75 | 0 | 60 | 20 | 25 |
| 133. | Pre | 1.00 | 98 | 85 | — | 95 | 70 | 100 | 100 | 100 | — | 98 |
| | Post | 1.00 | 0 | 0 | 70 | 0 | 15 | 80 | 10 | 60 | 25 | 65 |
| 134 | Pre | 1.00 | 0 | 0 | — | 80 | 20 | 100 | 100 | 100 | — | 25 |
| | Post | 1.00 | 0 | 15 | 25 | 0 | 25 | 0 | 15 | 0 | 0 | 0 |
| 135. | Pre | 1.00 | — | 80 | — | 100 | 35 | 100 | — | 100 | — | 100 |
| | Post | 1.00 | — | 0 | 10 | 25 | 0 | 85 | — | 0 | — | 60 |

*"—" means Not Tested

TABLE 2C

| Cpd No. | Appl Type | Rate lb/acre | BID | NS | SMT | VEL | BYG | CRB | FOX | MF |
|---|---|---|---|---|---|---|---|---|---|---|
| 136. | Pre | 1.00 | 20 | 50 | 0 | 50 | 0 | 0 | 0 | 0 |
| | Post | 1.00 | 25 | 25 | 0 | 25 | 0 | 0 | 0 | 0 |
| 137. | Pre | 1.00 | 90 | 90 | 100 | 90 | 100 | 100 | 100 | 100 |
| | Post | 1.00 | 20 | 70 | 20 | 20 | 75 | 90 | 60 | 0 |
| 138. | Pre | 1.00 | 100 | 100 | 100 | 80 | 100 | 100 | 100 | 100 |
| | Post | 1.00 | 95 | 95 | 100 | 90 | 90 | 95 | 80 | 80 |
| 139. | Pre | 1.00 | 0 | 0 | 0 | 0 | 95 | 100 | 100 | 0 |
| | Post | 1.00 | 0 | 20 | 0 | 20 | 0 | 0 | 0 | 0 |
| 140. | Pre | 1.00 | 0 | 0 | 0 | 0 | 95 | 95 | 100 | 95 |
| | Post | 1.00 | 10 | 0 | 0 | 0 | 80 | 0 | 0 | 0 |
| 141. | Pre | 1.00 | 90 | 95 | 100 | 100 | 100 | 100 | 100 | 100 |
| | Post | 1.00 | 60 | 40 | 60 | 25 | 95 | 80 | 25 | 10 |
| 142. | Pre | 1.00 | 100 | 95 | 100 | 100 | 100 | 100 | 100 | 100 |
| | Post | 1.00 | 80 | 80 | 50 | 20 | 90 | 95 | 40 | 10 |
| 143. | Pre | 1.00 | 95 | 100 | 100 | 95 | 100 | 100 | 100 | 100 |
| | Post | 1.00 | 40 | 75 | 10 | 25 | 95 | 90 | 60 | 0 |
| 144. | Pre | 1.00 | 10 | 95 | 0 | 0 | 100 | 100 | 95 | 0 |
| | Post | 1.00 | 0 | 0 | 0 | 0 | 75 | 0 | 0 | 0 |
| 145. | Pre | 1.00 | 75 | 60 | 0 | 0 | 100 | 95 | 100 | 100 |
| | Post | 1.00 | 20 | 0 | 0 | 0 | 75 | 0 | 0 | 0 |
| 146. | Pre | 1.00 | 0 | 60 | 0 | 4.00 | 100 | 100 | 100 | 80 |
| | Post | 1.00 | 10 | —* | 0 | 25 | 90 | 90 | 80 | 0 |
| 147. | Pre | 1.00 | 0 | 85 | 40 | 0 | 100 | 100 | 100 | 100 |
| | Post | 1.00 | 25 | — | 40 | 20 | 75 | 90 | 90 | 0 |
| 148. | Pre | 1.00 | 0 | 0 | 100 | 0 | 0 | 50 | 80 | 0 |
| | Post | 1.00 | 0 | 0 | 0 | 0 | 0 | 0 | 0 | 0 |
| 149. | Pre | 1.00 | 0 | 0 | 0 | 25 | 100 | 100 | 100 | 90 |
| | Post | 1.00 | 0 | 0 | 0 | 0 | 20 | 20 | 20 | 0 |
| 150. | Pre | 1.00 | 0 | — | 0 | 0 | 75 | 90 | 0 | 100 |
| | Post | 1.00 | 0 | 0 | 0 | 0 | 0 | 0 | 0 | 0 |
| 151. | Pre | 1.00 | 0 | 95 | 100 | 25 | 0 | 0 | 0 | 90 |
| | Post | 1.00 | 10 | 10 | 10 | 0 | 0 | 0 | 0 | 0 |
| 152. | Pre | 1.00 | 0 | — | 0 | 0 | 80 | 90 | 80 | 0 |
| | Post | 1.00 | 20 | 40 | 25 | 20 | 0 | 0 | 0 | 0 |
| 153. | Pre | 1.00 | 0 | — | 70 | 25 | 100 | 100 | 100 | 100 |

TABLE 2C-continued

| Cpd No. | Appl Type | Rate lb/acre | BID | NS | SMT | VEL | BYG | CRB | FOX | MF |
|---|---|---|---|---|---|---|---|---|---|---|
| | Post | 1.00 | 50 | 25 | 0 | 80 | 75 | 75 | 50 | 0 |
| 154. | Pre | 1.00 | 0 | 0 | 0 | 0 | 90 | 100 | 100 | 0 |
| | Post | 1.00 | 20 | 20 | 0 | 0 | 90 | 90 | 60 | 0 |
| 155. | Pre | 1.00 | 0 | 0 | 0 | 0 | 90 | 95 | 75 | 0 |
| | Post | 1.00 | 0 | 0 | 0 | 0 | 75 | 75 | 50 | 0 |
| 156. | Pre | 1.00 | 0 | 0 | 0 | 0 | 90 | 100 | 60 | 0 |
| | Post | 1.00 | 0 | 0 | 0 | 0 | 75 | 90 | 85 | 0 |
| 157. | Pre | 1.00 | 90 | 95 | 100 | 80 | 100 | 100 | 100 | 100 |
| | Post | 1.00 | 70 | 80 | 90 | 85 | 95 | 95 | 90 | 50 |
| 158. | Pre | 1.00 | 0 | 100 | 0 | 0 | 95 | 100 | 95 | 0 |
| | Post | 1.00 | 0 | 0 | 0 | 0 | 0 | 0 | 0 | 0 |
| 159. | Pre | 1.00 | 0 | 90 | 0 | 0 | 100 | 100 | 100 | 75 |
| | Post | 1.00 | 10 | 20 | 0 | 0 | 40 | 70 | 0 | 0 |
| 160. | Pre | 1.00 | 80 | 20 | 0 | 0 | 100 | 100 | 100 | 50 |
| | Post | 1.00 | 10 | 0 | 0 | 0 | 95 | 90 | 80 | 0 |
| 161. | Pre | 1.00 | 20 | 90 | 100 | 90 | 95 | 100 | 100 | 70 |
| | Post | 1.00 | 20 | 20 | 0 | 20 | 0 | 0 | 0 | 0 |
| 162. | Pre | 1.00 | 0 | 25 | 0 | 0 | 95 | 100 | 95 | 0 |
| | Post | 1.00 | 40 | 40 | 0 | 60 | 75 | 90 | 75 | 60 |
| 163. | Pre | 1.00 | 0 | 0 | 0 | 0 | 90 | 95 | 100 | 80 |
| | Post | 1.00 | 35 | 35 | 0 | 0 | 0 | 0 | 0 | 0 |
| 164. | Pre | 1.00 | 0 | 0 | 90 | 0 | 60 | 0 | 0 | 0 |
| | Post | 1.00 | 0 | 0 | 0 | 0 | 0 | 0 | 0 | 0 |
| 165. | Pre | 1.00 | 0 | 0 | 0 | 0 | 95 | 95 | 80 | 20 |
| | Post | 1.00 | 30 | 50 | 50 | 70 | 0 | 0 | 0 | 0 |
| 166. | Pre | 1.00 | 0 | 50 | 0 | 40 | 0 | 0 | 0 | 0 |
| | Post | 1.00 | 0 | 0 | 0 | 0 | 0 | 0 | 0 | 0 |
| 167. | Pre | 1.00 | 0 | 70 | 60 | 70 | 100 | 100 | 100 | 95 |
| | Post | 1.00 | 70 | 60 | 20 | 60 | 90 | 80 | 80 | 20 |
| 168. | Pre | 1.00 | 0 | 0 | 0 | 0 | 90 | 90 | 90 | 0 |
| | Post | 1.00 | 0 | 10 | 0 | 25 | 0 | 0 | 0 | 0 |
| 169. | Pre | 1.00 | 0 | 20 | 0 | 40 | 100 | 100 | 95 | 80 |
| | Post | 1.00 | 35 | 40 | 0 | 40 | 20 | 40 | 25 | 0 |
| 170. | Pre | 1.00 | 0 | 25 | 100 | 0 | 100 | 100 | 100 | 100 |
| | Post | 1.00 | 10 | 20 | 0 | 0 | 90 | 90 | 60 | 90 |
| 171. | Pre | 1.00 | 0 | 50 | 20 | 70 | 100 | 100 | 95 | 100 |
| | Post | 1.00 | 0 | 0 | 0 | 0 | 80 | 80 | 60 | 0 |
| 172. | Pre | 1.00 | 0 | 20 | 10 | 0 | 100 | 95 | 100 | 95 |
| | Post | 1.00 | 20 | 0 | 0 | 0 | 90 | 90 | 50 | 0 |
| 173. | Pre | 1.00 | 0 | 0 | 0 | 0 | 20 | 90 | 90 | 25 |
| | Post | 1.00 | 0 | 0 | 0 | 0 | 60 | 75 | 75 | 0 |
| 174. | Pre | 1.00 | 0 | 0 | 0 | 0 | 0 | 75 | 0 | 0 |
| | Post | 1.00 | 0 | 0 | 0 | 0 | 0 | 0 | 25 | 0 |
| 175. | Pre | 1.00 | 0 | 0 | 0 | 0 | 100 | 100 | 100 | 0 |
| | Post | 1.00 | 0 | 0 | 0 | 0 | 50 | 95 | 40 | 0 |
| 176. | Pre | 1.00 | 0 | 0 | 40 | 0 | 95 | 100 | 95 | 60 |
| | Post | 1.00 | 0 | 0 | 0 | 0 | 85 | 90 | 80 | 0 |
| 177. | Pre | 1.00 | 25 | 10 | 50 | 70 | 0 | 100 | 85 | 0 |
| | Post | 1.00 | 0 | 0 | 0 | 0 | 0 | 0 | 0 | 0 |
| 178. | Pre | 1.00 | 25 | 0 | 25 | 0 | 60 | 0 | 95 | 0 |
| | Post | 1.00 | 0 | 0 | 0 | 0 | 0 | 0 | 0 | 0 |
| 179. | Pre | 1.00 | 0 | 25 | 0 | 0 | 100 | 100 | 100 | 60 |
| | Post | 1.00 | 20 | 20 | 0 | 70 | 95 | 95 | 80 | 0 |
| 180. | Pre | 1.00 | 0 | 0 | 0 | 0 | 95 | 100 | 90 | 90 |
| | Post | 1.00 | 0 | 0 | 0 | 0 | 90 | 90 | 80 | 0 |
| 181. | Pre | 1.00 | 0 | 0 | 0 | 0 | 90 | 100 | 95 | 95 |
| | Post | 1.00 | 0 | 0 | 0 | 0 | 40 | 80 | 25 | 0 |
| 182. | Pre | 1.00 | 0 | 0 | 0 | 70 | 100 | 100 | 100 | 80 |
| | Post | 1.00 | 60 | 60 | 0 | 75 | 95 | 90 | 85 | 70 |
| 183. | Pre | 1.00 | 0 | 0 | 0 | 0 | 80 | 100 | 95 | 20 |
| | Post | 1.00 | 10 | 20 | 0 | 20 | 10 | 0 | 10 | 0 |
| 184. | Pre | 1.00 | 0 | 0 | 0 | 0 | 90 | 100 | 90 | 50 |
| | Post | 1.00 | 0 | 60 | 0 | 25 | 70 | 85 | 20 | 0 |
| 185. | Pre | 1.00 | 0 | 0 | 0 | 0 | 95 | 100 | 95 | 90 |
| | Post | 1.00 | 50 | 50 | 20 | 10 | 70 | 70 | 75 | 40 |
| 186. | Pre | 1.00 | 100 | 90 | 0 | 0 | 95 | — | 95 | 40 |
| | Post | 1.00 | 70 | 90 | 0 | 0 | 80 | 80 | 70 | 70 |
| 187. | Pre | 1.00 | 90 | 75 | 0 | 20 | 95 | — | 95 | 85 |
| | Post | 1.00 | 75 | 75 | 60 | 75 | 85 | 90 | 85 | 60 |
| 188. | Pre | 1.00 | 90 | 0 | 0 | 0 | 50 | — | 90 | 40 |
| | Post | 1.00 | 0 | 0 | 0 | 0 | 0 | 0 | 65 | 0 |
| 189. | Pre | 1.00 | 95 | 95 | 0 | 0 | 95 | — | 100 | 75 |
| | Post | 1.00 | 10 | 0 | 0 | 0 | 40 | 75 | 40 | 0 |
| 190. | Pre | 1.00 | 0 | 20 | 100 | 0 | 95 | 0 | 100 | 60 |
| | Post | 1.00 | 70 | 70 | 0 | 0 | 80 | 80 | 20 | 0 |
| 191. | Pre | 1.00 | 0 | 75 | 100 | 25 | 100 | 100 | 100 | 60 |
| | Post | 1.00 | 60 | 70 | 0 | 50 | 85 | 85 | 50 | 70 |
| 192. | Pre | 1.00 | 0 | 90 | 100 | 0 | 100 | 100 | 100 | 70 |
| | Post | 1.00 | 25 | 70 | 0 | 20 | 85 | 90 | 60 | 25 |
| 193. | Pre | 1.00 | 0 | 85 | 100 | 0 | 100 | 100 | 100 | 50 |

TABLE 2C-continued

| Cpd No. | Appl Type | Rate lb/acre | BID | NS | SMT | VEL | BYG | CRB | FOX | MF |
|---|---|---|---|---|---|---|---|---|---|---|
| | Post | 1.00 | 60 | 70 | 0 | 25 | 85 | 80 | 70 | 40 |
| 194. | Pre | 1.00 | 100 | 95 | 100 | 0 | 100 | 100 | 100 | 100 |
| | Post | 1.00 | 25 | 50 | 0 | 10 | 75 | 80 | 60 | 25 |
| 195. | Pre | 1.00 | 0 | 0 | 0 | 0 | 90 | 100 | 95 | 85 |
| | Post | 1.00 | 25 | 10 | 0 | 0 | 70 | 85 | 0 | 40 |
| 196. | Pre | 1.00 | 100 | 100 | — | 0 | 100 | 100 | 100 | 25 |
| | Post | 1.00 | 20 | 60 | 0 | 10 | 90 | 85 | 85 | 80 |
| 197. | Pre | 1.00 | 40 | 95 | — | 25 | 100 | 100 | 95 | 75 |
| | Post | 1.00 | 70 | 90 | 0 | 60 | 90 | 90 | 85 | 85 |
| 198. | Pre | 1.00 | 95 | 95 | — | 0 | 95 | 50 | 95 | 50 |
| | Post | 1.00 | 50 | 75 | 0 | 0 | 85 | 90 | 85 | 70 |
| 199. | Pre | 1.00 | 100 | 100 | — | 85 | 100 | 100 | 100 | 100 |
| | Post | 1.00 | 85 | 70 | 0 | 60 | 90 | 90 | 85 | 85 |
| 200. | Pre | 1.00 | 90 | 70 | — | 20 | 95 | 100 | 95 | 95 |
| | Post | 1.00 | 10 | 20 | 0 | 0 | 80 | 90 | 60 | 0 |
| 201. | Pre | 1.00 | 80 | 100 | — | 40 | 100 | 95 | 100 | 100 |
| | Post | 1.00 | 80 | 90 | 0 | 50 | 95 | 85 | 70 | 40 |
| 202. | Pre | 1.00 | 40 | 85 | — | 0 | 95 | 100 | 80 | 50 |
| | Post | 1.00 | 60 | 80 | 50 | 40 | 85 | 90 | 80 | 70 |
| 203. | Pre | 1.00 | 25 | 40 | 0 | 0 | 25 | 0 | 75 | 20 |
| | Post | 1.00 | 40 | 20 | 0 | 10 | 10 | 0 | 10 | 0 |
| 204. | Pre | 1.00 | 90 | 100 | 0 | 0 | 0 | 0 | 90 | 0 |
| | Post | 1.00 | 0 | 0 | 0 | 0 | 0 | 0 | 0 | 0 |
| 205. | Pre | 1.00 | 0 | 40 | 0 | 0 | 90 | 0 | 90 | 0 |
| | Post | 1.00 | 0 | 0 | 0 | 10 | 0 | 0 | 0 | 0 |
| 206. | Pre | 1.00 | 0 | 50 | 0 | 0 | 90 | 100 | 100 | 0 |
| | Post | 1.00 | 175 | 25 | 20 | 20 | 25 | 20 | 25 | 0 |
| 207. | Pre | 1.00 | 0 | 0 | 0 | 0 | 90 | 0 | 95 | 0 |
| | Post | 1.00 | 0 | 0 | 0 | 0 | 0 | 0 | 0 | 0 |
| 208. | Pre | 1.00 | 0 | 0 | 0 | 0 | 100 | 100 | 100 | 80 |
| | Post | 1.00 | 10 | 25 | 0 | 20 | 0 | 20 | 10 | 0 |
| 209. | Pre | 1.00 | 90 | 85 | 0 | 0 | 95 | 100 | 100 | 90 |
| | Post | 1.00 | 20 | 25 | 0 | 20 | 0 | 0 | 0 | 0 |
| 210. | Pre | 1.00 | 0 | 0 | 0 | 0 | 0 | 0 | 0 | 0 |
| | Post | 1.00 | 0 | 20 | 0 | 0 | 0 | 0 | 0 | 0 |
| 213. | Pre | 1.00 | 100 | 100 | 0 | 60 | 90 | — | 100 | 80 |
| | Post | 1.00 | 10 | 65 | 10 | 20 | 25 | 10 | 10 | 0 |
| 214. | Pre | 1.00 | 50 | 100 | 0 | 20 | 95 | — | 90 | 100 |
| | Post | 1.00 | 85 | 60 | 40 | 50 | 85 | 75 | 65 | 25 |
| 215. | Pre | 1.00 | 0 | 70 | 0 | 0 | 95 | 100 | 100 | 100 |
| | Post | 1.00 | 20 | 85 | 50 | 50 | 85 | 90 | 90 | 75 |
| 216. | Pre | 1.00 | 0 | 85 | 10 | 100 | 100 | 100 | 0 | 0 |
| | Post | 1.00 | 50 | 75 | 0 | 10 | 50 | 85 | 85 | 0 |
| 218. | Pre | 1.00 | 100 | 95 | 100 | 40 | 0 | 0 | 0 | 0 |
| | Post | 1.00 | 0 | 0 | 0 | 0 | 0 | 0 | 0 | 0 |
| 219. | Pre | 1.00 | 95 | 95 | 0 | 10 | 100 | 100 | 100 | 100 |
| | Post | 1.00 | 10 | 85 | 0 | 20 | 90 | 90 | 25 | 50 |
| 221. | Pre | 1.00 | 100 | 95 | 0 | 25 | 100 | 100 | 100 | 100 |
| | Post | 1.00 | 60 | 40 | 0 | 20 | 85 | 90 | 60 | 50 |
| 222. | Pre | 1.00 | 85 | 90 | 0 | 0 | 95 | 95 | 100 | 90 |
| | Post | 1.00 | 25 | 70 | 0 | 60 | 75 | 75 | 75 | 60 |
| 223. | Pre | 1.00 | 20 | 80 | 0 | 0 | 100 | 100 | 100 | 95 |
| | Post | 1.00 | 25 | 60 | 10 | 50 | 50 | 70 | 60 | 60 |
| 224. | Pre | 1.00 | 95 | 20 | 0 | 0 | 50 | 100 | 40 | 0 |
| | Post | 1.00 | 0 | 20 | 0 | 10 | 0 | 60 | 0 | 0 |
| 225. | Pre | 1.00 | 0 | 0 | 0 | 0 | 0 | 0 | 0 | 0 |
| | Post | 1.00 | 10 | 35 | 10 | 25 | 0 | 0 | 0 | 0 |
| 226. | Pre | 1.00 | 80 | 60 | 0 | 0 | 95 | 100 | 95 | 10 |
| | Post | 1.00 | 40 | 60 | 0 | 60 | 40 | 70 | 60 | 0 |
| 227. | Pre | 1.00 | 0 | 40 | 0 | 0 | 85 | 90 | 90 | 60 |
| | Post | 1.00 | 20 | 35 | 0 | 20 | 35 | 0 | 25 | 0 |
| 228. | Pre | 1.00 | 0 | 10 | 0 | 0 | 95 | 85 | 95 | 90 |
| | Post | 1.00 | 10 | 70 | 0 | 25 | 40 | 80 | 70 | 0 |
| 229. | Pre | 1.00 | 90 | 95 | 0 | 40 | 100 | 100 | 100 | 95 |
| | Post | 1.00 | 70 | 85 | 20 | 60 | 90 | 80 | 80 | 40 |
| 230. | Pre | 1.00 | 0 | 80 | 0 | 0 | 90 | — | 95 | — |
| | Post | 1.00 | 10 | 10 | 0 | 10 | 10 | 85 | 20 | 0 |
| 231. | Pre | 1.00 | 0 | 25 | 0 | 0 | 100 | — | 100 | — |
| | Post | 1.00 | 10 | 30 | 0 | 10 | 60 | 75 | 60 | 0 |
| 232. | Pre | 1.00 | 100 | 70 | 0 | 0 | 70 | — | 90 | — |
| | Post | 1.00 | 10 | 10 | 0 | 10 | 40 | 85 | 10 | 0 |
| 233. | Pre | 1.00 | 0 | 95 | 0 | 0 | 95 | 100 | 90 | 25 |
| | Post | 1.00 | 80 | 0 | 0 | 20 | 80 | 85 | 75 | 80 |
| 234. | Pre | 1.00 | 100 | 95 | 50 | 20 | 100 | 100 | 100 | 100 |
| | Post | 1.00 | 95 | 75 | 60 | 75 | 95 | 95 | 80 | 75 |
| 235. | Pre | 1.00 | 0 | 0 | 0 | 0 | 50 | 90 | 75 | 0 |
| | Post | 1.00 | 0 | 0 | 0 | 0 | 50 | 0 | 0 | 0 |
| 236. | Pre | 1.00 | 0 | 85 | 0 | 20 | 95 | 100 | 100 | 95 |
| | Post | 1.00 | 0 | 50 | 20 | 0 | 90 | 90 | 90 | 50 |
| 237. | Pre | 1.00 | 0 | 60 | 0 | 0 | 100 | 100 | 95 | 100 |

TABLE 2C-continued

| Cpd No. | Appl Type | Rate lb/acre | BID | NS | SMT | VEL | BYG | CRB | FOX | MF |
|---|---|---|---|---|---|---|---|---|---|---|
| | Post | 1.00 | 0 | 25 | 0 | 0 | 90 | 90 | 85 | 60 |
| 238. | Pre | 1.00 | 0 | 25 | 0 | 0 | 95 | 95 | 95 | 90 |
| | Post | 1.00 | 0 | 20 | 20 | 0 | 80 | 80 | 80 | 25 |
| 239. | Pre | 1.00 | 100 | 75 | 0 | 0 | 100 | 100 | 100 | 100 |
| | Post | 1.00 | 50 | 40 | 50 | 0 | 90 | 90 | 80 | 50 |
| 240. | Pre | 1.00 | 0 | 0 | 0 | 0 | 95 | 95 | 80 | 70 |
| | Post | 1.00 | 0 | 0 | 0 | 20 | 50 | 85 | 85 | 0 |
| 241. | Pre | 1.00 | 0 | 0 | 0 | 0 | 95 | 100 | 0 | 0 |
| | Post | 1.00 | 0 | 0 | 0 | 0 | 50 | 90 | 85 | 0 |
| 242. | Pre | 1.00 | 0 | 60 | 0 | 0 | 100 | 100 | 95 | 95 |
| | Post | 1.00 | 0 | 10 | 0 | 0 | 70 | 90 | 70 | 0 |
| 243. | Pre | 1.00 | 0 | 0 | 0 | 0 | 80 | 90 | 85 | 20 |
| | Post | 1.00 | 0 | 0 | 0 | 0 | 0 | 0 | 0 | 0 |
| 244. | Pre | 1.00 | 0 | 0 | 0 | 0 | 95 | 100 | 95 | 100 |
| | Post | 1.00 | 0 | 0 | 0 | 0 | 50 | 50 | 50 | 0 |
| 245. | Pre | 1.00 | 0 | 0 | 0 | 0 | 95 | 100 | 95 | 85 |
| | Post | 1.00 | 0 | 0 | 0 | 0 | 60 | 80 | 75 | 0 |
| 246. | Pre | 1.00 | 0 | 0 | 0 | 0 | 95 | 60 | 90 | 60 |
| | Post | 1.00 | 10 | 0 | 10 | 0 | 0 | 20 | 0 | 0 |
| 247. | Pre | 1.00 | 0 | 0 | 0 | 0 | 50 | 100 | 95 | 40 |
| | Post | 1.00 | 0 | 0 | 0 | 0 | 0 | 0 | 0 | 0 |
| 248. | Pre | 1.00 | 0 | 0 | 0 | 0 | 95 | 95 | 95 | 0 |
| | Post | 1.00 | 20 | 40 | 0 | 20 | 0 | 75 | 0 | 0 |
| 249. | Pre | 1.00 | 10 | 90 | 0 | 0 | 95 | 100 | 100 | 95 |
| | Post | 1.00 | 0 | 0 | 0 | 0 | 0 | 0 | 0 | 0 |
| 250. | Pre | 1.00 | 0 | 95 | 0 | 0 | 85 | 95 | 95 | 0 |
| | Post | 1.00 | 0 | 0 | 10 | 0 | 0 | 0 | 0 | 0 |
| 251. | Pre | 1.00 | 90 | 95 | 20 | 40 | 100 | 100 | 100 | 100 |
| | Post | 1.00 | 20 | 80 | 0 | 70 | 90 | 90 | 75 | 40 |
| 252. | Pre | 1.00 | 85 | 100 | 10 | 25 | 95 | 95 | 95 | 100 |
| | Post | 1.00 | 50 | 80 | 10 | 70 | 85 | 80 | 70 | 70 |
| 253. | Pre | 1.00 | 0 | 70 | 0 | 0 | 95 | 100 | 100 | 100 |
| | Post | 1.00 | 10 | 25 | 0 | 0 | 10 | 75 | 25 | 0 |
| 254. | Pre | 1.00 | 100 | 100 | 0 | 70 | 100 | 100 | 100 | 100 |
| | Post | 1.00 | 80 | 80 | 20 | 40 | 70 | 85 | 80 | 50 |
| 255. | Pre | 1.00 | — | — | 0 | 50 | 100 | 100 | 100 | 100 |
| | Post | 1.00 | 60 | 60 | 40 | 80 | 85 | 95 | 75 | 60 |
| 256. | Pre | 1.00 | 95 | 95 | 100 | 0 | 100 | 100 | 100 | 100 |
| | Post | 1.00 | 25 | 80 | 0 | 25 | 80 | 95 | 90 | 90 |

*"—" means Not Tested

The compounds of this invention are active herbicidally on monocot and dicot weeds, in either pre- or postemergence applications. In general, they require lower doses to control monocot weeds preemergence. In particular, several annual grasses, such as *Echinochloa crusgalli*, *Digitaria sanguinalis* and *Setaria viridis* are especially sensitive. These materials generally show selectivity to several agronomically important crops such as cotton, rice, soybean, sugarbeet, sunflower, peanuts and wheat, particularly cotton and rice.

The invention is most effective when formulated in an appropriate carrier, such that the dissolved or dispersed compound is readily applied over the plants or soil in a homogeneous manner.

The invention is also effective when used as a part of a mixture of herbicides formulated in the above manner.

The present herbicides may be applied in any amount which will give the required control of the undesired plants. Generally a rate of application of the herbicides of the invention is from about 0.001 to about 8 pounds per acre and preferably from about 0.01 to about 4 pounds of the compound per acre. Most preferably a rate from about 0.02 to about 1 pound per acre is used.

The compounds of the present invention are useful both as preemergence and postemergence herbicides. Preemergence herbicides may be applied to the soil surface or incorporated into the soil. Postemergence herbicides are those which are applied after the plants have emerged and during their growth period. The compounds of the present invention may be applied to the soil surface prior to plant emergence or incorporated into the soil or other growth medium prior to planting. This incorporation can be carried out by any convenient means, including by simply mixing with the soil, by applying the compound to the surface of the soil and then disking or dragging into the soil to the desired depth, or by employing a liquid carrier to accomplish the necessary penetration and impregnation.

A compound of the present invention can be applied postemergence to the growth medium or to plants to be treated either by itself, or, as is generally done, as a component in a herbicidal composition or formulation which also comprises an agronomically acceptable carrier.

By agronomically acceptable carrier is meant any substance which can be used to dissolve, disperse or diffuse a herbicidal compound in the composition without impairing the effectiveness of the herbicidal compound and which by itself has no detrimental effect on the soil, equipment, crops or agronomic environment. Mixtures of the compounds of the present invention may also be used in any of these herbicidal formulations. The herbicidal compositions of the invention can be either solid or liquid formulations or solutions. For example, the compounds can be formulated as wettable powders, solutions, emulsifiable concentrates, dusts, granular formulations, aerosols, water dispersable granular formulations or flowable concentrates as is known to one skilled in the art. In such formulations, the compounds are extended with a liquid or solid carrier and, when desired, suitable surfactants or emulsifiers are incorporated.

It is usually desirable, particularly in postemergence applications, to include adjuvants such as wetting agents, spreading agents, dispersing agents, sticking agents, adhesives and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide and the like. Mixtures of these solvents can also be used. The concentration of compound in the solution can vary from about 2% to about 98%.

The compounds of the present invention can also be mixed with fertilizers or fertilizing materials before their application. In one type of solid fertilizing composition in which the compounds may be used, particles of a fertilizer or fertilizing ingredients, such as ammonium sulfate, ammonium nitrate or ammonium phosphate can be coated with one or more of the herbicides. The solid herbicide and solid fertilizing material may also be admixed in blending or mixing equipment, or they can be incorporated with fertilizers in granular formulations. Any relative proportion of herbicide and fertilizer can be used which is suitable for the crops and weeds to be treated.

The compounds of the present invention may be applied as herbicidal sprays by methods commonly employed, such as conventional high-gallonage hydraulic sprays, low gallonage sprays, air blast spray, aerial sprays and dusts. For some applications, two or more of the compounds of the instant invention may be combined, thereby providing additional advantages and effectiveness. When mixtures of the compounds of the invention are used, the relative proportion of each compound used will depend on the relative efficacy of the compounds in the mixture with respect to the plants to be treated.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

Carboxylic Acids and Derivatives 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate;
trichloroacetic acid and its salts;
2,2-dichloropropionic acid and its salts;
2,3-dichloroisobutyric acid and its salts;
isopropylammonium 2-(4-isopropyl-5-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
m-toluic acid, 6-(4-isopropyl-4-methyl-5-oxo-2-imidazolin-2-yl)methyl ester and
p-toluic acid, 6-(4-isopropyl-4-methyl-5-oxo-2-imidazolin-2-yl)-, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

Carbamic Acid Derivatives ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiocarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

Substituted Ureas 2-chloro-N-[(4-methoxy-6-methyl-1,3,5-triazin-2-yl)aminocarbonyl]benzenesulfonamide;3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
dichloral urea;
methyl 2-[[[[(4,6-dimethyl-2-pyrimidinyl)amino]carbonyl]amino]sulfonyl]benzoate;
N-((6-methoxy-4-methyl-1,3,5-triazin-2-yl)aminocarbonyl)-2-(2-chloroethoxy)benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate;
methyl 3-[[(4-methoxy-6-methyl-1,3,5-triazin-2-yl)aminocarbonyl]aminosulfonyl]-2-thiophenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

Substituted Triazines 2-chloro-4,6-bis(ethylamino)-s-triazine;

2-chloro-4-ethylamino-6-isopropylamino-s-triazine;
2-chloro-4,6-bis(methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

Diphenyl Ether Derivatives 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)phenoxyl]-2-nitrobenzoate;
5-[2-chloro-4-(trifluoromethyl)phenoxyl]-N-(methylsulphonyl)-2-nitrobenzamide;

Anilides 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

Oxyphenoxy Herbicides 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;
2-[4-[(6-chloro-2-quinoxalinyl)oxy]phenoxy]propionic acid, ethyl ester;

Uracils 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

Nitriles 2,6-dichlorobenzonitrile; diphenylacetonitrile;
3,5-dibromo-4-hydroxybenzonitrile;
3,5-diiodo-4-hydroxybenzonitrile;

Other Organic Herbicides 2-chloro-N,N-diallylacetamide;
N-(1,1-dimethyl-2-propynyl)-3,5-dichlorobenzamide;
maleic hydrazide;
3-amino-1,2,4-triazole;
monosodium methanearsonate;
disodium methanearsonate;
N,N-dimethyl-alpha,alpha-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone;
2-(3,5-dichlorophenyl)-2-(2,2,2-trichloromethyl)oxirane.
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone;
2-(3,5-dichlorophenyl)-2-(2,2,2-trichloromethyl)oxirane.

It is to be understood that changes and variations may be made without departing from the spirit and scope of the invention as defined by the appended claims.

What is claimed is:

1. A herbicidal composition which comprises an agronomically acceptable carrier and a herbicidally effective amount of a compound of the formula

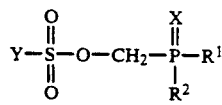

wherein
- (1) Y is selected from a phenyl; a naphthyl; a benzyl; a ($C_5$-$C_8$)cycloalkyl; a 5-membered heteroaromatic ring having 1, 2, 3, or 4 heteroatoms independently selected from the group consisting of nitrogen, oxygen and sulfur atoms provided no more than one heteroatom is oxygen or sulfur; a 6-membered heteroaromatic ring having 1, 2 or 3 nitrogen atoms; a fused 5,6-membered heteroaromatic ring having 1–4 heteroatoms independently selected from the group consisting of nitrogen, oxygen and sulfur atoms provided no more than one heteroatom is oxygen or sulfur; or a fused 6,6-membered heteroaromatic ring having 1–4 heteroatoms independently selected from the group consisting of nitrogen, oxygen and sulfur atoms provided no more than one heteroatom is oxygen or sulfur;

wherein each of said Y may be substituted with up to three substituents each independently selected from halogen, cyano, nitro, alkoxy, haloalkoxy, alkyl, haloalkyl, phenyl, alkylcarbonyloxy, dialkylcarbamoyl and alkoxycarbonyl, provided
  - (a) there is at most one of said substituents on said Y when Y is a thiadiazolyl ring or a tetrazolyl ring,
  - (b) there is at most two of said substituents when Y is a triazolyl ring, a thiazolyl ring, or an isothiazolyl ring, and
  - (c) when Y is phenyl, naphthyl or benzyl, there can be four or five of said substituents selected from halogen, acetoxy, methyl, methoxy and halomethoxy but no more than two substituents are selected from acetoxy, methyl, methoxy, and halomethoxy;
- (2) X is oxygen or sulfur; and
- (3) $R^1$ and $R^2$ are each independently selected from alkyl, alkoxy, alkylthio, alkenyloxy, alkynyloxy, haloalkoxy, cyanoalkoxy, alkoxyalkoxy, cycloalkyloxy, cycloalkylalkoxy, alkylideneiminooxy, chloro and amino with one or two substituents selected from the group consisting of alkyl, alkenyl and phenyl; provided that there is no more than one phenyl group on the amino group, and provided that $R^1$ may be selected additionally from phenyl or phenoxy; and provided that $R^1$ and $R^2$ both can be alkoxy, taken together with the phosphorus atom to form a 6-membered oxygen-containing ring, except that when $R^1$ and $R^2$ are both alkoxy, Y is not phenyl, 4-methylphenyl, 4-chlorophenyl, 4-bromophenyl or 3-nitrophenyl.

2. The composition of claim 1 wherein
Y is substituted with up to three substituents each independently selected from halogen, cyano, nitro, ($C_1$-$C_6$)alkoxy, halo($C_1$-$C_4$)alkoxy, ($C_1$-$C_6$)alkyl, halo($C_1$-$C_4$)alkyl, phenyl, ($C_1$-$C_4$)alkylcarbonyloxy, di($C_1$-$C_4$)alkylcarbamoyl and ($C_1$-$C_4$)alkoxycarbonyl, and $R^1$ and $R^2$ are each independently selected from ($C_1$-$C_6$)alkyl, ($C_1$-$C_6$)alkoxy, halo($C_2$-$C_4$)alkoxy, ($C_1$-$C_4$)alkylthio, ($C_3$-$C_4$)alkenyloxy, ($C_3$-$C_4$)alkynyloxy, ($C_1$-$C_4$)alkoxy($C_1$-$C_4$)alkoxy, ($C_4$-$C_8$)cycloalkyloxy, ($C_3$-$C_6$)cycloalkyl($C_1$-$C_3$)alkoxy, cyano($C_1$-$C_4$)alkoxy, ($C_2$-$C_4$)alkylideneiminooxy, chloro, and amino substituted with one or two substituents selected from ($C_1$-$C_4$)alkyl, ($C_2$-$C_4$)alkenyl and phenyl provided there is not more than one phenyl group on the amino group, additionally, $R^1$ may be selected from phenyl or phenoxy; or $R^1$ and $R^2$ are both alkoxy, taken together with the phosphorous atom to form a 6-membered oxygen-containing ring.

* * * * *